US009169458B2

(12) United States Patent
Shimazu et al.

(10) Patent No.: US 9,169,458 B2
(45) Date of Patent: Oct. 27, 2015

(54) MUTATED ALKALINE CELLULASE

(75) Inventors: Ayako Shimazu, Haga-gun (JP); Keiji Endo, Haga-gun (JP); Mitsuyoshi Okuda, Haga-gun (JP)

(73) Assignee: Kao Corporation, Tokyo (JP)

( * ) Notice: Subject to any disclaimer, the term of this patent is extended or adjusted under 35 U.S.C. 154(b) by 559 days.

(21) Appl. No.: 13/583,508

(22) PCT Filed: Mar. 11, 2011

(86) PCT No.: PCT/JP2011/055831
§ 371 (c)(1),
(2), (4) Date: Sep. 7, 2012

(87) PCT Pub. No.: WO2011/111836
PCT Pub. Date: Sep. 15, 2011

(65) Prior Publication Data
US 2013/0029897 A1 Jan. 31, 2013

(30) Foreign Application Priority Data

Mar. 12, 2010 (JP) .................. 2010-056059
Mar. 12, 2010 (JP) .................. 2010-056060
Mar. 18, 2010 (JP) .................. 2010-063212

(51) Int. Cl.
| | | |
|---|---|---|
| C12N 9/42 | (2006.01) | |
| C12N 1/20 | (2006.01) | |
| C12N 15/00 | (2006.01) | |
| C07H 21/04 | (2006.01) | |
| C11D 3/386 | (2006.01) | |

(52) U.S. Cl.
CPC .......... *C11D 3/38645* (2013.01); *C12N 9/2437* (2013.01); *C12Y 302/01004* (2013.01)

(58) Field of Classification Search
None
See application file for complete search history.

(56) References Cited

U.S. PATENT DOCUMENTS

| | | | |
|---|---|---|---|
| 7,033,981 B2 | 4/2006 | Hakamada et al. | |
| 2004/0002431 A1 | 1/2004 | Hakamada et al. | |
| 2005/0112749 A1 | 5/2005 | Outtrup et al. | |
| 2005/0215450 A1 | 9/2005 | Outtrup et al. | |
| 2005/0287656 A1 | 12/2005 | Hakamada et al. | |
| 2006/0035800 A1 | 2/2006 | Gibson et al. | |
| 2007/0179076 A1 | 8/2007 | Gibson et al. | |

FOREIGN PATENT DOCUMENTS

| | | |
|---|---|---|
| CN | 1458274 A | 11/2003 |
| EP | 1 350 843 A2 | 3/2003 |
| JP | 2002-265998 A | 9/2002 |
| JP | 2003-310270 A | 11/2003 |
| JP | 2003-313593 A | 11/2003 |
| JP | 2004-000140 A | 1/2004 |
| JP | 3512981 B2 | 3/2004 |
| JP | 2004-536593 A | 12/2004 |
| JP | 2006-509850 A | 3/2006 |
| JP | 2006-296268 A | 11/2006 |
| JP | 4261817 B2 | 4/2009 |

OTHER PUBLICATIONS

Hakamada et al. Identification of thermostabilizing residues in a bacillus alkaline cellulase by construction of chimeras from mesophilic and thermostable enzymes and site directed mutagenesis, FEMS Microbiology Letters 195(2001), 67-72.*
Hakamada, Y et al., "Deduced amino acid sequence and possible catalytic residues of a thermostable, alkaline cellulase from an Alkaliphilic bacillus strain," Biosci Biotechnol Biochem, Nov. 2000; 64(11): 2281-2289, Taylor & Francis, Oxfordshire, UK.
Zhang, HongXi, Shandong University Master's Thesis, "Cellulase directed evolution, site-directed mutagenesis and mechanism of alkali," Chima Master's Theses Full-text Database (electronic journal), vol. 03, Mar. 15, 2007, abstract.
Extended European search report, including the supplementary European search report and the European search opinion, for EP Patent Appl. No. 11753494.1, dated Jul. 9, 2013, The European Patent Office, Rijswijk, Netherlands.
Schäfer, T et al., "Enzymes for Technical Applications," in Biopolymers Online, (Jan. 15, 2005), DOI: 10.1002/3527600035. bpol7013, Wiley Online Library.
Ito, S, "Alkaline cellulase from alkaliphilic Bacillus: enzymatic properties, genetics, and applications to detergents," Extremophiles 1(2): 61-66, (May 1997), Springer-Verlag, Berlin, Germany.
International Search Report (ISR) for PCT/JP2011/055831, I.A. fd: Mar. 11, 2011, mailed Apr. 19, 2011 from the Japanese Patent Office, Tokyo, Japan.
International Preliminary Report on Patentability (IPRP), Chapter I of the Patent Cooperation Treaty, including the Written Opinion for PCT/JP2011/055831, I.A. fd: Mar. 11, 2011, issued Oct. 23, 2012, from the International Bureau of WIPO, Geneva, Switzerland.
Boraston, AB et al., "Identification and glucan-binding properties of a new carbohydrate-binding module family," Biochem J, Jan. 2002; 361(Pt 1): 35-40.
Ito, Susumu, "Alcali Koso wa Ikani Alcali Kankyo ni Tekio shite Kita noka," Bionics, Oct. 2005, vol. 2, No. 10, pp. 30-35, Japan.

\* cited by examiner

*Primary Examiner* — Iqbal H Chowdhury
(74) *Attorney, Agent, or Firm* — Sterne, Kessler, Goldstein & Fox P.L.L.C.

(57) ABSTRACT

The present invention provides a mutant alkaline cellulase having enhanced anti-redeposition ability. The present invention provides a mutant alkaline cellulase having an amino acid sequence in which at least amino acid residue selected from the amino acid residues at the positions corresponding to positions 58, 45, 52, 56, 60, 64, 66, 71, 103, 119, 122, 123, 124, 125, 127, 130, 140, 161, 164, 175, 176, 178, 179, 181, 193, 194, 195, 196, 197, 199, 202, 203, 217, 225, 227, 228, 251, 267, 272, 276, 277, 280, 282, 297, 310, 312, 318, 324, 345, 354, 356, 357, 360, 363, 368, 418, 419, 420, 421, 422, 453, 454, 455, 457, 458, 459, 494, 495, 496, 500, 501, 502, 503, 504, 550, 551, 552, 604, 605, 606, 607, 608, 640, 641, 642, 644, 645, 646, 683, 684, 685, 690, 691, 692, 693, 694, 739, 740, and 741 of the amino acid sequence of an alkaline cellulase set forth in SEQ ID NO: 2 or of the amino acid sequence of an alkaline cellulase having at least 70% identity with the amino acid sequence of SEQ ID NO: 2, is substituted with other amino acid residue.

11 Claims, 4 Drawing Sheets

A

B

A

B

SEQUENCE LISTING

```
<160> NUMBER OF SEQ ID NOS: 34

<210> SEQ ID NO 1
<211> LENGTH: 3150
<212> TYPE: DNA
<213> ORGANISM: Bacillus sp. KSM-S237
<220> FEATURE:
<221> NAME/KEY: CDS
<222> LOCATION: (573)..(3044)

<400> SEQUENCE: 1
gatttgccga tgcaacaggc ttatatttag aggaaatttc ttttaaatt gaatacggaa        60 taaaatcagg taaacaggtc ctgattttat tttttgagt tttttagaga actgaagatt      120
gaaataaaag tagaagacaa aggacataag aaaattgcat tagtttaat tatagaaaac      180 gcctttttat aattatttat acctagaacg aaaatactgt ttcgaaagcg gtttactata      240
aaaccttata ttccggctct ttttaaaac aggggggtaaa aattcactct agtattctaa      300
tttcaacatg ctataataaa tttgtaagac gcaatatgca tctctttttt tacgatatat      360
gtaagcggtt aaccttgtgc tatatgccga tttaggaagg ggggtagatt gagtcaagta      420
gtaataatat agataactta taagttgttg agaagcagga gagcatctgg gttactcaca      480 agtttttta aaactttaac gaaagcactt tcggtaatgc ttatgaattt agctatttga      540
```

| | | |
|---|---|---|
| ttcaattact ttaaaaatat ttaggaggta at atg atg tta aga aag aaa aca<br>                                                    Met Met Leu Arg Lys Lys Thr<br>                                                      1                   5 | 593 |
| aag cag ttg att tct tcc att ctt att tta gtt tta ctt cta tct tta<br>Lys Gln Leu Ile Ser Ser Ile Leu Ile Leu Val Leu Leu Leu Ser Leu<br>           10                    15                    20 | 641 |
| ttt ccg gca gct ctt gca gca gaa gga aac act cgt gaa gac aat ttt<br>Phe Pro Ala Ala Leu Ala Ala Glu Gly Asn Thr Arg Glu Asp Asn Phe<br>     25                    30                    35 | 689 |
| aaa cat tta tta ggt aat gac aat gtt aaa cgc cct tct gag gct ggc<br>Lys His Leu Leu Gly Asn Asp Asn Val Lys Arg Pro Ser Glu Ala Gly<br>40                    45                    50                   55 | 737 |
| gca tta caa tta caa gaa gtc gat gga caa atg aca tta gta gat caa<br>Ala Leu Gln Leu Gln Glu Val Asp Gly Gln Met Thr Leu Val Asp Gln<br>                    60                    65                    70 | 785 |
| cat gga gaa aaa att caa tta cgt gga atg agt aca cac gga tta cag<br>His Gly Glu Lys Ile Gln Leu Arg Gly Met Ser Thr His Gly Leu Gln<br>                      75                    80                    85 | 833 |
| tgg ttt cct gag atc ttg aat gat aac gca tac aaa gct ctt tct aac<br>Trp Phe Pro Glu Ile Leu Asn Asp Asn Ala Tyr Lys Ala Leu Ser Asn<br>           90                    95                    100 | 881 |
| gat tgg gat tcc aat atg att cgt ctt gct atg tat gta ggt gaa aat<br>Asp Trp Asp Ser Asn Met Ile Arg Leu Ala Met Tyr Val Gly Glu Asn<br>     105                   110                   115 | 929 |
| ggg tac gct aca aac cct gag tta atc aaa caa aga gtg att gat gga<br>Gly Tyr Ala Thr Asn Pro Glu Leu Ile Lys Gln Arg Val Ile Asp Gly<br>120                   125                   130                   135 | 977 |
| att gag tta gcg att gaa aat gac atg tat gtt att gtt gac tgg cat<br>Ile Glu Leu Ala Ile Glu Asn Asp Met Tyr Val Ile Val Asp Trp His<br>                   140                   145                   150 | 1025 |
| gtt cat gcg cca ggt gat cct aga gat cct gtt tat gca ggt gct aaa<br>Val His Ala Pro Gly Asp Pro Arg Asp Pro Val Tyr Ala Gly Ala Lys<br>                   155                   160                   165 | 1073 |
| gat ttc ttt aga gaa att gca gct tta tac cct aat aat cca cac att<br>Asp Phe Phe Arg Glu Ile Ala Ala Leu Tyr Pro Asn Asn Pro His Ile<br>           170                   175                   180 | 1121 |
| att tat gag tta gcg aat gag ccg agt agt aat aat aat ggt gga gca<br>Ile Tyr Glu Leu Ala Asn Glu Pro Ser Ser Asn Asn Asn Gly Gly Ala<br>     185                   190                   195 | 1169 |
| ggg att ccg aat aac gaa gaa ggt tgg aaa gcg gta aaa gaa tat gct<br>Gly Ile Pro Asn Asn Glu Glu Gly Trp Lys Ala Val Lys Glu Tyr Ala<br>200                   205                   210                   215 | 1217 |
| gat cca att gta gaa atg tta cgt aaa agc ggt aat gca gat gac aac<br>Asp Pro Ile Val Glu Met Leu Arg Lys Ser Gly Asn Ala Asp Asp Asn<br>                   220                   225                   230 | 1265 |
| att atc att gtt ggt agt cca aac tgg agt cag cgt ccg gac tta gca<br>Ile Ile Ile Val Gly Ser Pro Asn Trp Ser Gln Arg Pro Asp Leu Ala<br>                   235                   240                   245 | 1313 |
| gct gat aat cca att gat gat cac cat aca atg tat act gtt cac ttc<br>Ala Asp Asn Pro Ile Asp Asp His His Thr Met Tyr Thr Val His Phe<br>           250                   255                   260 | 1361 |
| tac act ggt tca cat gct gct tca act gaa agc tat ccg tct gaa act<br>Tyr Thr Gly Ser His Ala Ala Ser Thr Glu Ser Tyr Pro Ser Glu Thr<br>     265                   270                   275 | 1409 |
| cct aac tct gaa aga gga aac gta atg agt aac act cgt tat gcg tta<br>Pro Asn Ser Glu Arg Gly Asn Val Met Ser Asn Thr Arg Tyr Ala Leu<br>280                   285                   290                   295 | 1457 |
| gaa aac gga gta gcg gta ttt gca aca gag tgg gga acg agt caa gct<br>Glu Asn Gly Val Ala Val Phe Ala Thr Glu Trp Gly Thr Ser Gln Ala<br>                   300                   305                   310 | 1505 |

-continued

```
agt gga gac ggt ggt cct tac ttt gat gaa gca gat gta tgg att gaa    1553
Ser Gly Asp Gly Gly Pro Tyr Phe Asp Glu Ala Asp Val Trp Ile Glu
            315                 320                 325 ttt tta aat gaa aac aac att agc tgg gct aac tgg tct tta acg aat    1601
Phe Leu Asn Glu Asn Asn Ile Ser Trp Ala Asn Trp Ser Leu Thr Asn
        330                 335                 340 aaa aat gaa gta tct ggt gca ttt aca cca ttc gag tta ggt aag tct    1649
Lys Asn Glu Val Ser Gly Ala Phe Thr Pro Phe Glu Leu Gly Lys Ser
    345                 350                 355 aac gca acc aat ctt gac cca ggt cca gat cat gtg tgg gca cca gaa    1697
Asn Ala Thr Asn Leu Asp Pro Gly Pro Asp His Val Trp Ala Pro Glu
360                 365                 370                 375 gaa tta agt ctt tct gga gaa tat gta cgt gct cgt att aaa ggt gtg    1745
Glu Leu Ser Leu Ser Gly Glu Tyr Val Arg Ala Arg Ile Lys Gly Val
            380                 385                 390 aac tat gag cca atc gac cgt aca aaa tac acg aaa gta ctt tgg gac    1793
Asn Tyr Glu Pro Ile Asp Arg Thr Lys Tyr Thr Lys Val Leu Trp Asp
        395                 400                 405 ttt aat gat gga acg aag caa gga ttt gga gtg aat tcg gat tct cca    1841
Phe Asn Asp Gly Thr Lys Gln Gly Phe Gly Val Asn Ser Asp Ser Pro
    410                 415                 420 aat aaa gaa ctt att gca gtt gat aat gaa aac aac act ttg aaa gtt    1889
Asn Lys Glu Leu Ile Ala Val Asp Asn Glu Asn Asn Thr Leu Lys Val
425                 430                 435 tcg gga tta gat gta agt aac gat gtt tca gat ggc aac ttc tgg gct    1937
Ser Gly Leu Asp Val Ser Asn Asp Val Ser Asp Gly Asn Phe Trp Ala
440                 445                 450                 455 aat gct cgt ctt tct gcc aac ggt tgg gga aaa agt gtt gat att tta    1985
Asn Ala Arg Leu Ser Ala Asn Gly Trp Gly Lys Ser Val Asp Ile Leu
            460                 465                 470 ggt gct gag aag ctt aca atg gat gtt att gtt gat gaa cca acg acg    2033
Gly Ala Glu Lys Leu Thr Met Asp Val Ile Val Asp Glu Pro Thr Thr
        475                 480                 485 gta gct att gcg gcg att cca caa agt agt aaa agt gga tgg gca aat    2081
Val Ala Ile Ala Ala Ile Pro Gln Ser Ser Lys Ser Gly Trp Ala Asn
    490                 495                 500 cca gag cgt gct gtt cga gtg aac gcg gaa gat ttt gtc cag caa acg    2129
Pro Glu Arg Ala Val Arg Val Asn Ala Glu Asp Phe Val Gln Gln Thr
505                 510                 515 gac ggt aag tat aaa gct gga tta aca att aca gga gaa gat gct cct    2177
Asp Gly Lys Tyr Lys Ala Gly Leu Thr Ile Thr Gly Glu Asp Ala Pro
520                 525                 530                 535 aac cta aaa aat atc gct ttt cat gaa gaa gat aac aat atg aac aac    2225
Asn Leu Lys Asn Ile Ala Phe His Glu Glu Asp Asn Asn Met Asn Asn
            540                 545                 550 atc att ctg ttc gtg gga act gat gca gct gac gtt att tac tta gat    2273
Ile Ile Leu Phe Val Gly Thr Asp Ala Ala Asp Val Ile Tyr Leu Asp
        555                 560                 565 aac att aaa gta att gga aca gaa gtt gaa att cca gtt gtt cat gat    2321
Asn Ile Lys Val Ile Gly Thr Glu Val Glu Ile Pro Val Val His Asp
    570                 575                 580 cca aaa gga gaa gct gtt ctt cct tct gtt ttt gaa gac ggt aca cgt    2369
Pro Lys Gly Glu Ala Val Leu Pro Ser Val Phe Glu Asp Gly Thr Arg
585                 590                 595 caa ggt tgg gac tgg gct gga gag tct ggt gtg aaa aca gct tta aca    2417
Gln Gly Trp Asp Trp Ala Gly Glu Ser Gly Val Lys Thr Ala Leu Thr
600                 605                 610                 615 att gaa gaa gca aac ggt tct aac gcg tta tca tgg gaa ttt gga tat    2465
Ile Glu Glu Ala Asn Gly Ser Asn Ala Leu Ser Trp Glu Phe Gly Tyr
```

```
                    620                 625                 630
cca gaa gta aaa cct agt gat aac tgg gca aca gct cca cgt tta gat     2513
Pro Glu Val Lys Pro Ser Asp Asn Trp Ala Thr Ala Pro Arg Leu Asp
            635                 640                 645 ttc tgg aaa tct gac ttg gtt cgc ggt gag aat gat tat gta gct ttt     2561
Phe Trp Lys Ser Asp Leu Val Arg Gly Glu Asn Asp Tyr Val Ala Phe
            650                 655                 660 gat ttc tat cta gat cca gtt cgt gca aca gaa ggc gca atg aat atc     2609
Asp Phe Tyr Leu Asp Pro Val Arg Ala Thr Glu Gly Ala Met Asn Ile
            665                 670                 675 aat tta gta ttc cag cca cct act aac ggg tat tgg gta caa gca cca     2657
Asn Leu Val Phe Gln Pro Pro Thr Asn Gly Tyr Trp Val Gln Ala Pro
680                 685                 690                 695 aaa acg tat acg att aac ttt gat gaa tta gag gaa gcg aat caa gta     2705
Lys Thr Tyr Thr Ile Asn Phe Asp Glu Leu Glu Glu Ala Asn Gln Val
                700                 705                 710 aat ggt tta tat cac tat gaa gtg aaa att aac gta aga gat att aca     2753
Asn Gly Leu Tyr His Tyr Glu Val Lys Ile Asn Val Arg Asp Ile Thr
            715                 720                 725 aac att caa gat gac acg tta cta cgt aac atg atg atc att ttt gca     2801
Asn Ile Gln Asp Asp Thr Leu Leu Arg Asn Met Met Ile Ile Phe Ala
            730                 735                 740 gat gta gaa agt gac ttt gca ggg aga gtc ttt gta gat aat gtt cgt     2849
Asp Val Glu Ser Asp Phe Ala Gly Arg Val Phe Val Asp Asn Val Arg
745                 750                 755 ttt gag ggg gct gct act act gag ccg gtt gaa cca gag cca gtt gat     2897
Phe Glu Gly Ala Ala Thr Thr Glu Pro Val Glu Pro Glu Pro Val Asp
760                 765                 770                 775 cct ggc gaa gag acg cca cct gtc gat gag aag gaa gcg aaa aaa gaa     2945
Pro Gly Glu Glu Thr Pro Pro Val Asp Glu Lys Glu Ala Lys Lys Glu
                780                 785                 790 caa aaa gaa gca gag aaa gaa gag aaa gaa gca gta aaa gaa gaa aag     2993
Gln Lys Glu Ala Glu Lys Glu Glu Lys Glu Ala Val Lys Glu Glu Lys
            795                 800                 805 aaa gaa gct aaa gaa gaa aag aaa gca gtc aaa aat gag gct aag aaa     3041
Lys Glu Ala Lys Glu Glu Lys Lys Ala Val Lys Asn Glu Ala Lys Lys
            810                 815                 820 aaa taatctatta aactagttat agggttatct aaaggtctga tgtagatctt          3094
Lys ttagataacc ttttt cttgc ataactggac acagagttgt tattaaagaa agtaag      3150
```

<210> SEQ ID NO 2
<211> LENGTH: 824
<212> TYPE: PRT
<213> ORGANISM: Bacillus sp. KSM-S237

<400> SEQUENCE: 2

```
Met Met Leu Arg Lys Lys Thr Lys Gln Leu Ile Ser Ser Ile Leu Ile
1               5                   10                  15

Leu Val Leu Leu Leu Ser Leu Phe Pro Ala Ala Leu Ala Ala Glu Gly
                20                  25                  30

Asn Thr Arg Glu Asp Asn Phe Lys His Leu Leu Gly Asn Asp Asn Val
            35                  40                  45

Lys Arg Pro Ser Glu Ala Gly Ala Leu Gln Leu Gln Glu Val Asp Gly
        50                  55                  60

Gln Met Thr Leu Val Asp Gln His Gly Glu Lys Ile Gln Leu Arg Gly
65                  70                  75                  80

Met Ser Thr His Gly Leu Gln Trp Phe Pro Glu Ile Leu Asn Asp Asn
```

```
                        85                  90                  95
Ala Tyr Lys Ala Leu Ser Asn Asp Trp Asp Ser Asn Met Ile Arg Leu
            100                 105                 110

Ala Met Tyr Val Gly Glu Asn Gly Tyr Ala Thr Asn Pro Glu Leu Ile
            115                 120                 125

Lys Gln Arg Val Ile Asp Gly Ile Glu Leu Ala Ile Glu Asn Asp Met
        130                 135                 140

Tyr Val Ile Val Asp Trp His Val His Ala Pro Gly Asp Pro Arg Asp
145                 150                 155                 160

Pro Val Tyr Ala Gly Ala Lys Asp Phe Phe Arg Glu Ile Ala Ala Leu
                165                 170                 175

Tyr Pro Asn Asn Pro His Ile Ile Tyr Glu Leu Ala Asn Glu Pro Ser
            180                 185                 190

Ser Asn Asn Asn Gly Gly Ala Gly Ile Pro Asn Asn Glu Glu Gly Trp
        195                 200                 205

Lys Ala Val Lys Glu Tyr Ala Asp Pro Ile Val Glu Met Leu Arg Lys
        210                 215                 220

Ser Gly Asn Ala Asp Asp Asn Ile Ile Ile Val Gly Ser Pro Asn Trp
225                 230                 235                 240

Ser Gln Arg Pro Asp Leu Ala Ala Asp Asn Pro Ile Asp Asp His His
                245                 250                 255

Thr Met Tyr Thr Val His Phe Tyr Thr Gly Ser His Ala Ala Ser Thr
            260                 265                 270

Glu Ser Tyr Pro Ser Glu Thr Pro Asn Ser Glu Arg Gly Asn Val Met
        275                 280                 285

Ser Asn Thr Arg Tyr Ala Leu Glu Asn Gly Val Ala Val Phe Ala Thr
        290                 295                 300

Glu Trp Gly Thr Ser Gln Ala Ser Gly Asp Gly Pro Tyr Phe Asp
305                 310                 315                 320

Glu Ala Asp Val Trp Ile Glu Phe Leu Asn Glu Asn Asn Ile Ser Trp
                325                 330                 335

Ala Asn Trp Ser Leu Thr Asn Lys Asn Glu Val Ser Gly Ala Phe Thr
            340                 345                 350

Pro Phe Glu Leu Gly Lys Ser Asn Ala Thr Asn Leu Asp Pro Gly Pro
        355                 360                 365

Asp His Val Trp Ala Pro Glu Glu Leu Ser Leu Ser Gly Glu Tyr Val
        370                 375                 380

Arg Ala Arg Ile Lys Gly Val Asn Tyr Glu Pro Ile Asp Arg Thr Lys
385                 390                 395                 400

Tyr Thr Lys Val Leu Trp Asp Phe Asn Asp Gly Thr Lys Gln Gly Phe
                405                 410                 415

Gly Val Asn Ser Asp Ser Pro Asn Lys Glu Leu Ile Ala Val Asp Asn
            420                 425                 430

Glu Asn Asn Thr Leu Lys Val Ser Gly Leu Asp Val Ser Asn Asp Val
        435                 440                 445

Ser Asp Gly Asn Phe Trp Ala Asn Ala Arg Leu Ser Ala Asn Gly Trp
        450                 455                 460

Gly Lys Ser Val Asp Ile Leu Gly Ala Glu Lys Leu Thr Met Asp Val
465                 470                 475                 480

Ile Val Asp Glu Pro Thr Thr Val Ala Ile Ala Ala Ile Pro Gln Ser
                485                 490                 495

Ser Lys Ser Gly Trp Ala Asn Pro Glu Arg Ala Val Arg Val Asn Ala
            500                 505                 510
```

```
Glu Asp Phe Val Gln Gln Thr Asp Gly Lys Tyr Lys Ala Gly Leu Thr
            515                 520                 525
Ile Thr Gly Glu Asp Ala Pro Asn Leu Lys Asn Ile Ala Phe His Glu
        530                 535                 540
Glu Asp Asn Asn Met Asn Asn Ile Ile Leu Phe Val Gly Thr Asp Ala
545                 550                 555                 560
Ala Asp Val Ile Tyr Leu Asp Asn Ile Lys Val Ile Gly Thr Glu Val
                565                 570                 575
Glu Ile Pro Val Val His Asp Pro Lys Gly Glu Ala Val Leu Pro Ser
            580                 585                 590
Val Phe Glu Asp Gly Thr Arg Gln Gly Trp Asp Trp Ala Gly Glu Ser
        595                 600                 605
Gly Val Lys Thr Ala Leu Thr Ile Glu Ala Asn Gly Ser Asn Ala
610                 615                 620
Leu Ser Trp Glu Phe Gly Tyr Pro Glu Val Lys Pro Ser Asp Asn Trp
625                 630                 635                 640
Ala Thr Ala Pro Arg Leu Asp Phe Trp Lys Ser Asp Leu Val Arg Gly
                645                 650                 655
Glu Asn Asp Tyr Val Ala Phe Asp Phe Tyr Leu Asp Pro Val Arg Ala
            660                 665                 670
Thr Glu Gly Ala Met Asn Ile Asn Leu Val Phe Gln Pro Pro Thr Asn
        675                 680                 685
Gly Tyr Trp Val Gln Ala Pro Lys Thr Tyr Thr Ile Asn Phe Asp Glu
    690                 695                 700
Leu Glu Glu Ala Asn Gln Val Asn Gly Leu Tyr His Tyr Glu Val Lys
705                 710                 715                 720
Ile Asn Val Arg Asp Ile Thr Asn Ile Gln Asp Asp Thr Leu Leu Arg
                725                 730                 735
Asn Met Met Ile Ile Phe Ala Asp Val Glu Ser Asp Phe Ala Gly Arg
            740                 745                 750
Val Phe Val Asp Asn Val Arg Phe Glu Gly Ala Ala Thr Thr Glu Pro
        755                 760                 765
Val Glu Pro Glu Pro Val Asp Pro Gly Glu Glu Thr Pro Pro Val Asp
    770                 775                 780
Glu Lys Glu Ala Lys Lys Glu Gln Lys Glu Ala Glu Lys Glu Lys
785                 790                 795                 800
Glu Ala Val Lys Glu Glu Lys Lys Glu Ala Lys Glu Lys Lys Ala
                805                 810                 815
Val Lys Asn Glu Ala Lys Lys Lys
            820

<210> SEQ ID NO 3
<211> LENGTH: 2322
<212> TYPE: DNA
<213> ORGANISM: Bacillus sp. strain DSM12648
<220> FEATURE:
<221> NAME/KEY: CDS
<222> LOCATION: (1)..(2319)

<400> SEQUENCE: 3 gca gaa gga aac act cgt gaa gac aat ttt aaa cat tta tta ggt aat      48
Ala Glu Gly Asn Thr Arg Glu Asp Asn Phe Lys His Leu Leu Gly Asn
1               5                   10                  15 gac aat gtt aaa cgc cct tct gag gct ggc gca tta caa tta caa gaa     96
Asp Asn Val Lys Arg Pro Ser Glu Ala Gly Ala Leu Gln Leu Gln Glu
                20                  25                  30
```

```
gtc gat gga caa atg aca tta gta gat caa cat gga gaa aaa att caa      144
Val Asp Gly Gln Met Thr Leu Val Asp Gln His Gly Glu Lys Ile Gln
         35                  40                  45 tta cgt gga atg agt aca cac gga tta caa tgg ttt cct gar atc ttg      192
Leu Arg Gly Met Ser Thr His Gly Leu Gln Trp Phe Pro Glu Ile Leu
 50                  55                  60 aat gat aac gca tac aaa gct ctt gct aac gat tgg gaa tca aat atg      240
Asn Asp Asn Ala Tyr Lys Ala Leu Ala Asn Asp Trp Glu Ser Asn Met
65                   70                  75                  80 att cgt cta gct atg tat gtc ggt gaa aat ggc tat gct tca aat cca      288
Ile Arg Leu Ala Met Tyr Val Gly Glu Asn Gly Tyr Ala Ser Asn Pro
                 85                  90                  95 gag tta att aaa agc aga gtc att aaa gga ata gat ctt gct att gaa      336
Glu Leu Ile Lys Ser Arg Val Ile Lys Gly Ile Asp Leu Ala Ile Glu
            100                 105                 110 aat gac atg tat gtt att gtt gat tgg cat gta cat gca cct ggt gat      384
Asn Asp Met Tyr Val Ile Val Asp Trp His Val His Ala Pro Gly Asp
        115                 120                 125 cct aga gat ccc gtt tac gct gga gca gaa gat ttc ttt aga gat att      432
Pro Arg Asp Pro Val Tyr Ala Gly Ala Glu Asp Phe Phe Arg Asp Ile
130                 135                 140 gca gca tta tat cct aac aat cca cac att att tat gag tta gcg aat      480
Ala Ala Leu Tyr Pro Asn Asn Pro His Ile Ile Tyr Glu Leu Ala Asn
145                 150                 155                 160 gag cca agt agt aac aat aat ggt gga gct ggg att cca aat aat gaa      528
Glu Pro Ser Ser Asn Asn Asn Gly Gly Ala Gly Ile Pro Asn Asn Glu
                165                 170                 175 gaa ggt tgg aat gcg gta aaa gaa tac gct gat cca att gta gaa atg      576
Glu Gly Trp Asn Ala Val Lys Glu Tyr Ala Asp Pro Ile Val Glu Met
            180                 185                 190 tta cgt gat agc ggg aac gca gat gac aat atc atc att gtg ggt agt      624
Leu Arg Asp Ser Gly Asn Ala Asp Asp Asn Ile Ile Ile Val Gly Ser
        195                 200                 205 cca aac tgg agt cag cgt cct gac tta gca gct gat aat cca att aat      672
Pro Asn Trp Ser Gln Arg Pro Asp Leu Ala Ala Asp Asn Pro Ile Asn
210                 215                 220 gat cac cat aca atg tat act gtt cac ttc tac act ggt tca cat gct      720
Asp His His Thr Met Tyr Thr Val His Phe Tyr Thr Gly Ser His Ala
225                 230                 235                 240 gct tca act gag agc tat ccg cct gaa act cct aac tct gaa aga gga      768
Ala Ser Thr Glu Ser Tyr Pro Pro Glu Thr Pro Asn Ser Glu Arg Gly
                245                 250                 255 aac gta atg agt aac act cgt tat gcg tta gaa aac gga gta gcg gta      816
Asn Val Met Ser Asn Thr Arg Tyr Ala Leu Glu Asn Gly Val Ala Val
            260                 265                 270 ttt gcg aca gaa tgg gga aca agt caa gca aat gga gat ggt ggt cct      864
Phe Ala Thr Glu Trp Gly Thr Ser Gln Ala Asn Gly Asp Gly Gly Pro
        275                 280                 285 tat ttt gat gaa gca gat gta tgg att gag ttt tta aat gaa aac aac      912
Tyr Phe Asp Glu Ala Asp Val Trp Ile Glu Phe Leu Asn Glu Asn Asn
290                 295                 300 att agt tgg gct aac tgg tct tta acg aat aaa aat gaa gtg tct ggt      960
Ile Ser Trp Ala Asn Trp Ser Leu Thr Asn Lys Asn Glu Val Ser Gly
305                 310                 315                 320 gca ttt aca cca ttc gag tta ggt aag tct aac gca acc aat ctt gac     1008
Ala Phe Thr Pro Phe Glu Leu Gly Lys Ser Asn Ala Thr Asn Leu Asp
                325                 330                 335 cca ggt cca gat cat gtg tgg gca cca gaa gag tta agt ctt tcg gga     1056
Pro Gly Pro Asp His Val Trp Ala Pro Glu Glu Leu Ser Leu Ser Gly
```

-continued

```
                340              345              350
gaa tat gta cgt gct cgt att aaa ggt gtg aac tat gag cca atc gac       1104
Glu Tyr Val Arg Ala Arg Ile Lys Gly Val Asn Tyr Glu Pro Ile Asp
        355              360              365 cgt aca aaa tac acg aaa gta ctt tgg gac ttt aat gat gga acg aag       1152
Arg Thr Lys Tyr Thr Lys Val Leu Trp Asp Phe Asn Asp Gly Thr Lys
370             375              380 caa gga ttt gga gtg aat tcg gat tct cca aat aaa gaa ctt att gca       1200
Gln Gly Phe Gly Val Asn Ser Asp Ser Pro Asn Lys Glu Leu Ile Ala
385             390              395              400 gtt gat aat gaa aac aac act ttg aaa gtt tcg gga tta gat gta agt       1248
Val Asp Asn Glu Asn Asn Thr Leu Lys Val Ser Gly Leu Asp Val Ser
                405              410              415 aac gat gtt tca gat ggc aac ttc tgg gct aat gct cgt ctt tct gcc       1296
Asn Asp Val Ser Asp Gly Asn Phe Trp Ala Asn Ala Arg Leu Ser Ala
            420              425              430 gac ggt tgg gga aaa agt gtt gat att tta ggt gct gag aag ctt aca       1344
Asp Gly Trp Gly Lys Ser Val Asp Ile Leu Gly Ala Glu Lys Leu Thr
        435              440              445 atg gat gtt att gtt gat gaa cca acg acg gta gct att gcg gcg att       1392
Met Asp Val Ile Val Asp Glu Pro Thr Thr Val Ala Ile Ala Ala Ile
450             455              460 cca caa agt agt aaa agt gga tgg gca aat cca gag cgt gct gtt cga       1440
Pro Gln Ser Ser Lys Ser Gly Trp Ala Asn Pro Glu Arg Ala Val Arg
465             470              475              480 gtg aac gcg gaa gat ttt gtt cag caa acg gac ggt aag tat aaa gct       1488
Val Asn Ala Glu Asp Phe Val Gln Gln Thr Asp Gly Lys Tyr Lys Ala
                485              490              495 gga tta aca att aca gga gaa gat gct cct aac cta aaa aat atc gct       1536
Gly Leu Thr Ile Thr Gly Glu Asp Ala Pro Asn Leu Lys Asn Ile Ala
            500              505              510 ttt cat gaa gaa gat aac aat atg aac aac atc att ctg ttc gtg gga       1584
Phe His Glu Glu Asp Asn Asn Met Asn Asn Ile Ile Leu Phe Val Gly
        515              520              525 act gat gca gct gac gtt att tac tta gat aac att aaa gta att gga       1632
Thr Asp Ala Ala Asp Val Ile Tyr Leu Asp Asn Ile Lys Val Ile Gly
530             535              540 aca gaa gtt gaa att cca gtt gtt cat gat cca aaa gga gaa gct gtt       1680
Thr Glu Val Glu Ile Pro Val Val His Asp Pro Lys Gly Glu Ala Val
545             550              555              560 ctt cct tct gtt ttt gaa gac ggt aca cgt caa ggt tgg gac tgg gct       1728
Leu Pro Ser Val Phe Glu Asp Gly Thr Arg Gln Gly Trp Asp Trp Ala
                565              570              575 gga gag tct ggt gtg aaa aca gct tta aca att gaa gaa gca aac ggt       1776
Gly Glu Ser Gly Val Lys Thr Ala Leu Thr Ile Glu Glu Ala Asn Gly
            580              585              590 tct aac gcg tta tca tgg gaa ttt gga tat cca gaa gta aaa cct agt       1824
Ser Asn Ala Leu Ser Trp Glu Phe Gly Tyr Pro Glu Val Lys Pro Ser
        595              600              605 gat aac tgg gca aca gct cca cgt tta gat ttc tgg aaa tct gac ttg       1872
Asp Asn Trp Ala Thr Ala Pro Arg Leu Asp Phe Trp Lys Ser Asp Leu
610             615              620 gtt cgc ggt gag aat gat tat gta gct ttt gat ttc tat cta gat cca       1920
Val Arg Gly Glu Asn Asp Tyr Val Ala Phe Asp Phe Tyr Leu Asp Pro
625             630              635              640 gtt cgt gca aca gaa ggc gca atg aat atc aat tta gta ttc cag cca       1968
Val Arg Ala Thr Glu Gly Ala Met Asn Ile Asn Leu Val Phe Gln Pro
                645              650              655 cct act aac ggg tat tgg gta caa gca cca aaa acg tat acg att aac       2016
```

-continued

```
            Pro Thr Asn Gly Tyr Trp Val Gln Ala Pro Lys Thr Tyr Thr Ile Asn
                            660                 665                 670 ttt gat gaa tta gag gaa gcg aat caa gta aat ggt tta tat cac tat          2064
Phe Asp Glu Leu Glu Glu Ala Asn Gln Val Asn Gly Leu Tyr His Tyr
                675                 680                 685 gaa gtg aaa att aac gta aga gat att aca aac att caa gat gac acg          2112
Glu Val Lys Ile Asn Val Arg Asp Ile Thr Asn Ile Gln Asp Asp Thr
    690                 695                 700 tta cta cgt aac atg atg atc att ttt gca gat gta gaa agt gac ttt          2160
Leu Leu Arg Asn Met Met Ile Ile Phe Ala Asp Val Glu Ser Asp Phe
705                 710                 715                 720 gca ggg aga gtc ttt gta gat aat gtt cgt ttt gag ggg gct gct act          2208
Ala Gly Arg Val Phe Val Asp Asn Val Arg Phe Glu Gly Ala Ala Thr
                725                 730                 735 act gag ccg gtt gaa cca gag cca gtt gat cct ggc gaa gag acg cca          2256
Thr Glu Pro Val Glu Pro Glu Pro Val Asp Pro Gly Glu Glu Thr Pro
                740                 745                 750 cct gtc gat gag aag gaa gcg aaa aaa gaa caa aaa gaa gca gag aaa          2304
Pro Val Asp Glu Lys Glu Ala Lys Lys Glu Gln Lys Glu Ala Glu Lys
            755                 760                 765 gaa gag aaa gaa gag taa                                                  2322
Glu Glu Lys Glu Glu
    770

<210> SEQ ID NO 4
<211> LENGTH: 773
<212> TYPE: PRT
<213> ORGANISM: Bacillus sp. strain DSM12648

<400> SEQUENCE: 4

Ala Glu Gly Asn Thr Arg Glu Asp Asn Phe Lys His Leu Leu Gly Asn
1               5                   10                  15

Asp Asn Val Lys Arg Pro Ser Glu Ala Gly Ala Leu Gln Leu Gln Glu
            20                  25                  30

Val Asp Gly Gln Met Thr Leu Val Asp Gln His Gly Glu Lys Ile Gln
        35                  40                  45

Leu Arg Gly Met Ser Thr His Gly Leu Gln Trp Phe Pro Glu Ile Leu
    50                  55                  60

Asn Asp Asn Ala Tyr Lys Ala Leu Ala Asn Asp Trp Glu Ser Asn Met
65                  70                  75                  80

Ile Arg Leu Ala Met Tyr Val Gly Glu Asn Gly Tyr Ala Ser Asn Pro
                85                  90                  95

Glu Leu Ile Lys Ser Arg Val Ile Lys Gly Ile Asp Leu Ala Ile Glu
            100                 105                 110

Asn Asp Met Tyr Val Ile Val Asp Trp His Val His Ala Pro Gly Asp
        115                 120                 125

Pro Arg Asp Pro Val Tyr Ala Gly Ala Glu Asp Phe Phe Arg Asp Ile
    130                 135                 140

Ala Ala Leu Tyr Pro Asn Asn Pro His Ile Ile Tyr Glu Leu Ala Asn
145                 150                 155                 160

Glu Pro Ser Ser Asn Asn Asn Gly Gly Ala Gly Ile Pro Asn Asn Glu
                165                 170                 175

Glu Gly Trp Asn Ala Val Lys Glu Tyr Ala Asp Pro Ile Val Glu Met
            180                 185                 190

Leu Arg Asp Ser Gly Asn Ala Asp Asp Asn Ile Ile Ile Val Gly Ser
        195                 200                 205

Pro Asn Trp Ser Gln Arg Pro Asp Leu Ala Ala Asp Asn Pro Ile Asn
```

```
            210                 215                 220
Asp His His Thr Met Tyr Thr Val His Phe Tyr Thr Gly Ser His Ala
225                 230                 235                 240

Ala Ser Thr Glu Ser Tyr Pro Pro Glu Thr Pro Asn Ser Glu Arg Gly
                245                 250                 255

Asn Val Met Ser Asn Thr Arg Tyr Ala Leu Glu Asn Gly Val Ala Val
                260                 265                 270

Phe Ala Thr Glu Trp Gly Thr Ser Gln Ala Asn Gly Asp Gly Gly Pro
            275                 280                 285

Tyr Phe Asp Glu Ala Asp Val Trp Ile Glu Phe Leu Asn Glu Asn Asn
        290                 295                 300

Ile Ser Trp Ala Asn Trp Ser Leu Thr Asn Lys Asn Glu Val Ser Gly
305                 310                 315                 320

Ala Phe Thr Pro Phe Glu Leu Gly Lys Ser Asn Ala Thr Asn Leu Asp
                325                 330                 335

Pro Gly Pro Asp His Val Trp Ala Pro Glu Glu Leu Ser Leu Ser Gly
                340                 345                 350

Glu Tyr Val Arg Ala Arg Ile Lys Gly Val Asn Tyr Glu Pro Ile Asp
            355                 360                 365

Arg Thr Lys Tyr Thr Lys Val Leu Trp Asp Phe Asn Asp Gly Thr Lys
        370                 375                 380

Gln Gly Phe Gly Val Asn Ser Asp Ser Pro Asn Lys Glu Leu Ile Ala
385                 390                 395                 400

Val Asp Asn Glu Asn Asn Thr Leu Lys Val Ser Gly Leu Asp Val Ser
                405                 410                 415

Asn Asp Val Ser Asp Gly Asn Phe Trp Ala Asn Ala Arg Leu Ser Ala
                420                 425                 430

Asp Gly Trp Gly Lys Ser Val Asp Ile Leu Gly Ala Glu Lys Leu Thr
            435                 440                 445

Met Asp Val Ile Val Asp Glu Pro Thr Thr Val Ala Ile Ala Ala Ile
450                 455                 460

Pro Gln Ser Ser Lys Ser Gly Trp Ala Asn Pro Glu Arg Ala Val Arg
465                 470                 475                 480

Val Asn Ala Glu Asp Phe Val Gln Gln Thr Asp Gly Lys Tyr Lys Ala
                485                 490                 495

Gly Leu Thr Ile Thr Gly Glu Asp Ala Pro Asn Leu Lys Asn Ile Ala
                500                 505                 510

Phe His Glu Glu Asp Asn Asn Met Asn Asn Ile Ile Leu Phe Val Gly
            515                 520                 525

Thr Asp Ala Ala Asp Val Ile Tyr Leu Asp Asn Ile Lys Val Ile Gly
        530                 535                 540

Thr Glu Val Glu Ile Pro Val Val His Asp Pro Lys Gly Glu Ala Val
545                 550                 555                 560

Leu Pro Ser Val Phe Glu Asp Gly Thr Arg Gln Gly Trp Asp Trp Ala
                565                 570                 575

Gly Glu Ser Gly Val Lys Thr Ala Leu Thr Ile Glu Glu Ala Asn Gly
                580                 585                 590

Ser Asn Ala Leu Ser Trp Glu Phe Gly Tyr Pro Glu Val Lys Pro Ser
            595                 600                 605

Asp Asn Trp Ala Thr Ala Pro Arg Leu Asp Phe Trp Lys Ser Asp Leu
        610                 615                 620

Val Arg Gly Glu Asn Asp Tyr Val Ala Phe Asp Phe Tyr Leu Asp Pro
625                 630                 635                 640
```

Val Arg Ala Thr Glu Gly Ala Met Asn Ile Asn Leu Val Phe Gln Pro
            645                 650                 655

Pro Thr Asn Gly Tyr Trp Val Gln Ala Pro Lys Thr Tyr Thr Ile Asn
            660                 665                 670

Phe Asp Glu Leu Glu Glu Ala Asn Gln Val Asn Gly Leu Tyr His Tyr
            675                 680                 685

Glu Val Lys Ile Asn Val Arg Asp Ile Thr Asn Ile Gln Asp Asp Thr
690                 695                 700

Leu Leu Arg Asn Met Met Ile Ile Phe Ala Asp Val Glu Ser Asp Phe
705                 710                 715                 720

Ala Gly Arg Val Phe Val Asp Asn Val Arg Phe Glu Gly Ala Ala Thr
                725                 730                 735

Thr Glu Pro Val Glu Pro Glu Pro Val Asp Pro Gly Glu Glu Thr Pro
            740                 745                 750

Pro Val Asp Glu Lys Glu Ala Lys Lys Glu Gln Lys Glu Ala Glu Lys
            755                 760                 765

Glu Glu Lys Glu Glu
    770

<210> SEQ ID NO 5
<211> LENGTH: 2923
<212> TYPE: DNA
<213> ORGANISM: Bacillus sp. strain 1139
<220> FEATURE:
<221> NAME/KEY: CDS
<222> LOCATION: (203)..(2602)

<400> SEQUENCE: 5

```
gttaaccttg tgctatatgc cgatttagga aggggtagaa ttgagtcaag tagtcataat      60
ttagataact tataagttgt tgagaagcag gagagaatct gggttactca caagtttttt    120
aaaacattat cgaaagcact ttcggttatg cttatgaatt tagctatttg attcaattac    180
tttaataatt ttaggaggta at atg atg tta aga aag aaa aca aag cag ttg     232
                         Met Met Leu Arg Lys Lys Thr Lys Gln Leu
                           1               5                  10
``` att tct tcc att ctt att tta gtt tta ctt cta tct tta ttt ccg aca    280
Ile Ser Ser Ile Leu Ile Leu Val Leu Leu Leu Ser Leu Phe Pro Thr
                15                  20                  25 gct ctt gca gca gaa gga aac act cgt gaa gac aat ttt aaa cat tta    328
Ala Leu Ala Ala Glu Gly Asn Thr Arg Glu Asp Asn Phe Lys His Leu
        30                  35                  40 tta ggt aat gac aat gtt aaa cgc cct tct gag gct ggc gca tta caa    376
Leu Gly Asn Asp Asn Val Lys Arg Pro Ser Glu Ala Gly Ala Leu Gln
    45                  50                  55 tta caa gaa gtc gat gga caa atg aca tta gta gat caa cat gga gaa    424
Leu Gln Glu Val Asp Gly Gln Met Thr Leu Val Asp Gln His Gly Glu
60                  65                  70 aaa att caa tta cgt gga atg agt aca cac gga tta caa tgg ttt cct    472
Lys Ile Gln Leu Arg Gly Met Ser Thr His Gly Leu Gln Trp Phe Pro
75                  80                  85                  90 gag atc ttg aat gat aac gca tac aaa gct ctt gct aac gat tgg gaa    520
Glu Ile Leu Asn Asp Asn Ala Tyr Lys Ala Leu Ala Asn Asp Trp Glu
                95                 100                 105 tca aat atg att cgt cta gct atg tat gtc ggt gaa aat ggc tat gct    568
Ser Asn Met Ile Arg Leu Ala Met Tyr Val Gly Glu Asn Gly Tyr Ala
            110                 115                 120 tca aat cca gag tta att aaa agc aga gtc att aaa gga ata gat ctt    616
Ser Asn Pro Glu Leu Ile Lys Ser Arg Val Ile Lys Gly Ile Asp Leu -continued

```
             125                 130                 135
gct att gaa aat gac atg tat gtc atc gtt gat tgg cat gta cat gca    664
Ala Ile Glu Asn Asp Met Tyr Val Ile Val Asp Trp His Val His Ala
    140                 145                 150 cct ggt gat cct aga gat ccc gtt tac gct gga gca gaa gat ttc ttt    712
Pro Gly Asp Pro Arg Asp Pro Val Tyr Ala Gly Ala Glu Asp Phe Phe
155                 160                 165                 170 aga gat att gca gca tta tat cct aac aat cca cac att att tat gag    760
Arg Asp Ile Ala Ala Leu Tyr Pro Asn Asn Pro His Ile Ile Tyr Glu
                175                 180                 185 tta gcg aat gag cca agt agt aac aat aat ggt gga gct ggg att cca    808
Leu Ala Asn Glu Pro Ser Ser Asn Asn Asn Gly Gly Ala Gly Ile Pro
            190                 195                 200 aat aat gaa gaa ggt tgg aat gcg gta aaa gaa tac gct gat cca att    856
Asn Asn Glu Glu Gly Trp Asn Ala Val Lys Glu Tyr Ala Asp Pro Ile
        205                 210                 215 gta gaa atg tta cgt gat agc ggg aac gca gat gac aat att atc att    904
Val Glu Met Leu Arg Asp Ser Gly Asn Ala Asp Asp Asn Ile Ile Ile
    220                 225                 230 gtg ggt agt cca aac tgg agt cag cgt cct gac tta gca gct gat aat    952
Val Gly Ser Pro Asn Trp Ser Gln Arg Pro Asp Leu Ala Ala Asp Asn
235                 240                 245                 250 cca att gat gat cac cat aca atg tat act gtt cac ttc tac act ggt   1000
Pro Ile Asp Asp His His Thr Met Tyr Thr Val His Phe Tyr Thr Gly
                255                 260                 265 tca cat gct gct tca act gaa agc tat ccg cct gaa act cct aac tct   1048
Ser His Ala Ala Ser Thr Glu Ser Tyr Pro Pro Glu Thr Pro Asn Ser
            270                 275                 280 gaa aga gga aac gta atg agt aac act cgt tat gcg tta gaa aac gga   1096
Glu Arg Gly Asn Val Met Ser Asn Thr Arg Tyr Ala Leu Glu Asn Gly
        285                 290                 295 gta gca gta ttt gca aca gag tgg gga act agc caa gca aat gga gat   1144
Val Ala Val Phe Ala Thr Glu Trp Gly Thr Ser Gln Ala Asn Gly Asp
    300                 305                 310 ggt ggt cct tac ttt gat gaa gca gat gta tgg att gag ttt tta aat   1192
Gly Gly Pro Tyr Phe Asp Glu Ala Asp Val Trp Ile Glu Phe Leu Asn
315                 320                 325                 330 gaa aac aac att agc tgg gct aac tgg tct tta acg aat aaa aat gaa   1240
Glu Asn Asn Ile Ser Trp Ala Asn Trp Ser Leu Thr Asn Lys Asn Glu
                335                 340                 345 gta tct ggt gca ttt aca cca ttc gag tta ggt aag tct aac gca aca   1288
Val Ser Gly Ala Phe Thr Pro Phe Glu Leu Gly Lys Ser Asn Ala Thr
            350                 355                 360 agt ctt gac cca ggg cca gac caa gta tgg gta cca gaa gag tta agt   1336
Ser Leu Asp Pro Gly Pro Asp Gln Val Trp Val Pro Glu Glu Leu Ser
        365                 370                 375 ctt tct gga gaa tat gta cgt gct cgt att aaa ggt gtg aac tat gag   1384
Leu Ser Gly Glu Tyr Val Arg Ala Arg Ile Lys Gly Val Asn Tyr Glu
    380                 385                 390 cca atc gac cgt aca aaa tac acg aaa gta ctt tgg gac ttt aat gat   1432
Pro Ile Asp Arg Thr Lys Tyr Thr Lys Val Leu Trp Asp Phe Asn Asp
395                 400                 405                 410 gga acg aag caa gga ttt gga gtg aat gga gat tct cca gtt gaa gat   1480
Gly Thr Lys Gln Gly Phe Gly Val Asn Gly Asp Ser Pro Val Glu Asp
                415                 420                 425 gta gtt att gag aat gaa gcg ggc gct tta aaa ctt tca gga tta gat   1528
Val Val Ile Glu Asn Glu Ala Gly Ala Leu Lys Leu Ser Gly Leu Asp
            430                 435                 440 gca agt aat gat gtt tct gaa ggt aat tac tgg gct aat gct cgt ctt   1576
```

```
                                                                -continued

Ala Ser Asn Asp Val Ser Glu Gly Asn Tyr Trp Ala Asn Ala Arg Leu
        445                 450                 455 tct gcc gac ggt tgg gga aaa agt gtt gat att tta ggt gct gaa aaa    1624
Ser Ala Asp Gly Trp Gly Lys Ser Val Asp Ile Leu Gly Ala Glu Lys
460                 465                 470 ctt act atg gat gtg att gtt gat gag ccg acc acg gta tca att gct    1672
Leu Thr Met Asp Val Ile Val Asp Glu Pro Thr Thr Val Ser Ile Ala
475                 480                 485                 490 gca att cca caa ggg cca tca gcc aat tgg gtt aat cca aat cgt gca    1720
Ala Ile Pro Gln Gly Pro Ser Ala Asn Trp Val Asn Pro Asn Arg Ala
                495                 500                 505 att aag gtt gag cca act aat ttc gta ccg tta gag gat aag ttt aaa    1768
Ile Lys Val Glu Pro Thr Asn Phe Val Pro Leu Glu Asp Lys Phe Lys
        510                 515                 520 gcg gaa tta act ata act tca gct gac tct cca tcg tta gaa gct att    1816
Ala Glu Leu Thr Ile Thr Ser Ala Asp Ser Pro Ser Leu Glu Ala Ile
    525                 530                 535 gcg atg cat gct gaa aat aac aac atc aac aac atc att ctt ttt gta    1864
Ala Met His Ala Glu Asn Asn Asn Ile Asn Asn Ile Ile Leu Phe Val
540                 545                 550 gga act gaa ggt gct gat gtt atc tat tta gat aac att aaa gta att    1912
Gly Thr Glu Gly Ala Asp Val Ile Tyr Leu Asp Asn Ile Lys Val Ile
555                 560                 565                 570 gga aca gaa gtt gaa att cca gtt gtt cat gat cca aaa gga gaa gct    1960
Gly Thr Glu Val Glu Ile Pro Val Val His Asp Pro Lys Gly Glu Ala
                575                 580                 585 gtt ctt cct tct gtt ttt gaa gac ggt aca cgt caa ggt tgg gac tgg    2008
Val Leu Pro Ser Val Phe Glu Asp Gly Thr Arg Gln Gly Trp Asp Trp
        590                 595                 600 gct gga gag tct ggt gtg aaa aca gct tta aca att gaa gaa gca aac    2056
Ala Gly Glu Ser Gly Val Lys Thr Ala Leu Thr Ile Glu Glu Ala Asn
    605                 610                 615 ggt tct aac gcg tta tca tgg gaa ttt gga tac cca gaa gta aaa cct    2104
Gly Ser Asn Ala Leu Ser Trp Glu Phe Gly Tyr Pro Glu Val Lys Pro
620                 625                 630 agt gat aac tgg gca aca gct cca cgt tta gat ttc tgg aaa tct gac    2152
Ser Asp Asn Trp Ala Thr Ala Pro Arg Leu Asp Phe Trp Lys Ser Asp
635                 640                 645                 650 ttg gtt cgc ggt gaa aat gat tat gta act ttt gat ttc tat cta gat    2200
Leu Val Arg Gly Glu Asn Asp Tyr Val Thr Phe Asp Phe Tyr Leu Asp
                655                 660                 665 cca gtt cgt gca aca gaa ggc gca atg aat atc aat tta gta ttc cag    2248
Pro Val Arg Ala Thr Glu Gly Ala Met Asn Ile Asn Leu Val Phe Gln
        670                 675                 680 cca cct act aac ggg tat tgg gta caa gca cca aaa acg tat acg att    2296
Pro Pro Thr Asn Gly Tyr Trp Val Gln Ala Pro Lys Thr Tyr Thr Ile
    685                 690                 695 aac ttt gat gaa tta gag gaa ccg aat caa gta aat ggt tta tat cac    2344
Asn Phe Asp Glu Leu Glu Glu Pro Asn Gln Val Asn Gly Leu Tyr His
700                 705                 710 tat gaa gtg aaa att aac gta aga gat att aca aac att caa gat gac    2392
Tyr Glu Val Lys Ile Asn Val Arg Asp Ile Thr Asn Ile Gln Asp Asp
715                 720                 725                 730 acg tta cta cgt aac atg atg atc att ttt gca gat gta gaa agt gac    2440
Thr Leu Leu Arg Asn Met Met Ile Ile Phe Ala Asp Val Glu Ser Asp
                735                 740                 745 ttt gca ggg aga gtc ttt gta gat aat gtt cgt ttt gag ggg gct gct    2488
Phe Ala Gly Arg Val Phe Val Asp Asn Val Arg Phe Glu Gly Ala Ala
        750                 755                 760
```

-continued

```
act act gag ccg gtt gaa cca gag cca gtt gat cct ggc gaa gag acg    2536
Thr Thr Glu Pro Val Glu Pro Glu Pro Val Asp Pro Gly Glu Glu Thr
            765                 770                 775 ccg cct gtc gat gag aag gaa gcg aaa aca gaa caa aaa gaa gca gag    2584
Pro Pro Val Asp Glu Lys Glu Ala Lys Thr Glu Gln Lys Glu Ala Glu
780                 785                 790 aaa gaa gag aaa gaa gag taaaagaaga aagaaagaa gctaaagaag            2632
Lys Glu Glu Lys Glu Glu
795                 800 aaagaaagc aatcaaaaat gaggctacga aaaataatc taataaacta gttataggt     2692 tatctaaagg tctgatgcag atctttaga taaccttttt ttgcataact ggacatagaa   2752
tggttattaa agaaagcacg gtgtttatac gatattaaaa ggtagcgatt ttaattgaaa  2812
cctttaataa tgtcgtgtga tagaatgatg aagtaattta agaggggga aacgaagtga   2872 aaacggaaat ttctagtaca acaaaaacag accaacaaat actgcaagct t           2923
```

<210> SEQ ID NO 6
<211> LENGTH: 800
<212> TYPE: PRT
<213> ORGANISM: Bacillus sp. strain 1139

<400> SEQUENCE: 6

```
Met Met Leu Arg Lys Lys Thr Lys Gln Leu Ile Ser Ser Ile Leu Ile
1               5                   10                  15

Leu Val Leu Leu Leu Ser Leu Phe Pro Thr Ala Leu Ala Ala Glu Gly
            20                  25                  30

Asn Thr Arg Glu Asp Asn Phe Lys His Leu Leu Gly Asn Asp Asn Val
        35                  40                  45

Lys Arg Pro Ser Glu Ala Gly Ala Leu Gln Leu Gln Glu Val Asp Gly
    50                  55                  60

Gln Met Thr Leu Val Asp Gln His Gly Glu Lys Ile Gln Leu Arg Gly
65                  70                  75                  80

Met Ser Thr His Gly Leu Gln Trp Phe Pro Glu Ile Leu Asn Asp Asn
                85                  90                  95

Ala Tyr Lys Ala Leu Ala Asn Asp Trp Glu Ser Asn Met Ile Arg Leu
            100                 105                 110

Ala Met Tyr Val Gly Glu Asn Gly Tyr Ala Ser Asn Pro Glu Leu Ile
        115                 120                 125

Lys Ser Arg Val Ile Lys Gly Ile Asp Leu Ala Ile Glu Asn Asp Met
    130                 135                 140

Tyr Val Ile Val Asp Trp His Val His Ala Pro Gly Asp Pro Arg Asp
145                 150                 155                 160

Pro Val Tyr Ala Gly Ala Glu Asp Phe Phe Arg Asp Ile Ala Ala Leu
                165                 170                 175

Tyr Pro Asn Asn Pro His Ile Ile Tyr Glu Leu Ala Asn Glu Pro Ser
            180                 185                 190

Ser Asn Asn Asn Gly Gly Ala Gly Ile Pro Asn Asn Glu Glu Gly Trp
        195                 200                 205

Asn Ala Val Lys Glu Tyr Ala Asp Pro Ile Val Glu Met Leu Arg Asp
    210                 215                 220

Ser Gly Asn Ala Asp Asp Asn Ile Ile Ile Val Gly Ser Pro Asn Trp
225                 230                 235                 240

Ser Gln Arg Pro Asp Leu Ala Ala Asp Asn Pro Ile Asp Asp His His
                245                 250                 255

Thr Met Tyr Thr Val His Phe Tyr Thr Gly Ser His Ala Ala Ser Thr
```

```
              260                 265                 270
Glu Ser Tyr Pro Pro Glu Thr Pro Asn Ser Glu Arg Gly Asn Val Met
            275                 280                 285

Ser Asn Thr Arg Tyr Ala Leu Glu Asn Gly Val Ala Val Phe Ala Thr
        290                 295                 300

Glu Trp Gly Thr Ser Gln Ala Asn Gly Asp Gly Pro Tyr Phe Asp
305                 310                 315                 320

Glu Ala Asp Val Trp Ile Glu Phe Leu Asn Glu Asn Asn Ile Ser Trp
                325                 330                 335

Ala Asn Trp Ser Leu Thr Asn Lys Asn Glu Val Ser Gly Ala Phe Thr
            340                 345                 350

Pro Phe Glu Leu Gly Lys Ser Asn Ala Thr Ser Leu Asp Pro Gly Pro
        355                 360                 365

Asp Gln Val Trp Val Pro Glu Glu Leu Ser Leu Ser Gly Glu Tyr Val
        370                 375                 380

Arg Ala Arg Ile Lys Gly Val Asn Tyr Glu Pro Ile Asp Arg Thr Lys
385                 390                 395                 400

Tyr Thr Lys Val Leu Trp Asp Phe Asn Asp Gly Thr Lys Gln Gly Phe
                405                 410                 415

Gly Val Asn Gly Asp Ser Pro Val Glu Asp Val Val Ile Glu Asn Glu
            420                 425                 430

Ala Gly Ala Leu Lys Leu Ser Gly Leu Asp Ala Ser Asn Asp Val Ser
        435                 440                 445

Glu Gly Asn Tyr Trp Ala Asn Ala Arg Leu Ser Ala Asp Gly Trp Gly
        450                 455                 460

Lys Ser Val Asp Ile Leu Gly Ala Glu Lys Leu Thr Met Asp Val Ile
465                 470                 475                 480

Val Asp Glu Pro Thr Thr Val Ser Ile Ala Ala Ile Pro Gln Gly Pro
                485                 490                 495

Ser Ala Asn Trp Val Asn Pro Asn Arg Ala Ile Lys Val Glu Pro Thr
            500                 505                 510

Asn Phe Val Pro Leu Glu Asp Lys Phe Lys Ala Glu Leu Thr Ile Thr
        515                 520                 525

Ser Ala Asp Ser Pro Ser Leu Glu Ala Ile Ala Met His Ala Glu Asn
        530                 535                 540

Asn Asn Ile Asn Ile Ile Leu Phe Val Gly Thr Glu Gly Ala Asp
545                 550                 555                 560

Val Ile Tyr Leu Asp Asn Ile Lys Val Ile Gly Thr Glu Val Glu Ile
                565                 570                 575

Pro Val Val His Asp Pro Lys Gly Glu Ala Val Leu Pro Ser Val Phe
            580                 585                 590

Glu Asp Gly Thr Arg Gln Gly Trp Asp Trp Ala Gly Ser Gly Val
        595                 600                 605

Lys Thr Ala Leu Thr Ile Glu Glu Ala Asn Gly Ser Asn Ala Leu Ser
        610                 615                 620

Trp Glu Phe Gly Tyr Pro Glu Val Lys Pro Ser Asp Asn Trp Ala Thr
625                 630                 635                 640

Ala Pro Arg Leu Asp Phe Trp Lys Ser Asp Leu Val Arg Gly Glu Asn
                645                 650                 655

Asp Tyr Val Thr Phe Asp Phe Tyr Leu Asp Pro Val Arg Ala Thr Glu
            660                 665                 670

Gly Ala Met Asn Ile Asn Leu Val Phe Gln Pro Pro Thr Asn Gly Tyr
        675                 680                 685
```

```
Trp Val Gln Ala Pro Lys Thr Tyr Thr Ile Asn Phe Asp Glu Leu Glu
        690                 695                 700

Glu Pro Asn Gln Val Asn Gly Leu Tyr His Tyr Glu Val Lys Ile Asn
705                 710                 715                 720

Val Arg Asp Ile Thr Asn Ile Gln Asp Asp Thr Leu Leu Arg Asn Met
                725                 730                 735

Met Ile Ile Phe Ala Asp Val Glu Ser Asp Phe Ala Gly Arg Val Phe
            740                 745                 750

Val Asp Asn Val Arg Phe Glu Gly Ala Ala Thr Thr Glu Pro Val Glu
                755                 760                 765

Pro Glu Pro Val Asp Pro Gly Glu Glu Thr Pro Pro Val Asp Glu Lys
770                 775                 780

Glu Ala Lys Thr Glu Gln Lys Glu Ala Glu Lys Glu Glu Lys Glu Glu
785                 790                 795                 800
```

<210> SEQ ID NO 7
<211> LENGTH: 4126
<212> TYPE: DNA
<213> ORGANISM: Bacillus sp. KSM-64
<220> FEATURE:
<221> NAME/KEY: CDS
<222> LOCATION: (1407)..(3869)

<400> SEQUENCE: 7

```
ctcgagtgga gcaagaggct tcttaactcg ttcatgaatg tagaatagaa acaatggaaa      60
agctaaatta agaaaaaaac tttggggtta ttgcatcaat ctgcgataac cccttaaatg     120
ctaactacat agataaagga agataaaatg aacaattata aactaatgat tcaatatgat     180
ggtggtcgat acaaaggttg gcagcgtctt gggaacggtg aaaatacgat tcaaggtaaa     240
attgaaacgg ttttatcaga gatggtaggt agaaaaatag agattatagg gtctggtaga     300
acagatgctg gtgtccatgc tcttggacaa gtggctaatg taaaattaag cgaaaatttt     360
acagtaaaag aggttaaaga gtatttgaat cgttatttgc ctcatgatat cagtgtgact     420
gaggtgacgc tagttccaga tcgttttcac tcaaggtata cgcaaaggca caaaccctat     480
ctttataaaa tttggaatga ggattatact catccgttta tgcgtaagta cagcttgcac     540
atcgaaaaga aattacatat tgataacatg gtaaaagcaa gtcaactttt cgtaggagaa     600
catgatttta cagcttttttc taatgctaaa tctaaaaaga agacaaatac gagaacgatt     660
cactctataa ctattcaaga taatcaagga tttatagaca ttagggtttg tggagatggt     720
tttctttata acatggttag aaaaatggta gggactttga ttgaggttgg tctaggtgaa     780
aaggaacctg aacaagtact taccatttta gagtcaaaag atagaagcca agcaggattt     840
gccgatgcaa ccggcttata tttagaggga atttcttttt aaattgaata cggaataaaa     900
tcaggtaaac aggtcctgat tttattttttt tgaattttt tgagaactaa agattgaaat     960
agaagtagaa gacaacggac ataagaaaat tgtattagtt ttaattatag aaaacgcttt    1020
tctataatta tttataccta gaacgaaaat actgtttcga aagcggttta ctataaaacc    1080
ttatattccg gctctttttt taaacagggg gtgaaaattc actctagtat tctaatttca    1140
acatgctata ataaatttgt aagacgcaat atacatcttt tttttatgat atttgtaagc    1200
ggttaacctt gtgctatatg ccgatttagg aagggggtag attgagtcaa gtagtcataa    1260
tttagataac ttataagttg ttgagaagca ggagagaatc tgggttactc acaagttttt    1320
taaaacatta tcgaaagcac tttcggttat gcttatgaat ttagctattt gattcaatta    1380
```

```
ctttaataat tttaggaggt aatatg atg tta aga aag aaa aca aag cag ttg      1433
                             Met Leu Arg Lys Lys Thr Lys Gln Leu
                              1               5 att tct tcc att ctt att tta gtt tta ctt cta tct tta ttt ccg aca      1481
Ile Ser Ser Ile Leu Ile Leu Val Leu Leu Leu Ser Leu Phe Pro Thr
 10              15                  20                  25 gct ctt gca gca gaa gga aac act cgt gaa gac aat ttt aaa cat tta      1529
Ala Leu Ala Ala Glu Gly Asn Thr Arg Glu Asp Asn Phe Lys His Leu
             30                  35                  40 tta ggt aat gac aat gtt aaa cgc cct tct gag gct ggc gca tta caa      1577
Leu Gly Asn Asp Asn Val Lys Arg Pro Ser Glu Ala Gly Ala Leu Gln
         45                  50                  55 tta caa gaa gtc gat gga caa atg aca tta gta gat caa cat gga gaa      1625
Leu Gln Glu Val Asp Gly Gln Met Thr Leu Val Asp Gln His Gly Glu
     60                  65                  70 aaa att caa tta cgt gga atg agt aca cac gga tta caa tgg ttt cct      1673
Lys Ile Gln Leu Arg Gly Met Ser Thr His Gly Leu Gln Trp Phe Pro
 75                  80                  85 gag atc ttg aat gat aac gca tac aaa gct ctt gct aac gat tgg gaa      1721
Glu Ile Leu Asn Asp Asn Ala Tyr Lys Ala Leu Ala Asn Asp Trp Glu
 90                  95                 100                 105 tca aat atg att cgt cta gct atg tat gtc ggt gaa aat ggc tat gct      1769
Ser Asn Met Ile Arg Leu Ala Met Tyr Val Gly Glu Asn Gly Tyr Ala
             110                 115                 120 tca aat cca gag tta att aaa agc aga gtc att aaa gga ata gat ctt      1817
Ser Asn Pro Glu Leu Ile Lys Ser Arg Val Ile Lys Gly Ile Asp Leu
         125                 130                 135 gct att gaa aat gac atg tat gtc atc gtt gat tgg cat gta cat gca      1865
Ala Ile Glu Asn Asp Met Tyr Val Ile Val Asp Trp His Val His Ala
     140                 145                 150 cct ggt gat cct aga gat ccc gtt tac gct gga gca gaa gat ttc ttt      1913
Pro Gly Asp Pro Arg Asp Pro Val Tyr Ala Gly Ala Glu Asp Phe Phe
155                 160                 165 aga gat att gca gca tta tat cct aac aat cca cac att att tat gag      1961
Arg Asp Ile Ala Ala Leu Tyr Pro Asn Asn Pro His Ile Ile Tyr Glu
170                 175                 180                 185 tta gcg aat gag cca agt agt aac aat aat ggt gga gct ggg att cca      2009
Leu Ala Asn Glu Pro Ser Ser Asn Asn Asn Gly Gly Ala Gly Ile Pro
             190                 195                 200 aat aat gaa gaa ggt tgg aat gcg gta aaa gaa tac gct gat cca att      2057
Asn Asn Glu Glu Gly Trp Asn Ala Val Lys Glu Tyr Ala Asp Pro Ile
         205                 210                 215 gta gaa atg tta cgt gat agc ggg aac gca gat gac aat att atc att      2105
Val Glu Met Leu Arg Asp Ser Gly Asn Ala Asp Asp Asn Ile Ile Ile
     220                 225                 230 gtg ggt agt cca aac tgg agt cag cgt cct gac tta gca gct gat aat      2153
Val Gly Ser Pro Asn Trp Ser Gln Arg Pro Asp Leu Ala Ala Asp Asn
235                 240                 245 cca att gat gat cac cat aca atg tat act gtt cac ttc tac act ggt      2201
Pro Ile Asp Asp His His Thr Met Tyr Thr Val His Phe Tyr Thr Gly
250                 255                 260                 265 tca cat gct gct tca act gaa agc tat ccg cct gaa act cct aac tct      2249
Ser His Ala Ala Ser Thr Glu Ser Tyr Pro Pro Glu Thr Pro Asn Ser
             270                 275                 280 gaa aga gga aac gta atg agt aac act cgt tat gcg tta gaa aac gga      2297
Glu Arg Gly Asn Val Met Ser Asn Thr Arg Tyr Ala Leu Glu Asn Gly
         285                 290                 295 gta gca gta ttt gca aca gag tgg gga act agc caa gca aat gga gat      2345
Val Ala Val Phe Ala Thr Glu Trp Gly Thr Ser Gln Ala Asn Gly Asp
     300                 305                 310
```

| | | |
|---|---|---|
| ggt ggt cct tac ttt gat gaa gca gat gta tgg att gag ttt tta aat<br>Gly Gly Pro Tyr Phe Asp Glu Ala Asp Val Trp Ile Glu Phe Leu Asn<br>315                    320                    325 | 2393 |
| gaa aac aac att agc tgg gct aac tgg tct tta acg aat aaa aat gaa<br>Glu Asn Asn Ile Ser Trp Ala Asn Trp Ser Leu Thr Asn Lys Asn Glu<br>330                 335                 340                 345 | 2441 |
| gta tct ggt gca ttt aca cca ttc gag tta ggt aag tct aac gca aca<br>Val Ser Gly Ala Phe Thr Pro Phe Glu Leu Gly Lys Ser Asn Ala Thr<br>               350                    355                 360 | 2489 |
| agt ctt gac cca ggg cca gac caa gta tgg gta cca gaa gag tta agt<br>Ser Leu Asp Pro Gly Pro Asp Gln Val Trp Val Pro Glu Glu Leu Ser<br>365                    370                    375 | 2537 |
| ctt tct gga gaa tat gta cgt gct cgt att aaa ggt gtg aac tat gag<br>Leu Ser Gly Glu Tyr Val Arg Ala Arg Ile Lys Gly Val Asn Tyr Glu<br>           380                    385                 390 | 2585 |
| cca atc gac cgt aca aaa tac acg aaa gta ctt tgg gac ttt aat gat<br>Pro Ile Asp Arg Thr Lys Tyr Thr Lys Val Leu Trp Asp Phe Asn Asp<br>395                    400                    405 | 2633 |
| gga acg aag caa gga ttt gga gtg aat gga gat tct cca gtt gaa gat<br>Gly Thr Lys Gln Gly Phe Gly Val Asn Gly Asp Ser Pro Val Glu Asp<br>410                     415                 420                 425 | 2681 |
| gta gtt att gag aat gaa gcg ggc gct tta aaa ctt tca gga tta gat<br>Val Val Ile Glu Asn Glu Ala Gly Ala Leu Lys Leu Ser Gly Leu Asp<br>               430                    435                 440 | 2729 |
| gca agt aat gat gtt tct gaa ggt aat tac tgg gct aat gct cgt ctt<br>Ala Ser Asn Asp Val Ser Glu Gly Asn Tyr Trp Ala Asn Ala Arg Leu<br>                    445                    450                 455 | 2777 |
| tct gcc gac ggt tgg gga aaa agt gtt gat att tta ggt gct gaa aaa<br>Ser Ala Asp Gly Trp Gly Lys Ser Val Asp Ile Leu Gly Ala Glu Lys<br>           460                    465                 470 | 2825 |
| ctt act atg gat gtg att gtt gat gag ccg acc acg gta tca att gct<br>Leu Thr Met Asp Val Ile Val Asp Glu Pro Thr Thr Val Ser Ile Ala<br>475                    480                    485 | 2873 |
| gca att cca caa ggg cca tca gcc aat tgg gtt aat cca aat cgt gca<br>Ala Ile Pro Gln Gly Pro Ser Ala Asn Trp Val Asn Pro Asn Arg Ala<br>490                    495                 500                 505 | 2921 |
| att aag gtt gag cca act aat ttc gta ccg tta gga gat aag ttt aaa<br>Ile Lys Val Glu Pro Thr Asn Phe Val Pro Leu Gly Asp Lys Phe Lys<br>               510                    515                 520 | 2969 |
| gcg gaa tta act ata act tca gct gac tct cca tcg tta gaa gct att<br>Ala Glu Leu Thr Ile Thr Ser Ala Asp Ser Pro Ser Leu Glu Ala Ile<br>                    525                    530                 535 | 3017 |
| gcg atg cat gct gaa aat aac aac atc aac aac atc att ctt ttt gta<br>Ala Met His Ala Glu Asn Asn Asn Ile Asn Asn Ile Ile Leu Phe Val<br>           540                    545                 550 | 3065 |
| gga act gaa ggt gct gat gtt atc tat tta gat aac att aaa gta att<br>Gly Thr Glu Gly Ala Asp Val Ile Tyr Leu Asp Asn Ile Lys Val Ile<br>555                    560                    565 | 3113 |
| gga aca gaa gtt gaa att cca gtt gtt cat gat cca aaa gga gaa gct<br>Gly Thr Glu Val Glu Ile Pro Val Val His Asp Pro Lys Gly Glu Ala<br>570                    575                    580                 585 | 3161 |
| gtt ctt cct tct gtt ttt gaa gac ggt aca cgt caa ggt tgg gac tgg<br>Val Leu Pro Ser Val Phe Glu Asp Gly Thr Arg Gln Gly Trp Asp Trp<br>               590                    595                 600 | 3209 |
| gct gga gag tct ggt gtg aaa aca gct tta aca att gaa gaa gca aac<br>Ala Gly Glu Ser Gly Val Lys Thr Ala Leu Thr Ile Glu Glu Ala Asn<br>                    605                    610                 615 | 3257 |
| ggt tct aac gcg tta tca tgg gaa ttt gga tac cca gaa gta aaa cct<br>Gly Ser Asn Ala Leu Ser Trp Glu Phe Gly Tyr Pro Glu Val Lys Pro | 3305 |

```
                    620                 625                 630
agt gat aac tgg gca aca gct cca cgt tta gat ttc tgg aaa tct gac          3353
Ser Asp Asn Trp Ala Thr Ala Pro Arg Leu Asp Phe Trp Lys Ser Asp
            635                 640                 645 ttg gtt cgc ggt gaa aat gat tat gta act ttt gat ttc tat cta gat          3401
Leu Val Arg Gly Glu Asn Asp Tyr Val Thr Phe Asp Phe Tyr Leu Asp
650                 655                 660                 665 cca gtt cgt gca aca gaa ggc gca atg aat atc aat tta gta ttc cag          3449
Pro Val Arg Ala Thr Glu Gly Ala Met Asn Ile Asn Leu Val Phe Gln
                670                 675                 680 cca cct act aac ggg tat tgg gta caa gca cca aaa acg tat acg att          3497
Pro Pro Thr Asn Gly Tyr Trp Val Gln Ala Pro Lys Thr Tyr Thr Ile
            685                 690                 695 aac ttt gat gaa tta gag gaa gcg aat caa gta aat ggt tta tat cac          3545
Asn Phe Asp Glu Leu Glu Glu Ala Asn Gln Val Asn Gly Leu Tyr His
700                 705                 710 tat gaa gtg aaa att aac gta aga gat att aca aac att caa gat gac          3593
Tyr Glu Val Lys Ile Asn Val Arg Asp Ile Thr Asn Ile Gln Asp Asp
                715                 720                 725 acg tta cta cgt aac atg atg atc att ttt gca gat gta gaa agt gac          3641
Thr Leu Leu Arg Asn Met Met Ile Ile Phe Ala Asp Val Glu Ser Asp
730                 735                 740                 745 ttt gca ggg aga gtc ttt gta gat aat gtt cgt ttt gag ggg gct gct          3689
Phe Ala Gly Arg Val Phe Val Asp Asn Val Arg Phe Glu Gly Ala Ala
                750                 755                 760 act act gag ccg gtt gaa cca gag cca gtt gat cct ggc gaa gag acg          3737
Thr Thr Glu Pro Val Glu Pro Glu Pro Val Asp Pro Gly Glu Glu Thr
            765                 770                 775 ccg cct gtc gat gag aag gaa gcg aaa aaa gaa caa aaa gaa gca gag          3785
Pro Pro Val Asp Glu Lys Glu Ala Lys Lys Glu Gln Lys Glu Ala Glu
780                 785                 790 aaa gaa gag aaa gaa gca gta aaa gaa gaa aag aaa gaa gct aaa gaa          3833
Lys Glu Glu Lys Glu Ala Val Lys Glu Glu Lys Lys Glu Ala Lys Glu
                795                 800                 805 gaa aag aaa gca atc aaa aat gag gct acg aaa aaa taatctaata              3879
Glu Lys Lys Ala Ile Lys Asn Glu Ala Thr Lys Lys
810                 815                 820 aactagttat agggttatct aaaggtctga tgcagatctt ttagataacc ttttttttgca       3939 taactggaca tagaatggtt attaaagaaa gcaaggtgtt tatacgatat taaaaaggta       3999
gcgattttaa attgaaacct ttaataatgt cttgtgatag aatgatgaag taatttaaga       4059
gggggaaacg aagtgaaaac ggaaattct agtagaagaa aaacagacca agaaatactg       4119
caagctt                                                                   4126

<210> SEQ ID NO 8
<211> LENGTH: 821
<212> TYPE: PRT
<213> ORGANISM: Bacillus sp. KSM-64

<400> SEQUENCE: 8

Met Leu Arg Lys Lys Thr Lys Gln Leu Ile Ser Ser Ile Leu Ile Leu
1               5                   10                  15

Val Leu Leu Leu Ser Leu Phe Pro Thr Ala Leu Ala Ala Glu Gly Asn
            20                  25                  30

Thr Arg Glu Asp Asn Phe Lys His Leu Leu Gly Asn Asp Asn Val Lys
        35                  40                  45

Arg Pro Ser Glu Ala Gly Ala Leu Gln Leu Gln Glu Val Asp Gly Gln
    50                  55                  60
```

```
Met Thr Leu Val Asp Gln His Gly Glu Lys Ile Gln Leu Arg Gly Met
65                  70                  75                  80

Ser Thr His Gly Leu Gln Trp Phe Pro Glu Ile Leu Asn Asp Asn Ala
            85                  90                  95

Tyr Lys Ala Leu Ala Asn Asp Trp Glu Ser Asn Met Ile Arg Leu Ala
        100                 105                 110

Met Tyr Val Gly Glu Asn Gly Tyr Ala Ser Asn Pro Glu Leu Ile Lys
        115                 120                 125

Ser Arg Val Ile Lys Gly Ile Asp Leu Ala Ile Glu Asn Asp Met Tyr
    130                 135                 140

Val Ile Val Asp Trp His Val His Ala Pro Gly Asp Pro Arg Asp Pro
145                 150                 155                 160

Val Tyr Ala Gly Ala Glu Asp Phe Phe Arg Asp Ile Ala Ala Leu Tyr
            165                 170                 175

Pro Asn Asn Pro His Ile Ile Tyr Glu Leu Ala Asn Glu Pro Ser Ser
            180                 185                 190

Asn Asn Asn Gly Gly Ala Gly Ile Pro Asn Asn Glu Glu Gly Trp Asn
        195                 200                 205

Ala Val Lys Glu Tyr Ala Asp Pro Ile Val Glu Met Leu Arg Asp Ser
210                 215                 220

Gly Asn Ala Asp Asp Asn Ile Ile Ile Val Gly Ser Pro Asn Trp Ser
225                 230                 235                 240

Gln Arg Pro Asp Leu Ala Ala Asp Asn Pro Ile Asp Asp His His Thr
                245                 250                 255

Met Tyr Thr Val His Phe Tyr Thr Gly Ser His Ala Ala Ser Thr Glu
            260                 265                 270

Ser Tyr Pro Pro Glu Thr Pro Asn Ser Glu Arg Gly Asn Val Met Ser
        275                 280                 285

Asn Thr Arg Tyr Ala Leu Glu Asn Gly Val Ala Val Phe Ala Thr Glu
        290                 295                 300

Trp Gly Thr Ser Gln Ala Asn Gly Asp Gly Gly Pro Tyr Phe Asp Glu
305                 310                 315                 320

Ala Asp Val Trp Ile Glu Phe Leu Asn Glu Asn Asn Ile Ser Trp Ala
                325                 330                 335

Asn Trp Ser Leu Thr Asn Lys Asn Glu Val Ser Gly Ala Phe Thr Pro
            340                 345                 350

Phe Glu Leu Gly Lys Ser Asn Ala Thr Ser Leu Asp Pro Gly Pro Asp
        355                 360                 365

Gln Val Trp Val Pro Glu Glu Leu Ser Leu Ser Gly Glu Tyr Val Arg
        370                 375                 380

Ala Arg Ile Lys Gly Val Asn Tyr Glu Pro Ile Asp Arg Thr Lys Tyr
385                 390                 395                 400

Thr Lys Val Leu Trp Asp Phe Asn Asp Gly Thr Lys Gln Gly Phe Gly
                405                 410                 415

Val Asn Gly Asp Ser Pro Val Glu Val Val Ile Glu Asn Glu Ala
            420                 425                 430

Gly Ala Leu Lys Leu Ser Gly Leu Asp Ala Ser Asn Asp Val Ser Glu
            435                 440                 445

Gly Asn Tyr Trp Ala Asn Ala Arg Leu Ser Ala Asp Gly Trp Gly Lys
        450                 455                 460

Ser Val Asp Ile Leu Gly Ala Glu Lys Leu Thr Met Asp Val Ile Val
465                 470                 475                 480
```

```
Asp Glu Pro Thr Thr Val Ser Ile Ala Ala Ile Pro Gln Gly Pro Ser
                485                 490                 495

Ala Asn Trp Val Asn Pro Asn Arg Ala Ile Lys Val Glu Pro Thr Asn
            500                 505                 510

Phe Val Pro Leu Gly Asp Lys Phe Lys Ala Glu Leu Thr Ile Thr Ser
        515                 520                 525

Ala Asp Ser Pro Ser Leu Glu Ala Ile Ala Met His Ala Glu Asn Asn
    530                 535                 540

Asn Ile Asn Asn Ile Ile Leu Phe Val Gly Thr Gly Ala Asp Val
545                 550                 555                 560

Ile Tyr Leu Asp Asn Ile Lys Val Ile Gly Thr Glu Val Glu Ile Pro
                565                 570                 575

Val Val His Asp Pro Lys Gly Glu Ala Val Leu Pro Ser Val Phe Glu
            580                 585                 590

Asp Gly Thr Arg Gln Gly Trp Asp Trp Ala Gly Glu Ser Gly Val Lys
        595                 600                 605

Thr Ala Leu Thr Ile Glu Glu Ala Asn Gly Ser Asn Ala Leu Ser Trp
    610                 615                 620

Glu Phe Gly Tyr Pro Glu Val Lys Pro Ser Asp Asn Trp Ala Thr Ala
625                 630                 635                 640

Pro Arg Leu Asp Phe Trp Lys Ser Asp Leu Val Arg Gly Asn Asp
                645                 650                 655

Tyr Val Thr Phe Asp Phe Tyr Leu Asp Pro Val Arg Ala Thr Glu Gly
            660                 665                 670

Ala Met Asn Ile Asn Leu Val Phe Gln Pro Pro Thr Asn Gly Tyr Trp
        675                 680                 685

Val Gln Ala Pro Lys Thr Tyr Thr Ile Asn Phe Asp Glu Leu Glu Glu
    690                 695                 700

Ala Asn Gln Val Asn Gly Leu Tyr His Tyr Glu Val Lys Ile Asn Val
705                 710                 715                 720

Arg Asp Ile Thr Asn Ile Gln Asp Asp Thr Leu Leu Arg Asn Met Met
                725                 730                 735

Ile Ile Phe Ala Asp Val Glu Ser Asp Phe Ala Gly Arg Val Phe Val
            740                 745                 750

Asp Asn Val Arg Phe Glu Gly Ala Thr Thr Glu Pro Val Glu Pro
        755                 760                 765

Glu Pro Val Asp Pro Gly Glu Glu Thr Pro Pro Val Asp Glu Lys Glu
    770                 775                 780

Ala Lys Lys Glu Gln Lys Glu Ala Glu Lys Glu Glu Lys Glu Ala Val
785                 790                 795                 800

Lys Glu Glu Lys Lys Glu Ala Lys Glu Glu Lys Lys Ala Ile Lys Asn
                805                 810                 815

Glu Ala Thr Lys Lys
            820

<210> SEQ ID NO 9
<211> LENGTH: 3498
<212> TYPE: DNA
<213> ORGANISM: Bacillus sp. KSM-635
<220> FEATURE:
<221> NAME/KEY: CDS
<222> LOCATION: (605)..(3427)

<400> SEQUENCE: 9
ggcacctgag gaagtagcga atcctgttct tgatgcacat ccatacttaa cttctggatt    60
```

```
tgccttcatg agtcgtgatg aaaacggaag tgcaccatta catggactgt tgcatttaa        120 ttattcggca ctgattagct gtggcatttc cgcttctgct ctttctggaa tgaagtacgg        180
ggtcccaaga cttgtcactg ccattgccga tcagttattc aagatgatc gagacgagat         240 tctaaaggac ttctttgagt atgatgaaa ggagtttgtc ggaaactggc ctttaaacgt         300
ctaaatgaac ataatagcga aagggcttaa ccaaaaatat gaattgaacc cacataaatt       360
tgtgggtttt tattaatcaa aaaaatggta aataaaccta ttttaacaat gcttataacc       420 attttctat ttattgcata aaaaaatcag taaaaaaatt catttatatg tagacgtaaa        480
ttaacaaata ttatattata tatacgaaag cggtttcgaa aaatagagga aggaggagag      540
tttttagttt ttgttgtttg tttattgtaa gcgtttacta ttaatacatt tctgggaggt      600
```

| | | | | | | | | | | | | | | | | |
|---|---|---|---|---|---|---|---|---|---|---|---|---|---|---|---|---|
| tatt | atg | aaa | ata | aag | caa | att | aaa | caa | tct | tta | tct | ttg | ctt | tta | atc | 649 |
| | Met | Lys | Ile | Lys | Gln | Ile | Lys | Gln | Ser | Leu | Ser | Leu | Leu | Leu | Ile | |
| | 1 | | | 5 | | | | | 10 | | | | | 15 | | |

```
atc aca ctc att atg tca cta ttt gtt cct atg gct tca gca aac aca        697
Ile Thr Leu Ile Met Ser Leu Phe Val Pro Met Ala Ser Ala Asn Thr
            20                  25                  30 aat gag tct aag tct aat gca ttt cct ttt tct gat gtt aaa aaa act        745
Asn Glu Ser Lys Ser Asn Ala Phe Pro Phe Ser Asp Val Lys Lys Thr
        35                  40                  45 tct tgg tct ttt cca tat ata aag gat tta tat gag caa gaa gtt att        793
Ser Trp Ser Phe Pro Tyr Ile Lys Asp Leu Tyr Glu Gln Glu Val Ile
    50                  55                  60 aca gga aca tct gca aca acg ttc tct cca aca gat tcc gtt act cgt        841
Thr Gly Thr Ser Ala Thr Thr Phe Ser Pro Thr Asp Ser Val Thr Arg
65                  70                  75 gca caa ttt aca gtg atg ctt acc cgt ggt ctt gga cta gaa gca tct        889
Ala Gln Phe Thr Val Met Leu Thr Arg Gly Leu Gly Leu Glu Ala Ser
    80              85                  90                  95 tct aaa gat tac cct ttt aaa gat cgt aaa aac tgg gct tac aaa gaa        937
Ser Lys Asp Tyr Pro Phe Lys Asp Arg Lys Asn Trp Ala Tyr Lys Glu
                100                 105                 110 att caa gct gca tat gaa gct gga att gta act ggg aaa aca aac ggt        985
Ile Gln Ala Ala Tyr Glu Ala Gly Ile Val Thr Gly Lys Thr Asn Gly
            115                 120                 125 gaa ttt gca cca aat gaa aac att act cgt gaa caa atg gct gct atg        1033
Glu Phe Ala Pro Asn Glu Asn Ile Thr Arg Glu Gln Met Ala Ala Met
        130                 135                 140 gcc gta cgt gct tat gaa tac tta gaa aat gag cta tct tta cca gaa        1081
Ala Val Arg Ala Tyr Glu Tyr Leu Glu Asn Glu Leu Ser Leu Pro Glu
    145                 150                 155 gag caa aga gaa tat aat gac tct tct tct att tca acc ttt gct caa        1129
Glu Gln Arg Glu Tyr Asn Asp Ser Ser Ser Ile Ser Thr Phe Ala Gln
160                 165                 170                 175 gat gct gtt caa aaa gca tac gta tta gag cta atg gaa gga aat aca        1177
Asp Ala Val Gln Lys Ala Tyr Val Leu Glu Leu Met Glu Gly Asn Thr
            180                 185                 190 gat gga tat ttt caa cca aaa aga aac tct act aga gaa cag tct gct        1225
Asp Gly Tyr Phe Gln Pro Lys Arg Asn Ser Thr Arg Glu Gln Ser Ala
        195                 200                 205 aaa gtt atc tct act tta ctt tgg aaa gta gct agt cat gat tat tta        1273
Lys Val Ile Ser Thr Leu Leu Trp Lys Val Ala Ser His Asp Tyr Leu
    210                 215                 220 tac cat aca gaa gct gtt aaa agc cct tca gaa gct ggt gcg ctt cag        1321
Tyr His Thr Glu Ala Val Lys Ser Pro Ser Glu Ala Gly Ala Leu Gln
225                 230                 235 tta gta gaa cta aac gga caa tta aca cta gct ggt gaa gat ggt act        1369
Leu Val Glu Leu Asn Gly Gln Leu Thr Leu Ala Gly Glu Asp Gly Thr
```

```
Leu Val Glu Leu Asn Gly Gln Leu Thr Leu Ala Gly Glu Asp Gly Thr
240                 245                 250                 255 ccc gtt caa tta cgt gga atg agt aca cat ggc cta caa tgg ttc ggt    1417
Pro Val Gln Leu Arg Gly Met Ser Thr His Gly Leu Gln Trp Phe Gly
                260                 265                 270 gaa atc gta aac gaa aac gct ttc gta gca cta tcg aat gat tgg gga    1465
Glu Ile Val Asn Glu Asn Ala Phe Val Ala Leu Ser Asn Asp Trp Gly
                275                 280                 285 tct aac atg att cgt ctc gct atg tac att ggc gaa aat gga tat gca    1513
Ser Asn Met Ile Arg Leu Ala Met Tyr Ile Gly Glu Asn Gly Tyr Ala
            290                 295                 300 aca aac cct gaa gta aaa gat tta gtt tat gaa gga att gaa tta gcg    1561
Thr Asn Pro Glu Val Lys Asp Leu Val Tyr Glu Gly Ile Glu Leu Ala
        305                 310                 315 ttt gag cac gat atg tat gta att gtt gac tgg cat gta cat gct cct    1609
Phe Glu His Asp Met Tyr Val Ile Val Asp Trp His Val His Ala Pro
320                 325                 330                 335 ggt gat cct aga gcg gat gta tac tca ggt gct tat gat ttc ttc gaa    1657
Gly Asp Pro Arg Ala Asp Val Tyr Ser Gly Ala Tyr Asp Phe Phe Glu
                340                 345                 350 gaa att gct gat cat tac aaa gat cat ccg aaa aac cat tat atc att    1705
Glu Ile Ala Asp His Tyr Lys Asp His Pro Lys Asn His Tyr Ile Ile
                355                 360                 365 tgg gaa cta gca aac gaa cca agt cca aat aat aac ggt gga cct gga    1753
Trp Glu Leu Ala Asn Glu Pro Ser Pro Asn Asn Asn Gly Gly Pro Gly
            370                 375                 380 tta aca aat gat gaa aaa ggt tgg gaa gct gta aaa gaa tat gca gag    1801
Leu Thr Asn Asp Glu Lys Gly Trp Glu Ala Val Lys Glu Tyr Ala Glu
385                 390                 395 cca atc gtt gaa atg ttg cgt gaa aaa ggt gac aac atg att tta gtt    1849
Pro Ile Val Glu Met Leu Arg Glu Lys Gly Asp Asn Met Ile Leu Val
400                 405                 410                 415 gga aat cct aac tgg agc caa cgt cct gac tta tca gct gac aac cca    1897
Gly Asn Pro Asn Trp Ser Gln Arg Pro Asp Leu Ser Ala Asp Asn Pro
                420                 425                 430 att gat gca gaa aat atc atg tat tct gtt cac ttc tac aca ggc tca    1945
Ile Asp Ala Glu Asn Ile Met Tyr Ser Val His Phe Tyr Thr Gly Ser
                435                 440                 445 cat ggc gct tct cac att ggt tac cct gaa gga aca cca agc tct gaa    1993
His Gly Ala Ser His Ile Gly Tyr Pro Glu Gly Thr Pro Ser Ser Glu
            450                 455                 460 cgt tct aat gtt atg gct aac gtt cgt tat gct cta gac aat ggc gtt    2041
Arg Ser Asn Val Met Ala Asn Val Arg Tyr Ala Leu Asp Asn Gly Val
465                 470                 475 gct gtg ttt gcg aca gag tgg ggt acg agt caa gcg aat gga gat gga    2089
Ala Val Phe Ala Thr Glu Trp Gly Thr Ser Gln Ala Asn Gly Asp Gly
480                 485                 490                 495 gga cct tat ttt gat gaa gct gat gtt tgg ctt aat ttc tta aac aaa    2137
Gly Pro Tyr Phe Asp Glu Ala Asp Val Trp Leu Asn Phe Leu Asn Lys
                500                 505                 510 cat aac att agc tgg gca aac tgg tcg tta acg aac aaa aat gag att    2185
His Asn Ile Ser Trp Ala Asn Trp Ser Leu Thr Asn Lys Asn Glu Ile
            515                 520                 525 tct gga gca ttt aca cct ttt gag ctt ggt aga aca gat gct aca gat    2233
Ser Gly Ala Phe Thr Pro Phe Glu Leu Gly Arg Thr Asp Ala Thr Asp
        530                 535                 540 ctt gat cca ggt gct aat caa gta tgg gca ccc gag gaa cta agt tta    2281
Leu Asp Pro Gly Ala Asn Gln Val Trp Ala Pro Glu Glu Leu Ser Leu
545                 550                 555
```

```
tct ggt gaa tat gtt cgt gct cgt att aaa gga att gag tat aca cct    2329
Ser Gly Glu Tyr Val Arg Ala Arg Ile Lys Gly Ile Glu Tyr Thr Pro
560             565                 570                 575 atc gac cgc aca aaa ttc aca aag ctt gtt tgg gat ttt aac gat gga    2377
Ile Asp Arg Thr Lys Phe Thr Lys Leu Val Trp Asp Phe Asn Asp Gly
            580                 585                 590 aca aca caa gga ttc caa gtt aat gga gac agc cct aac aaa gaa agc    2425
Thr Thr Gln Gly Phe Gln Val Asn Gly Asp Ser Pro Asn Lys Glu Ser
        595                 600                 605 att act tta agt aat aat aat gat gca tta caa att gaa gga tta aat    2473
Ile Thr Leu Ser Asn Asn Asn Asp Ala Leu Gln Ile Glu Gly Leu Asn
    610                 615                 620 gta agt aat gat att tct gaa gga aac tac tgg gat aat gta cgc ctg    2521
Val Ser Asn Asp Ile Ser Glu Gly Asn Tyr Trp Asp Asn Val Arg Leu
625                 630                 635 tca gct gat ggc tgg agt gaa aat gta gat att tta ggt gct aca gag    2569
Ser Ala Asp Gly Trp Ser Glu Asn Val Asp Ile Leu Gly Ala Thr Glu
640             645                 650                 655 ctt aca att gat gtt atc gtt gaa gaa ccg aca aca gtt tca att gct    2617
Leu Thr Ile Asp Val Ile Val Glu Glu Pro Thr Thr Val Ser Ile Ala
            660                 665                 670 gct att cca caa gga cct gct gct ggc tgg gct aac ccg act aga gca    2665
Ala Ile Pro Gln Gly Pro Ala Ala Gly Trp Ala Asn Pro Thr Arg Ala
        675                 680                 685 att aaa gta act gaa gac gat ttc gaa tct ttc gga gat gga tac aaa    2713
Ile Lys Val Thr Glu Asp Asp Phe Glu Ser Phe Gly Asp Gly Tyr Lys
    690                 695                 700 gct ctc gta act att act tct gaa gat tca cct tca ctt gaa acc att    2761
Ala Leu Val Thr Ile Thr Ser Glu Asp Ser Pro Ser Leu Glu Thr Ile
705                 710                 715 gca act agt cct gaa gac aat aca atg agc aat atc att cta ttt gta    2809
Ala Thr Ser Pro Glu Asp Asn Thr Met Ser Asn Ile Ile Leu Phe Val
            720                 725                 730                 735 ggt act gaa gat gca gat gtt att tct tta gat aat atc acg gtt tct    2857
Gly Thr Glu Asp Ala Asp Val Ile Ser Leu Asp Asn Ile Thr Val Ser
        740                 745                 750 ggt act gag att gaa att gaa gtt att cac gat gaa aaa gga aca gca    2905
Gly Thr Glu Ile Glu Ile Glu Val Ile His Asp Glu Lys Gly Thr Ala
    755                 760                 765 aca ctt cct tct act ttt gaa gat gga act cgc caa ggc tgg gat tgg    2953
Thr Leu Pro Ser Thr Phe Glu Asp Gly Thr Arg Gln Gly Trp Asp Trp
770                 775                 780 cat aca gaa tca gga gtt aag aca gct ctt aca att gaa gaa gct aat    3001
His Thr Glu Ser Gly Val Lys Thr Ala Leu Thr Ile Glu Glu Ala Asn
785                 790                 795 gga tct aac gct ctt tca tgg gaa tat gcg tat cct gaa gta aaa cca    3049
Gly Ser Asn Ala Leu Ser Trp Glu Tyr Ala Tyr Pro Glu Val Lys Pro
800             805                 810                 815 agt gat ggt tgg gct act gct cct cgt cta gac ttc tgg aaa gac gaa    3097
Ser Asp Gly Trp Ala Thr Ala Pro Arg Leu Asp Phe Trp Lys Asp Glu
            820                 825                 830 cta gtt cgt ggc aca agc gac tat att agt ttt gac ttt tac atc gat    3145
Leu Val Arg Gly Thr Ser Asp Tyr Ile Ser Phe Asp Phe Tyr Ile Asp
        835                 840                 845 gca gtt cgt gct tct gaa ggt gct ata tca att aac gcc gtt ttc caa    3193
Ala Val Arg Ala Ser Glu Gly Ala Ile Ser Ile Asn Ala Val Phe Gln
    850                 855                 860 cca cct gca aac ggg tat tgg caa gaa gtt cca act aca ttt gaa att    3241
Pro Pro Ala Asn Gly Tyr Trp Gln Glu Val Pro Thr Thr Phe Glu Ile
865                 870                 875
```

```
gat tta aca gag ctt gat tct gca act gta act tct gat gag ttg tat    3289
Asp Leu Thr Glu Leu Asp Ser Ala Thr Val Thr Ser Asp Glu Leu Tyr
880                 885                 890                 895 cat tat gaa gta aaa att aac att aga gac att gag gct att aca gac    3337
His Tyr Glu Val Lys Ile Asn Ile Arg Asp Ile Glu Ala Ile Thr Asp
                900                 905                 910 gat aca gag ctt cgt aac tta tta cta atc ttt gct gat gaa gac agt    3385
Asp Thr Glu Leu Arg Asn Leu Leu Leu Ile Phe Ala Asp Glu Asp Ser
            915                 920                 925 gat ttt gct ggt aga gtt ttt gtt gat aat gta aga ttt gaa            3427
Asp Phe Ala Gly Arg Val Phe Val Asp Asn Val Arg Phe Glu
        930                 935                 940 taatttaaaa acagtagata gagagactct ctatctacct gtttattgct tactattcgt  3487
cttccacttt t                                                       3498

<210> SEQ ID NO 10
<211> LENGTH: 941
<212> TYPE: PRT
<213> ORGANISM: Bacillus sp. KSM-635

<400> SEQUENCE: 10

Met Lys Ile Lys Gln Ile Lys Gln Ser Leu Ser Leu Leu Leu Ile Ile
1               5                   10                  15

Thr Leu Ile Met Ser Leu Phe Val Pro Met Ala Ser Ala Asn Thr Asn
            20                  25                  30

Glu Ser Lys Ser Asn Ala Phe Pro Phe Ser Asp Val Lys Lys Thr Ser
        35                  40                  45

Trp Ser Phe Pro Tyr Ile Lys Asp Leu Tyr Glu Gln Glu Val Ile Thr
    50                  55                  60

Gly Thr Ser Ala Thr Thr Phe Ser Pro Thr Asp Ser Val Thr Arg Ala
65                  70                  75                  80

Gln Phe Thr Val Met Leu Thr Arg Gly Leu Gly Leu Glu Ala Ser Ser
                85                  90                  95

Lys Asp Tyr Pro Phe Lys Asp Arg Lys Asn Trp Ala Tyr Lys Glu Ile
            100                 105                 110

Gln Ala Ala Tyr Glu Ala Gly Ile Val Thr Gly Lys Thr Asn Gly Glu
        115                 120                 125

Phe Ala Pro Asn Glu Asn Ile Thr Arg Glu Gln Met Ala Ala Met Ala
    130                 135                 140

Val Arg Ala Tyr Glu Tyr Leu Glu Asn Glu Leu Ser Leu Pro Glu Glu
145                 150                 155                 160

Gln Arg Glu Tyr Asn Asp Ser Ser Ile Ser Thr Phe Ala Gln Asp
                165                 170                 175

Ala Val Gln Lys Ala Tyr Val Leu Glu Leu Met Glu Gly Asn Thr Asp
            180                 185                 190

Gly Tyr Phe Gln Pro Lys Arg Asn Ser Thr Arg Glu Gln Ser Ala Lys
        195                 200                 205

Val Ile Ser Thr Leu Leu Trp Lys Val Ala Ser His Asp Tyr Leu Tyr
    210                 215                 220

His Thr Glu Ala Val Lys Ser Pro Ser Glu Ala Gly Ala Leu Gln Leu
225                 230                 235                 240

Val Glu Leu Asn Gly Gln Leu Thr Leu Ala Gly Glu Asp Gly Thr Pro
                245                 250                 255

Val Gln Leu Arg Gly Met Ser Thr His Gly Leu Gln Trp Phe Gly Glu
            260                 265                 270
```

-continued

```
Ile Val Asn Glu Asn Ala Phe Val Ala Leu Ser Asn Asp Trp Gly Ser
        275                 280                 285
Asn Met Ile Arg Leu Ala Met Tyr Ile Gly Glu Asn Gly Tyr Ala Thr
    290                 295                 300
Asn Pro Glu Val Lys Asp Leu Val Tyr Glu Gly Ile Glu Leu Ala Phe
305                 310                 315                 320
Glu His Asp Met Tyr Val Ile Val Asp Trp His Val His Ala Pro Gly
                325                 330                 335
Asp Pro Arg Ala Asp Val Tyr Ser Gly Ala Tyr Asp Phe Phe Glu Glu
            340                 345                 350
Ile Ala Asp His Tyr Lys Asp His Pro Lys Asn His Tyr Ile Ile Trp
        355                 360                 365
Glu Leu Ala Asn Glu Pro Ser Pro Asn Asn Asn Gly Gly Pro Gly Leu
    370                 375                 380
Thr Asn Asp Glu Lys Gly Trp Glu Ala Val Lys Glu Tyr Ala Glu Pro
385                 390                 395                 400
Ile Val Glu Met Leu Arg Glu Lys Gly Asp Asn Met Ile Leu Val Gly
                405                 410                 415
Asn Pro Asn Trp Ser Gln Arg Pro Asp Leu Ser Ala Asn Pro Ile
            420                 425                 430
Asp Ala Glu Asn Ile Met Tyr Ser Val His Phe Tyr Thr Gly Ser His
        435                 440                 445
Gly Ala Ser His Ile Gly Tyr Pro Glu Gly Thr Pro Ser Ser Glu Arg
    450                 455                 460
Ser Asn Val Met Ala Asn Val Arg Tyr Ala Leu Asp Asn Gly Val Ala
465                 470                 475                 480
Val Phe Ala Thr Glu Trp Gly Thr Ser Gln Ala Asn Gly Asp Gly Gly
                485                 490                 495
Pro Tyr Phe Asp Glu Ala Asp Val Trp Leu Asn Phe Leu Asn Lys His
            500                 505                 510
Asn Ile Ser Trp Ala Asn Trp Ser Leu Thr Asn Lys Asn Glu Ile Ser
        515                 520                 525
Gly Ala Phe Thr Pro Phe Glu Leu Gly Arg Thr Asp Ala Thr Asp Leu
    530                 535                 540
Asp Pro Gly Ala Asn Gln Val Trp Ala Pro Glu Glu Leu Ser Leu Ser
545                 550                 555                 560
Gly Glu Tyr Val Arg Ala Arg Ile Lys Gly Ile Glu Tyr Thr Pro Ile
                565                 570                 575
Asp Arg Thr Lys Phe Thr Lys Leu Val Trp Asp Phe Asn Asp Gly Thr
            580                 585                 590
Thr Gln Gly Phe Gln Val Asn Gly Asp Ser Pro Asn Lys Glu Ser Ile
        595                 600                 605
Thr Leu Ser Asn Asn Asn Asp Ala Leu Gln Ile Glu Gly Leu Asn Val
    610                 615                 620
Ser Asn Asp Ile Ser Glu Gly Asn Tyr Trp Asp Asn Val Arg Leu Ser
625                 630                 635                 640
Ala Asp Gly Trp Ser Glu Asn Val Asp Ile Leu Gly Ala Thr Glu Leu
                645                 650                 655
Thr Ile Asp Val Ile Val Glu Glu Pro Thr Thr Val Ser Ile Ala Ala
            660                 665                 670
Ile Pro Gln Gly Pro Ala Ala Gly Trp Ala Asn Pro Thr Arg Ala Ile
        675                 680                 685
```

| | | | | | | | | | | | | | | |
|---|---|---|---|---|---|---|---|---|---|---|---|---|---|---|
| Lys | Val | Thr | Glu | Asp | Asp | Phe | Glu | Ser | Phe | Gly | Asp | Gly | Tyr | Lys | Ala |
| | 690 | | | | 695 | | | | 700 | | | | | |

Leu Val Thr Ile Thr Ser Glu Asp Ser Pro Ser Leu Glu Thr Ile Ala
705                 710                 715                 720

Thr Ser Pro Glu Asp Asn Thr Met Ser Asn Ile Ile Leu Phe Val Gly
            725                 730                 735

Thr Glu Asp Ala Asp Val Ile Ser Leu Asp Asn Ile Thr Val Ser Gly
            740                 745                 750

Thr Glu Ile Glu Ile Glu Val Ile His Asp Glu Lys Gly Thr Ala Thr
            755                 760                 765

Leu Pro Ser Thr Phe Glu Asp Gly Thr Arg Gln Gly Trp Asp Trp His
770                 775                 780

Thr Glu Ser Gly Val Lys Thr Ala Leu Thr Ile Glu Glu Ala Asn Gly
785                 790                 795                 800

Ser Asn Ala Leu Ser Trp Glu Tyr Ala Tyr Pro Glu Val Lys Pro Ser
            805                 810                 815

Asp Gly Trp Ala Thr Ala Pro Arg Leu Asp Phe Trp Lys Asp Glu Leu
            820                 825                 830

Val Arg Gly Thr Ser Asp Tyr Ile Ser Phe Asp Phe Tyr Ile Asp Ala
            835                 840                 845

Val Arg Ala Ser Glu Gly Ala Ile Ser Ile Asn Ala Val Phe Gln Pro
850                 855                 860

Pro Ala Asn Gly Tyr Trp Gln Glu Val Pro Thr Thr Phe Glu Ile Asp
865                 870                 875                 880

Leu Thr Glu Leu Asp Ser Ala Thr Val Thr Ser Asp Glu Leu Tyr His
            885                 890                 895

Tyr Glu Val Lys Ile Asn Ile Arg Asp Ile Glu Ala Ile Thr Asp Asp
            900                 905                 910

Thr Glu Leu Arg Asn Leu Leu Leu Ile Phe Ala Asp Glu Asp Ser Asp
            915                 920                 925

Phe Ala Gly Arg Val Phe Val Asp Asn Val Arg Phe Glu
930                 935                 940

<210> SEQ ID NO 11
<211> LENGTH: 2708
<212> TYPE: DNA
<213> ORGANISM: Bacillus sp. N-4
<220> FEATURE:
<221> NAME/KEY: CDS
<222> LOCATION: (231)..(2705)

<400> SEQUENCE: 11
tttcttacaa aaagggggtg ttctataaat agtagatgac tagactttct agttcagctt     60 actattttg gaatagcgaa attttataa tggtttacga aaccactttc gtatttaggt    120
tacattattt tgattgtacg aaagttacat attttatttc gttttaaata ttccgaaacg    180
taaaggtgga ctccgataag tgacaaacga cattaatggg agggttcata gtg agg      236
                                                         Val Arg
                                                          1 aac aaa tta aga cgt tta tta gca att atg atg gct gtt ctt tta att    284
Asn Lys Leu Arg Arg Leu Leu Ala Ile Met Met Ala Val Leu Leu Ile
      5                  10                  15 act tca ttg ttt gca cca atg gtg agt gca gaa gaa ggt gat aat gga    332
Thr Ser Leu Phe Ala Pro Met Val Ser Ala Glu Glu Gly Asp Asn Gly
 20                  25                  30 gat gac gat gat tta gta act cca att gaa att gaa gaa aga cct cat    380
Asp Asp Asp Asp Leu Val Thr Pro Ile Glu Ile Glu Glu Arg Pro His

```
                    35                  40                  45                  50
gag tca aat tat gag aaa tat ccg gcg cta tta gat gga gga cta gat      428
Glu Ser Asn Tyr Glu Lys Tyr Pro Ala Leu Leu Asp Gly Gly Leu Asp
                55                  60                  65 gaa aga aga cct tca gaa gct ggt gca tta caa ttg gtt gaa gta gat      476
Glu Arg Arg Pro Ser Glu Ala Gly Ala Leu Gln Leu Val Glu Val Asp
            70                  75                  80 gga caa gtt act tta gca gat caa gat ggt gtt cca att caa tta cgt      524
Gly Gln Val Thr Leu Ala Asp Gln Asp Gly Val Pro Ile Gln Leu Arg
        85                  90                  95 ggg atg agt aca cac ggt tta caa tgg ttt ggc gaa atc gta aat gaa      572
Gly Met Ser Thr His Gly Leu Gln Trp Phe Gly Glu Ile Val Asn Glu
    100                 105                 110 aac gct ttt gca gcg tta gca aat gat tgg gga tct aat gta att aga      620
Asn Ala Phe Ala Ala Leu Ala Asn Asp Trp Gly Ser Asn Val Ile Arg
115                 120                 125                 130 tta gcg cta tat atc gga gaa aat gcg tat cgt tac aac cca gat ctt      668
Leu Ala Leu Tyr Ile Gly Glu Asn Ala Tyr Arg Tyr Asn Pro Asp Leu
                135                 140                 145 att gaa aag gta tat gca ggg ata gaa tta gcg aaa gaa aac gat atg      716
Ile Glu Lys Val Tyr Ala Gly Ile Glu Leu Ala Lys Glu Asn Asp Met
            150                 155                 160 tat gtc att att gat tgg cat gtt cat gca cct ggt gac cct aat gct      764
Tyr Val Ile Ile Asp Trp His Val His Ala Pro Gly Asp Pro Asn Ala
        165                 170                 175 gac att tac caa ggt ggc gtt aat gaa gat gga gaa gaa tat tta gga      812
Asp Ile Tyr Gln Gly Gly Val Asn Glu Asp Gly Glu Glu Tyr Leu Gly
    180                 185                 190 gct aaa gat ttc ttc tta cac att gct gaa aag tac cca aat gac cca      860
Ala Lys Asp Phe Phe Leu His Ile Ala Glu Lys Tyr Pro Asn Asp Pro
195                 200                 205                 210 cat cta att tat gag ctt gca aac gag cca agc tca aat agt agc ggt      908
His Leu Ile Tyr Glu Leu Ala Asn Glu Pro Ser Ser Asn Ser Ser Gly
                215                 220                 225 ggc cct ggg ata acg aat gat gag gac gga tgg gaa gca gtt aga gaa      956
Gly Pro Gly Ile Thr Asn Asp Glu Asp Gly Trp Glu Ala Val Arg Glu
            230                 235                 240 tat gct caa cct atc gta gat gca ctt cgt gat agt gga aat gct gaa     1004
Tyr Ala Gln Pro Ile Val Asp Ala Leu Arg Asp Ser Gly Asn Ala Glu
        245                 250                 255 gat aac att att atc gta ggt agc cct aac tgg agt caa aga atg gat     1052
Asp Asn Ile Ile Ile Val Gly Ser Pro Asn Trp Ser Gln Arg Met Asp
    260                 265                 270 tta gct gct gct gat aat cca att gat gac cat cat aca atg tat aca     1100
Leu Ala Ala Ala Asp Asn Pro Ile Asp Asp His His Thr Met Tyr Thr
275                 280                 285                 290 cta cat ttc tat act ggt act cac gaa gga aca aat gag agt tat cca     1148
Leu His Phe Tyr Thr Gly Thr His Glu Gly Thr Asn Glu Ser Tyr Pro
                295                 300                 305 gaa ggt ata tct agc gag gat cgc agt aac gta atg gct aac gca aaa     1196
Glu Gly Ile Ser Ser Glu Asp Arg Ser Asn Val Met Ala Asn Ala Lys
            310                 315                 320 tac gca cta gat aaa gga aaa gca atc ttt gca aca gag tgg ggc gta     1244
Tyr Ala Leu Asp Lys Gly Lys Ala Ile Phe Ala Thr Glu Trp Gly Val
        325                 330                 335 agt gaa gct gac ggt aat aat ggt cct tac tta aat gaa gca gat gtc     1292
Ser Glu Ala Asp Gly Asn Asn Gly Pro Tyr Leu Asn Glu Ala Asp Val
    340                 345                 350 tgg ctt aat ttt cta aat gaa aac aac att agc tgg act aac tgg tct     1340
```

```
Trp Leu Asn Phe Leu Asn Glu Asn Asn Ile Ser Trp Thr Asn Trp Ser
355                 360                 365                 370 tta aca aat aaa aat gaa act tct ggt gca ttt aca cca ttt att tta    1388
Leu Thr Asn Lys Asn Glu Thr Ser Gly Ala Phe Thr Pro Phe Ile Leu
                375                 380                 385 aat gaa tct gat gca act gat ctt gac cca ggt gaa gat caa gta tgg    1436
Asn Glu Ser Asp Ala Thr Asp Leu Asp Pro Gly Glu Asp Gln Val Trp
            390                 395                 400 tct atg gaa gaa tta agt gta tct ggt gaa tac gta cgt tca cgt ata    1484
Ser Met Glu Glu Leu Ser Val Ser Gly Glu Tyr Val Arg Ser Arg Ile
        405                 410                 415 ttg gga gaa gaa tat cag cca att gat cgt aca cca aga gag gaa ttc    1532
Leu Gly Glu Glu Tyr Gln Pro Ile Asp Arg Thr Pro Arg Glu Glu Phe
    420                 425                 430 tct gaa gta att tgg gac ttt aac gac ggg act aca caa ggg ttt gta    1580
Ser Glu Val Ile Trp Asp Phe Asn Asp Gly Thr Thr Gln Gly Phe Val
435                 440                 445                 450 caa aat agt gat agc cct cta gat gta act att gaa aat gta aat gac    1628
Gln Asn Ser Asp Ser Pro Leu Asp Val Thr Ile Glu Asn Val Asn Asp
                455                 460                 465 gca ctt caa atc acc ggt tta gat gaa agt aac gct att gct gga gaa    1676
Ala Leu Gln Ile Thr Gly Leu Asp Glu Ser Asn Ala Ile Ala Gly Glu
            470                 475                 480 gaa gaa gat tac tgg tcg aat gta cga att tct gca gat gaa tgg gaa    1724
Glu Glu Asp Tyr Trp Ser Asn Val Arg Ile Ser Ala Asp Glu Trp Glu
        485                 490                 495 gaa aca ttt gac ata cta ggt gca gag gag tta tcg atg gac gtt gta    1772
Glu Thr Phe Asp Ile Leu Gly Ala Glu Glu Leu Ser Met Asp Val Val
    500                 505                 510 gtt gat gat cca act aca gta gcc att gca gca att cct caa agt agt    1820
Val Asp Asp Pro Thr Thr Val Ala Ile Ala Ala Ile Pro Gln Ser Ser
515                 520                 525                 530 gct cat gaa tgg gcg aac gca tct aat tcc gtt tta ata acg gaa gat    1868
Ala His Glu Trp Ala Asn Ala Ser Asn Ser Val Leu Ile Thr Glu Asp
                535                 540                 545 gac ttt gaa gaa caa gaa gat ggc aca tac aaa gca ctc tta acc atc    1916
Asp Phe Glu Glu Gln Glu Asp Gly Thr Tyr Lys Ala Leu Leu Thr Ile
            550                 555                 560 acg ggt gaa gat gca cca aat ctt aca aac ata gca gaa gac ccg gaa    1964
Thr Gly Glu Asp Ala Pro Asn Leu Thr Asn Ile Ala Glu Asp Pro Glu
        565                 570                 575 ggt agt gag ctt aat aac att att ctt ttt gtg ggc aca gaa aat gct    2012
Gly Ser Glu Leu Asn Asn Ile Ile Leu Phe Val Gly Thr Glu Asn Ala
    580                 585                 590 gat gtg att tca tta gat aat att act gtt aca gga gac cgt gaa tca    2060
Asp Val Ile Ser Leu Asp Asn Ile Thr Val Thr Gly Asp Arg Glu Ser
595                 600                 605                 610 gta cca gaa cca gtg gaa cat gac act aaa gga gat tca gca ctt ccg    2108
Val Pro Glu Pro Val Glu His Asp Thr Lys Gly Asp Ser Ala Leu Pro
                615                 620                 625 tct gat ttt gaa gat ggt act cgt caa ggc tgg gag tgg gat agt gaa    2156
Ser Asp Phe Glu Asp Gly Thr Arg Gln Gly Trp Glu Trp Asp Ser Glu
            630                 635                 640 tct gca gtt aga aca gca tta aca att gaa gag gct aac gga tca aat    2204
Ser Ala Val Arg Thr Ala Leu Thr Ile Glu Glu Ala Asn Gly Ser Asn
        645                 650                 655 gct ctt tca tgg gaa tat gca tac cca gaa gtg aag cca agt gat gat    2252
Ala Leu Ser Trp Glu Tyr Ala Tyr Pro Glu Val Lys Pro Ser Asp Asp
    660                 665                 670
```

```
tgg gct act gcg cca aga cta aca tta tat aaa gat gat tta gtt cgt    2300
Trp Ala Thr Ala Pro Arg Leu Thr Leu Tyr Lys Asp Asp Leu Val Arg
675                 680                 685                 690 ggc gat tat gaa ttt gta gcc ttt gat ttt tac att gat cca att gaa    2348
Gly Asp Tyr Glu Phe Val Ala Phe Asp Phe Tyr Ile Asp Pro Ile Glu
                695                 700                 705 gat aga gct aca gaa ggt gct att gat att aac tta att ttt caa ccg    2396
Asp Arg Ala Thr Glu Gly Ala Ile Asp Ile Asn Leu Ile Phe Gln Pro
            710                 715                 720 cca gcg gca gga tat tgg gct caa gca tct gaa aca ttt gaa att gat    2444
Pro Ala Ala Gly Tyr Trp Ala Gln Ala Ser Glu Thr Phe Glu Ile Asp
        725                 730                 735 cta gaa gaa cta gat tct gct acg gta aca gac gat ggc cta tat cat    2492
Leu Glu Glu Leu Asp Ser Ala Thr Val Thr Asp Asp Gly Leu Tyr His
    740                 745                 750 tat gag gta gag att aat att gaa gat atc gaa aat gat att gag tta    2540
Tyr Glu Val Glu Ile Asn Ile Glu Asp Ile Glu Asn Asp Ile Glu Leu
755                 760                 765                 770 cgt aat cta atg ctt att ttc gca gac gat gaa agt gac ttt gct gga    2588
Arg Asn Leu Met Leu Ile Phe Ala Asp Asp Glu Ser Asp Phe Ala Gly
                775                 780                 785 aga gta ttt ctt gat aat gta aga atg gat atg tct tta gaa aca aaa    2636
Arg Val Phe Leu Asp Asn Val Arg Met Asp Met Ser Leu Glu Thr Lys
            790                 795                 800 gta gaa gta cta gaa aga aat ata aat gaa ttg caa gaa cag tta gta    2684
Val Glu Val Leu Glu Arg Asn Ile Asn Glu Leu Gln Glu Gln Leu Val
        805                 810                 815 gaa gta gaa gct tta atg cgg tag                                    2708
Glu Val Glu Ala Leu Met Arg
    820                 825

<210> SEQ ID NO 12
<211> LENGTH: 825
<212> TYPE: PRT
<213> ORGANISM: Bacillus sp. N-4

<400> SEQUENCE: 12

Val Arg Asn Lys Leu Arg Arg Leu Leu Ala Ile Met Met Ala Val Leu
1               5                   10                  15

Leu Ile Thr Ser Leu Phe Ala Pro Met Val Ser Ala Glu Glu Gly Asp
            20                  25                  30

Asn Gly Asp Asp Asp Leu Val Thr Pro Ile Glu Ile Glu Glu Arg
        35                  40                  45

Pro His Glu Ser Asn Tyr Glu Lys Tyr Pro Ala Leu Leu Asp Gly Gly
    50                  55                  60

Leu Asp Glu Arg Arg Pro Ser Glu Ala Gly Ala Leu Gln Leu Val Glu
65                  70                  75                  80

Val Asp Gly Gln Val Thr Leu Ala Asp Gln Asp Gly Val Pro Ile Gln
                85                  90                  95

Leu Arg Gly Met Ser Thr His Gly Leu Gln Trp Phe Gly Glu Ile Val
            100                 105                 110

Asn Glu Asn Ala Phe Ala Ala Leu Ala Asn Asp Trp Gly Ser Asn Val
        115                 120                 125

Ile Arg Leu Ala Leu Tyr Ile Gly Glu Asn Ala Tyr Arg Tyr Asn Pro
    130                 135                 140

Asp Leu Ile Glu Lys Val Tyr Ala Gly Ile Glu Leu Ala Lys Glu Asn
145                 150                 155                 160

Asp Met Tyr Val Ile Ile Asp Trp His Val His Ala Pro Gly Asp Pro
```

-continued

```
                165                 170                 175
Asn Ala Asp Ile Tyr Gln Gly Gly Val Asn Glu Asp Gly Glu Glu Tyr
                180                 185                 190
Leu Gly Ala Lys Asp Phe Phe Leu His Ile Ala Glu Lys Tyr Pro Asn
                195                 200                 205
Asp Pro His Leu Ile Tyr Glu Leu Ala Asn Glu Pro Ser Ser Asn Ser
            210                 215                 220
Ser Gly Gly Pro Gly Ile Thr Asn Asp Glu Asp Gly Trp Glu Ala Val
225                 230                 235                 240
Arg Glu Tyr Ala Gln Pro Ile Val Asp Ala Leu Arg Asp Ser Gly Asn
                245                 250                 255
Ala Glu Asp Asn Ile Ile Val Gly Ser Pro Asn Trp Ser Gln Arg
                260                 265                 270
Met Asp Leu Ala Ala Ala Asp Asn Pro Ile Asp Asp His His Thr Met
            275                 280                 285
Tyr Thr Leu His Phe Tyr Thr Gly Thr His Glu Gly Thr Asn Glu Ser
            290                 295                 300
Tyr Pro Glu Gly Ile Ser Ser Glu Asp Arg Ser Asn Val Met Ala Asn
305                 310                 315                 320
Ala Lys Tyr Ala Leu Asp Lys Gly Lys Ala Ile Phe Ala Thr Glu Trp
                325                 330                 335
Gly Val Ser Glu Ala Asp Gly Asn Asn Gly Pro Tyr Leu Asn Glu Ala
                340                 345                 350
Asp Val Trp Leu Asn Phe Leu Asn Glu Asn Asn Ile Ser Trp Thr Asn
                355                 360                 365
Trp Ser Leu Thr Asn Lys Asn Glu Thr Ser Gly Ala Phe Thr Pro Phe
            370                 375                 380
Ile Leu Asn Glu Ser Asp Ala Thr Asp Leu Asp Pro Gly Glu Asp Gln
385                 390                 395                 400
Val Trp Ser Met Glu Glu Leu Ser Val Ser Gly Glu Tyr Val Arg Ser
                405                 410                 415
Arg Ile Leu Gly Glu Glu Tyr Gln Pro Ile Asp Arg Thr Pro Arg Glu
                420                 425                 430
Glu Phe Ser Glu Val Ile Trp Asp Phe Asn Asp Gly Thr Thr Gln Gly
            435                 440                 445
Phe Val Gln Asn Ser Asp Ser Pro Leu Asp Val Thr Ile Glu Asn Val
            450                 455                 460
Asn Asp Ala Leu Gln Ile Thr Gly Leu Asp Glu Ser Asn Ala Ile Ala
465                 470                 475                 480
Gly Glu Glu Glu Asp Tyr Trp Ser Asn Val Arg Ile Ser Ala Asp Glu
                485                 490                 495
Trp Glu Glu Thr Phe Asp Ile Leu Gly Ala Glu Leu Ser Met Asp
                500                 505                 510
Val Val Val Asp Asp Pro Thr Thr Val Ala Ile Ala Ala Ile Pro Gln
            515                 520                 525
Ser Ser Ala His Glu Trp Ala Asn Ala Ser Asn Ser Val Leu Ile Thr
            530                 535                 540
Glu Asp Asp Phe Glu Glu Gln Glu Asp Gly Thr Tyr Lys Ala Leu Leu
545                 550                 555                 560
Thr Ile Thr Gly Glu Asp Ala Pro Asn Leu Thr Asn Ile Ala Glu Asp
                565                 570                 575
Pro Glu Gly Ser Glu Leu Asn Asn Ile Ile Leu Phe Val Gly Thr Glu
            580                 585                 590
```

-continued

```
Asn Ala Asp Val Ile Ser Leu Asp Asn Ile Thr Val Thr Gly Asp Arg
            595                 600                 605
Glu Ser Val Pro Glu Pro Val Glu His Asp Thr Lys Gly Asp Ser Ala
610                 615                 620
Leu Pro Ser Asp Phe Glu Asp Gly Thr Arg Gln Gly Trp Glu Trp Asp
625                 630                 635                 640
Ser Glu Ser Ala Val Arg Thr Ala Leu Thr Ile Glu Glu Ala Asn Gly
                645                 650                 655
Ser Asn Ala Leu Ser Trp Glu Tyr Ala Tyr Pro Glu Val Lys Pro Ser
            660                 665                 670
Asp Asp Trp Ala Thr Ala Pro Arg Leu Thr Leu Tyr Lys Asp Asp Leu
        675                 680                 685
Val Arg Gly Asp Tyr Glu Phe Val Ala Phe Asp Phe Tyr Ile Asp Pro
    690                 695                 700
Ile Glu Asp Arg Ala Thr Glu Gly Ala Ile Asp Ile Asn Leu Ile Phe
705                 710                 715                 720
Gln Pro Pro Ala Ala Gly Tyr Trp Ala Gln Ala Ser Glu Thr Phe Glu
                725                 730                 735
Ile Asp Leu Glu Glu Leu Asp Ser Ala Thr Val Thr Asp Asp Gly Leu
            740                 745                 750
Tyr His Tyr Glu Val Glu Ile Asn Ile Glu Asp Ile Glu Asn Asp Ile
        755                 760                 765
Glu Leu Arg Asn Leu Met Leu Ile Phe Ala Asp Glu Ser Asp Phe
    770                 775                 780
Ala Gly Arg Val Phe Leu Asp Asn Val Arg Met Asp Met Ser Leu Glu
785                 790                 795                 800
Thr Lys Val Glu Val Leu Glu Arg Asn Ile Asn Glu Leu Gln Glu Gln
                805                 810                 815
Leu Val Glu Val Glu Ala Leu Met Arg
            820                 825
```

<210> SEQ ID NO 13
<211> LENGTH: 37
<212> TYPE: DNA
<213> ORGANISM: Artificial
<220> FEATURE:
<223> OTHER INFORMATION: Oligonucleotide as primer (237UB1) designed
      from the nucleotide sequence of 5'-flanking region of Bacillus sp.
      strain KSM-S237 cellulase gene

<400> SEQUENCE: 13
ttgcggatcc aacaggctta tatttagagg aaatttc                              37

<210> SEQ ID NO 14
<211> LENGTH: 20
<212> TYPE: DNA
<213> ORGANISM: Artificial
<220> FEATURE:
<223> OTHER INFORMATION: Oligonucleotide as primer (S237RV) designed
      from the nucleotide sequence of 3'-flanking region of Bacillus sp.
      strain KSM-S237 cellulase gene

<400> SEQUENCE: 14
tcgctaccct tttattatcg                                                 20

<210> SEQ ID NO 15
<211> LENGTH: 30
<212> TYPE: DNA
<213> ORGANISM: Artificial

```
<220> FEATURE:
<223> OTHER INFORMATION: Oligonucleotide as mutagenesis primer (Q71E-RV)
      designed from the nucleotide sequence of Bacillus sp. strain KSM-
      S237 cellulase gene

<400> SEQUENCE: 15
attttttctc catgttcatc tactaatgtc                                      30

<210> SEQ ID NO 16
<211> LENGTH: 30
<212> TYPE: DNA
<213> ORGANISM: Artificial
<220> FEATURE:
<223> OTHER INFORMATION: Oligonucleotide as mutagenesis primer (Q71E-FW)
      designed from the nucleotide sequence of Bacillus sp. strain KSM-
      S237 cellulase gene

<400> SEQUENCE: 16
gacattagta gatgaacatg gagaaaaaat                                      30

<210> SEQ ID NO 17
<211> LENGTH: 28
<212> TYPE: DNA
<213> ORGANISM: Artificial
<220> FEATURE:
<223> OTHER INFORMATION: Oligonucleotide as mutagenesis primer
      (S193R-RV) designed from the nucleotide sequence of Bacillus sp.
      strain KSM-S237 cellulase gene

<400> SEQUENCE: 17
tccaccatta ttattacgac tcggctca                                        28

<210> SEQ ID NO 18
<211> LENGTH: 28
<212> TYPE: DNA
<213> ORGANISM: Artificial
<220> FEATURE:
<223> OTHER INFORMATION: Oligonucleotide as mutagenesis primer
      (S193R-FW) designed from the nucleotide sequence of Bacillus sp.
      strain KSM-S237 cellulase gene

<400> SEQUENCE: 18
tgagccgagt cgtaataata atggtgga                                        28

<210> SEQ ID NO 19
<211> LENGTH: 24
<212> TYPE: DNA
<213> ORGANISM: Artificial
<220> FEATURE:
<223> OTHER INFORMATION: Oligonucleotide as mutagenesis primer
      (Q242S-RV) designed from the nucleotide sequence of Bacillus sp.
      strain KSM-S237 cellulase gene

<400> SEQUENCE: 19
agtccggacg cgaactccag tttg                                            24

<210> SEQ ID NO 20
<211> LENGTH: 24
<212> TYPE: DNA
<213> ORGANISM: Artificial
<220> FEATURE:
<223> OTHER INFORMATION: Oligonucleotide as mutagenesis primer
      (Q242S-FW) designed from the nucleotide sequence of Bacillus sp.
      strain KSM-S237 cellulase gene

<400> SEQUENCE: 20
caaactggag ttcgcgtccg gact                                            24
```

<210> SEQ ID NO 21
<211> LENGTH: 30
<212> TYPE: DNA
<213> ORGANISM: Artificial
<220> FEATURE:
<223> OTHER INFORMATION: Oligonucleotide as mutagenesis primer
      (N419A-RV) designed from the nucleotide sequence of Bacillus sp.
      strain KSM-S237 cellulase gene

<400> SEQUENCE: 21
tttggagaat ccgaagccac tccaaatcct                                30

<210> SEQ ID NO 22
<211> LENGTH: 30
<212> TYPE: DNA
<213> ORGANISM: Artificial
<220> FEATURE:
<223> OTHER INFORMATION: Oligonucleotide as mutagenesis primer
      (N419A-FW) designed from the nucleotide sequence of Bacillus sp.
      strain KSM-S237 cellulase gene

<400> SEQUENCE: 22
aggatttgga gtggcttcgg attctccaaa                                30

<210> SEQ ID NO 23
<211> LENGTH: 29
<212> TYPE: DNA
<213> ORGANISM: Artificial
<220> FEATURE:
<223> OTHER INFORMATION: Oligonucleotide as mutagenesis primer
      (D421A-RV) designed from the nucleotide sequence of Bacillus sp.
      strain KSM-S237 cellulase gene

<400> SEQUENCE: 23
ctttatttgg agaagccgaa ttcactcca                                 29

<210> SEQ ID NO 24
<211> LENGTH: 29
<212> TYPE: DNA
<213> ORGANISM: Artificial
<220> FEATURE:
<223> OTHER INFORMATION: Oligonucleotide as mutagenesis primer
      (D421A-FW) designed from the nucleotide sequence of Bacillus sp.
      strain KSM-S237 cellulase gene

<400> SEQUENCE: 24
tggagtgaat tcggcttctc caaataaag                                 29

<210> SEQ ID NO 25
<211> LENGTH: 30
<212> TYPE: DNA
<213> ORGANISM: Artificial
<220> FEATURE:
<223> OTHER INFORMATION: Oligonucleotide as mutagenesis primer
      (W454Y-RV) designed from the nucleotide sequence of Bacillus sp.
      strain KSM-S237 cellulase gene

<400> SEQUENCE: 25
agacgagcat tagcatagaa gttgccatct                                30

<210> SEQ ID NO 26
<211> LENGTH: 30
<212> TYPE: DNA
<213> ORGANISM: Artificial
<220> FEATURE:
<223> OTHER INFORMATION: Oligonucleotide as mutagenesis primer
      (W454Y-FW) designed from the nucleotide sequence of Bacillus sp.
      strain KSM-S237 cellulase gene

<400> SEQUENCE: 26
agatggcaac ttctatgcta atgctcgtct                                        30

<210> SEQ ID NO 27
<211> LENGTH: 26
<212> TYPE: DNA
<213> ORGANISM: Artificial
<220> FEATURE:
<223> OTHER INFORMATION: Oligonucleotide as mutagenesis primer
      (W501Y-RV) designed from the nucleotide sequence of Bacillus sp.
      strain KSM-S237 cellulase gene

<400> SEQUENCE: 27
ctctggattt gcatatccac ttttac                                            26

<210> SEQ ID NO 28
<211> LENGTH: 26
<212> TYPE: DNA
<213> ORGANISM: Artificial
<220> FEATURE:
<223> OTHER INFORMATION: Oligonucleotide as mutagenesis primer
      (W501Y-FW) designed from the nucleotide sequence of Bacillus sp.
      strain KSM-S237 cellulase gene

<400> SEQUENCE: 28
gtaaaagtgg atatgcaaat ccagag                                            26

<210> SEQ ID NO 29
<211> LENGTH: 28
<212> TYPE: DNA
<213> ORGANISM: Artificial
<220> FEATURE:
<223> OTHER INFORMATION: Oligonucleotide as mutagenesis primer
      (Q58R-RV) designed from the nucleotide sequence of Bacillus sp.
      strain KSM-S237 cellulase gene

<400> SEQUENCE: 29
atcgacttct tgtaattcta atgcgcca                                          28

<210> SEQ ID NO 30
<211> LENGTH: 28
<212> TYPE: DNA
<213> ORGANISM: Artificial
<220> FEATURE:
<223> OTHER INFORMATION: Oligonucleotide as mutagenesis primer
      (Q58R-FW) designed from the nucleotide sequence of Bacillus sp.
      strain KSM-S237 cellulase gene

<400> SEQUENCE: 30
tggcgcatta gaattacaag aagtcgat                                          28

<210> SEQ ID NO 31
<211> LENGTH: 28
<212> TYPE: DNA
<213> ORGANISM: Artificial
<220> FEATURE:
<223> OTHER INFORMATION: Oligonucleotide as mutagenesis primer
      (Q58E-RV) designed from the nucleotide sequence of Bacillus sp.
      strain KSM-S237 cellulase gene

<400> SEQUENCE: 31
atcgacttct tgtaaacgta atgcgcca                                          28

<210> SEQ ID NO 32
<211> LENGTH: 28
<212> TYPE: DNA

```
<213> ORGANISM: Artificial
<220> FEATURE:
<223> OTHER INFORMATION: Oligonucleotide as mutagenesis primer
      (Q58E-FW) designed from the nucleotide sequence of Bacillus sp.
      strain KSM-S237 cellulase gene

<400> SEQUENCE: 32
tggcgcatta cgtttacaag aagtcgat                                    28

<210> SEQ ID NO 33
<211> LENGTH: 28
<212> TYPE: DNA
<213> ORGANISM: Artificial
<220> FEATURE:
<223> OTHER INFORMATION: Oligonucleotide as mutagenesis primer
      (A56D-FW) designed from the nucleotide sequence of Bacillus sp.
      strain KSM-S237 cellulase gene

<400> SEQUENCE: 33
tctgaggctg gcgatttaca attacaag                                    28

<210> SEQ ID NO 34
<211> LENGTH: 28
<212> TYPE: DNA
<213> ORGANISM: Artificial
<220> FEATURE:
<223> OTHER INFORMATION: Oligonucleotide as mutagenesis primer
      (A56D-RV) designed from the nucleotide sequence of Bacillus sp.
      strain KSM-S237 cellulase gene

<400> SEQUENCE: 34
cttgtaattg taaatcgcca gcctcaga                                    28
```

MUTATED ALKALINE CELLULASE

FIELD OF THE INVENTION

The present invention relates to a mutant alkaline cellulase having enhanced anti-redeposition ability, and a mutant alkaline cellulase having both enhanced anti-redeposition ability and enhanced protease resistance.

BACKGROUND OF THE INVENTION

For effective washing of clothing products and the like, it is important to sufficiently detach dirt materials from the object to be washed or to rapidly remove dirt materials through enzymatic degradation or the like, as well as seriously important to prevent reattachment of dirt materials that have been once detached from the object to be washed (preventing of redeposition). Particularly, with regard to minute dirt materials such as soot, it is known that if the dirt materials are once diffused in washing water and then are reattached to the object to be washed, it is very difficult to remove the dirt materials. Accordingly, various anti-redeposition agents have been conventionally incorporated into, for example, detergents for clothing products. Examples of the anti-redeposition agents that may be used include cellulose-based compounds such as carboxymethyl cellulose, hydroxypropylmethyl cellulose, and hydroxybutylmethyl cellulose; nonionic polymers such as polyethylene glycol, polyvinyl alcohol, and polyvinylpyrrolidone; and amino acid polymers. However, there have been needs for development of the anti-redeposition agent having a further enhanced effect.

Meanwhile, it has been a traditional practice to incorporate hydrolases such as proteases, lipases and amylases as cleaning aids, into cleaning agents. Cellulases, which constitute one class of hydrolases, are originally known as enzymes that function in neutral to acidic condition, and it has been conventionally considered that cellulases are not suitable to be incorporated into alkaline cleaning agents for clothing. However, in recent years, alkaline cellulases or variants thereof are obtained from plural organisms including thermophilic or alkalophilic bacteria of the genus *Bacillus*, and the cellulases or variants thereof may also be incorporated into alkaline detergents for clothing (for example, Patent Documents 1 to 6).

Cellulases are enzymes which hydrolyze glycoside bond within β-1,4-glucans including cellulose. Cellulases are mainly produced by bacteria or plants and are available in various kingdoms. Cellulases are classified into endoglucanases (EC3.2.1.4) that degrade cellulose from the interior of the molecule, and exoglucanases (cellobiohydrolases) (EC3.2.1.91) that degrade cellulose from the reduced ends or non-reduced ends of the sugar chain, and release cellobiose. On the other hand, glycoside hydrolases including cellulases are classified into one glycoside hydrolase family, and that family is currently further classified into subfamily 1 to subfamily 108. Cellulases are classified, based on their structures, into families 5, 6, 7, 8, 9, 10, 12, 44, 45, 48, 51, 61, and 74 of the glycoside hydrolase family, and it is also known that the amino acid sequence identity between those families is very low.

However, in recent years, it has been found by analyses of amino acid sequences or three-dimensional structures that cellulases have a common domain having catalytic activity (catalytic domain; CD) and another common functional domain that are linked to each other through a linker. A representative example of the other functional domain is a cellulose binding region having cellulose binding properties (also referred to as cellulose binding module: CBM) (see FIG. 1A). Cellulases usually have plural CBMs. Since cellulose is basically water-insoluble, a cellulase binds to the cellulose surface through the CBMs, and thereby relatively increases the substrate concentration. CBMs are also classified into 40 or more families based on the amino acid sequence identity. In regard to these CBMs, identification of amino acid residues that directly participate in binding to the cellulose has also been carried out (Non-Patent Document 1).

Patent Document 1 discloses a *Bacillus* sp. strain KSM-S237-derived alkaline cellulase having heat resistance, Patent Document 2 discloses a mutant alkaline cellulase having an optimum pH increased to near pH 10.5, and Patent Document 3 discloses a mutant alkaline cellulase having enhanced productivity. Furthermore, Patent Documents 4 and 6 describe that some of these cellulases show anti-redeposition activity.

PRIOR ART DOCUMENTS

Patent Document

Patent Document 1: JP-B-3512981
Patent Document 2: JP-A-2003-310270
Patent Document 3: JP-A-2004-140
Patent Document 4: JP-A-2004-536593
Patent Document 5: JP-A-2006-509850
Patent Document 6: JP-A-2002-265998

Non-Patent Document

Non-Patent Document 1: Boraston A. B. et al., Biochem. J., (2002) 361, p. 35-40

SUMMARY OF THE INVENTION

The present invention includes the following:

[1] A mutant alkaline cellulase having an amino acid sequence in which at least one amino acid residue selected from the amino acid residues at the positions corresponding to positions 58, 45, 52, 56, 60, 64, 66, 71, 103, 119, 122, 123, 124, 125, 127, 130, 140, 161, 164, 175, 176, 178, 179, 181, 193, 194, 195, 196, 197, 199, 202, 203, 217, 225, 227, 228, 251, 267, 272, 276, 277, 280, 282, 297, 310, 312, 318, 324, 345, 354, 356, 357, 360, 363, 368, 418, 419, 420, 421, 422, 453, 454, 455, 457, 458, 459, 494, 495, 496, 500, 501, 502, 503, 504, 550, 551, 552, 604, 605, 606, 607, 608, 640, 641, 642, 644, 645, 646, 683, 684, 685, 690, 691, 692, 693, 694, 739, 740, and 741 of the amino acid sequence of an alkaline cellulase set forth in SEQ ID NO: 2 or of the amino acid sequence of an alkaline cellulase having at least 70% identity with the amino acid sequence of SEQ ID NO: 2, is substituted with other amino acid residue.

[2] The mutant alkaline cellulase according to the above item [1], wherein the at last one amino acid residue is a glutamine residue at the position corresponding to position 58 of the amino acid sequence of an alkaline cellulase set forth in SEQ ID NO: 2 or of the amino acid sequence having at least 90% identity with the amino acid sequence of SEQ ID NO: 2.

[3] The mutant alkaline cellulase according to the above item [2], wherein the other amino acid residue is arginine or glutamic acid residue.

[4] The mutant alkaline cellulase according to the above item [1], wherein the at least one amino acid residue is selected from non-charged amino acid residues at the positions corresponding to positions 45, 52, 56, 60, 64, 66, 71, 103, 119, 122, 123, 124, 125, 127, 130, 140, 161, 164, 175, 176, 178, 179, 181, 193, 194, 195, 196, 197, 199, 202, 203, 217, 225, 227, 228, 251, 267, 272, 276, 277, 280, 282, 297, 310, 312, 318, 324, 345, 354, 356, 357, 360, 363, and 368 of the amino acid sequence set forth in SEQ ID NO: 2, and the other amino acid residue is a charged amino acid residue.

[5] The mutant alkaline cellulase according to the above item [4], wherein the charged amino acid residue is selected from the group consisting of glutamic acid, aspartic acid, lysine, arginine and histidine residue.

[6] The mutant alkaline cellulase according to the above item [4], wherein the non-charged amino acid residue is alanine, serine, glutamine or asparagine residue, and the charged amino acid residue is glutamic acid, aspartic acid or arginine residue.

[7] The mutant alkaline cellulase according to the above item [4], wherein the non-charged amino acid residue is at least one amino acid residue selected from the non-charged amino acid residues at the positions corresponding to positions 71 and 193 of the amino acid sequence set forth in SEQ ID NO: 2, and the charged amino acid residue is an acidic amino acid residue.

[8] The mutant alkaline cellulase according to the above item [1], wherein the at least one amino acid residue is selected from the amino acid residues at the positions corresponding to positions 418, 419, 420, 421, 422, 453, 454, 455, 457, 458, 459, 494, 495, 496, 500, 501, 502, 503, 504, 550, 551, 552, 604, 605, 606, 607, 608, 640, 641, 642, 644, 645, 646, 683, 684, 685, 690, 691, 692, 693, 694, 739, 740, and 741 of the amino acid sequence set forth in SEQ ID NO: 2.

[9] The mutant alkaline cellulase according to the above item [8], wherein the at least one amino acid residue is selected from the amino acid residues at the positions corresponding to positions 419, 421, 454, and 501 of the amino acid sequence set forth in SEQ ID NO: 2.

[10] The mutant alkaline cellulase according to the above item [8], wherein the at least one amino acid residue is tryptophan residue while the other amino acid residue is tyrosine residue, or the at least one amino acid residue is an amino acid other than tryptophan residue while the other amino acid residue is alanine residue.

[11] The mutant alkaline cellulase according to the above items [1] to [10], wherein a signal sequence consisting of the amino acid residues at the positions 1 to 30 of the amino acid sequence set forth in SEQ ID NO: 2, or of amino acid residues equivalent to the foregoing amino acid residues, is deleted.

[12] A gene encoding the mutant alkaline cellulase according to any one of the above items [1] to [11].

[13] A recombinant vector including the gene according to the above item [12].

[14] A transformant containing the recombinant vector according to the above item [13].

[15] The transformant according to the above item [14], being a microorganism.

[16] An anti-redeposition agent including the mutant alkaline cellulase according to any one of the above items [1] to [11].

[17] An enzyme composition including the mutant alkaline cellulase according to any one of the above items [1] to [11].

[18] The enzyme composition according to the above item [17], further including one or more enzymes selected from the group consisting of a protease, a cellulase, a β-glucanase, a hemicellulase, a lipase, a peroxidase, a laccase, an α-amylase, a glucoamylase, a cutinase, a pectinase, a reductase, an oxidase, a phenoloxidase, a ligninase, a pullulanase, a pectate lyase, a xyloglucanase, a xylanase, a pectin acetylesterase, a polygalacturonase, a rhamnogalacturonase, a pectin lyase, another mannanase, a pectin methylesterase, a cellobiohydrolase, a transglutaminase, and mixtures thereof.

[19] A cleaning agent composition including the mutant alkaline cellulase according to the above items [1] to [11], the anti-redeposition agent according to the above item [16], or the enzyme composition according to the above item [17] or [18].

[20] A method for producing a mutant alkaline cellulase, the method including expressing the mutant alkaline cellulase from the gene according to the above item [12].

[21] A method for enhancing the anti-redeposition ability of an alkaline cellulase, by substituting at least one amino acid residue selected from the amino acid residues at the positions corresponding to positions 58, 45, 52, 56, 60, 64, 66, 71, 103, 119, 122, 123, 124, 125, 127, 130, 140, 161, 164, 175, 176, 178, 179, 181, 193, 194, 195, 196, 197, 199, 202, 203, 217, 225, 227, 228, 251, 267, 272, 276, 277, 280, 282, 297, 310, 312, 318, 324, 345, 354, 356, 357, 360, 363, 368, 418, 419, 420, 421, 422, 453, 454, 455, 457, 458, 459, 494, 495, 496, 500, 501, 502, 503, 504, 550, 551, 552, 604, 605, 606, 607, 608, 640, 641, 642, 644, 645, 646, 683, 684, 685, 690, 691, 692, 693, 694, 739, 740, and 741 of the amino acid sequence of an alkaline cellulase set forth in SEQ ID NO: 2 or of the amino acid sequence of an alkaline cellulase having at least 70% identity with the amino acid sequence of SEQ ID NO: 2, with other amino acid residue.

[22] The method according to the above item [21], wherein the at least one amino acid residue is a glutamine residue at the position according to the position 58 of the amino acid sequence of an alkaline cellulase set forth in SEQ ID NO: 2 or of the amino acid sequence having at least 90% identity with the amino acid sequence of SEQ ID NO: 2.

[23] The method according to the above item [21], wherein the at least one amino acid residue is selected from non-charged amino acid residues at the positions corresponding to positions 45, 52, 56, 60, 64, 66, 71, 103, 119, 122, 123, 124, 125, 127, 130, 140, 161, 164, 175, 176, 178, 179, 181, 193, 194, 195, 196, 197, 199, 202, 203, 217, 225, 227, 228, 251, 267, 272, 276, 277, 280, 282, 297, 310, 312, 318, 324, 345, 354, 356, 357, 360, 363, and 368 of the amino acid sequence set forth in SEQ ID NO: 2.

[24] The method according to the above item [21], wherein the at least one amino acid residue is selected from the amino acid residues at the positions corresponding to positions 418, 419, 420, 421, 422, 453, 454, 455, 457, 458, 459, 494, 495, 496, 500, 501, 502, 503, 504, 550, 551, 552, 604, 605, 606, 607, 608, 640, 641, 642, 644, 645, 646, 683, 684, 685, 690, 691, 692, 693, 694, 739, 740, and 741 of the amino acid sequence set forth in SEQ ID NO: 2.

[25] A method for enhancing the anti-redeposition ability of an alkaline cellulase, or method for both enhancing the anti-redeposition ability and protease resistance of an alkaline cellulase, wherein a glutamine residue at the position corresponding to position 58 of the amino acid sequence of an alkaline cellulase set forth in SEQ ID NO: 2 or of the amino acid sequence having at least 90% identity with the amino acid sequence of SEQ ID NO: 2, is substituted with glutamic acid or arginine.

BRIEF DESCRIPTION OF DRAWINGS

FIG. 2A illustrates the results of comparing S237 cellulase with other hydrolases, and FIG. 2B illustrates the results of comparing S237 cellulase with other cellulases.

DESCRIPTION OF EMBODIMENTS

Figure 1:
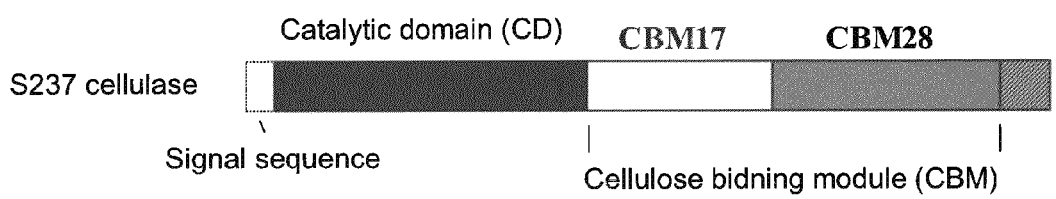
FIG. 1 is a schematic diagram of (A) the structure of S237 cellulase, and (B) a speculated mechanism of the effect of preventing redeposition by a cellulase. The signal sequence illustrated in FIG. 1A is usually cut and removed in a mature protein of S237 cellulase.
Figure 1:
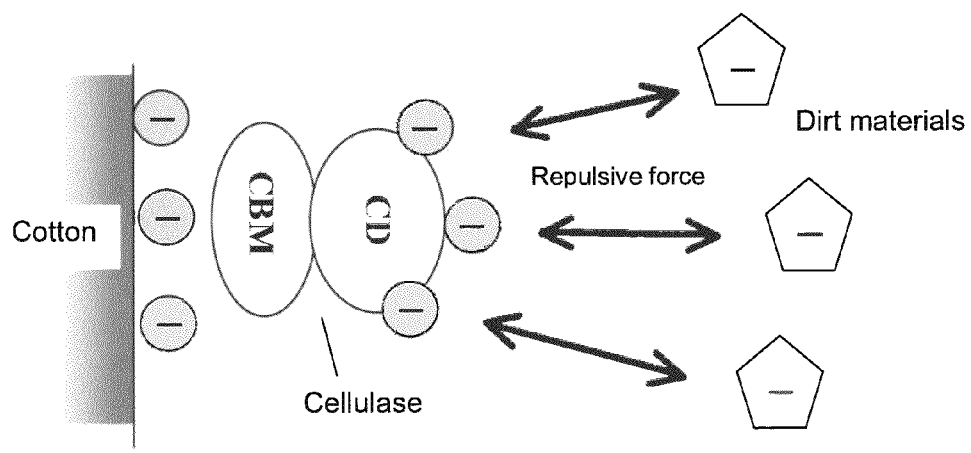

The details of the mechanism for prevention of redeposition by cellulases are not clearly known, and in regard to a method for obtaining a cellulase having higher anti-redeposition ability is not yet known. Furthermore, a problem of cellulases being susceptible to degradation by co-existing proteases is known. Thus, further improvement is needed.

The present invention relates to provision of a mutant alkaline cellulase having enhanced anti-redeposition ability, and a mutant alkaline cellulase having enhanced anti-redeposition ability and protease resistance.

The inventors of the present invention conducted a thorough investigation in order to address the problems described above, and as a result, the inventors found that when an amino acid residue at a predetermined position in a *Bacillus* sp. strain KSM-S237-derived alkaline cellulase is substituted with other amino acid residue, the anti-redeposition ability can be enhanced, and in some mutant alkaline cellulases, both anti-redeposition ability and protease resistance can be enhanced.

Furthermore, the inventors of the present invention found that when a non-charged amino acid residue at a predetermined position exposed to the enzyme surface in the catalytic domain of an alkaline cellulase is substituted with a charged amino acid residue so as to increase hydrophilicity of the enzyme surface of the relevant alkaline cellulase, the anti-redeposition ability of the alkaline cellulase can be remarkably enhanced.

Furthermore, the inventors of the present invention found that when an amino acid residue in a region that participates in cellulose binding or the vicinity thereof in the cellulose binding module of an alkaline cellulase is substituted so as to weaken the cellulose binding properties, the anti-redeposition ability of the alkaline cellulase can be further enhanced.

The mutant alkaline cellulase having enhanced anti-redeposition ability according to the present invention, and an anti-redeposition agent containing the mutant alkaline cellulase can bring about a high anti-redeposition promoting effect in, for example, a washing process. The enzyme composition according to the present invention can provide an anti-redeposition effect to a cleaning agent composition and the like when incorporated into the cleaning agent composition and the like. The cleaning agent composition according to the present invention can exhibit a high anti-redeposition effect at the time of washing. When the method for producing a mutant alkaline cellulase according to the present invention is used, production of an alkaline cellulase having enhanced anti-redeposition ability is possible. Furthermore, according to the present invention, an alkaline cellulase which has a high anti-redeposition activity, has both a high anti-redeposition activity and high protease resistance, and is useful as an enzyme for incorporation into a cleaning agent, can be provided.

Hereinafter, the present invention will be described in detail.

1. Mutant Alkaline Cellulase and Production Thereof

In the mutant alkaline cellulase of the present invention, at least one amino acid residue selected from the amino acid residues at the positions corresponding to positions 58, 45, 52, 56, 60, 64, 66, 71, 103, 119, 122, 123, 124, 125, 127, 130, 140, 161, 164, 175, 176, 178, 179, 181, 193, 194, 195, 196, 197, 199, 202, 203, 217, 225, 227, 228, 251, 267, 272, 276, 277, 280, 282, 297, 310, 312, 318, 324, 345, 354, 356, 357, 360, 363, 368, 418, 419, 420, 421, 422, 453, 454, 455, 457, 458, 459, 494, 495, 496, 500, 501, 502, 503, 504, 550, 551, 552, 604, 605, 606, 607, 608, 640, 641, 642, 644, 645, 646, 683, 684, 685, 690, 691, 692, 693, 694, 739, 740, and 741 of the amino acid sequence of an alkaline cellulase set forth in SEQ ID NO: 2 or of the amino acid sequence of an alkaline cellulase having at least 70% identity with the amino acid sequence of SEQ ID NO: 2, is substituted with other amino acid residue. The mutant alkaline cellulase of the present invention has enhanced anti-redeposition ability, or has both enhanced anti-redeposition ability and protease resistance, as compared with the alkaline cellulase before mutation (parent alkaline cellulase).

One embodiment of the present invention is a mutant alkaline cellulase which acquires enhanced anti-redeposition ability, or acquires enhanced anti-redeposition ability and protease resistance, by substituting a glutamine residue at the position corresponding to position 58 of the amino acid sequence of an alkaline cellulase set forth in SEQ ID NO: 2 or of the amino acid sequence of an alkaline cellulase having at least 90% identity with the amino acid sequence of SEQ ID NO: 2, with other amino acid.

More specifically, the mutant alkaline cellulase of the present invention acquires enhanced anti-redeposition ability, or acquires both enhanced anti-redeposition ability and protease resistance, by substituting a glutamine residue at the position corresponding to position 58 of the amino acid sequence set forth in SEQ ID NO: 2, with glutamic acid or arginine residue.

Another embodiment of the present invention is a mutant alkaline cellulase which acquires enhanced anti-redeposition ability by substituting a non-charged amino acid residue at a particular position in the catalytic domain of any parent alkaline cellulase, with a charged amino acid residue.

More specifically, the mutant alkaline cellulase according to the present invention is a mutant alkaline cellulase obtainable by introducing an amino acid substitution into the amino acid sequence of an available alkaline cellulase, which may be an alkaline cellulase derived from a bacterium of the genus *Bacillus*, such as *Bacillus* sp. strain KSM-S237, or an alkaline cellulase having a high amino acid sequence identity with the foregoing alkaline cellulase, which acquires enhanced anti-redeposition ability by substituting a non-charged amino acid residue that is particularly selected among the non-charged amino acid residues exposed to the enzyme surface in the catalytic domain of the alkaline cellulase with a charged amino acid residue.

Even more specifically, the mutant alkaline cellulase according to the present invention acquires enhanced anti-redeposition ability, by substituting at least one amino acid residue selected from the non-charged amino acid residues at the positions corresponding to positions 45, 52, 56, 60, 64, 66, 71, 103, 119, 122, 123, 124, 125, 127, 130, 140, 161, 164, 175, 176, 178, 179, 181, 193, 194, 195, 196, 197, 199, 202, 203, 217, 225, 227, 228, 251, 267, 272, 276, 277, 280, 282, 297, 310, 312, 318, 324, 345, 354, 356, 357, 360, 363, and 368 of the amino acid sequence of an alkaline cellulase set forth in SEQ ID NO: 2 or of an amino acid of an alkaline cellulase having at least 70% identity with the amino acid sequence of SEQ ID NO: 2, with a charged amino acid residue.

Another embodiment of the present invention is a mutant alkaline cellulase which has enhanced anti-redeposition ability, by substituting an amino acid residue in the region that directly participates in cellulose binding, or a region adjacent thereto, in the cellulose binding module of an available parent alkaline cellulase.

More specifically, the mutant alkaline cellulase according to the present invention is a mutant alkaline cellulase obtainable by introducing an amino acid substitution into the amino acid sequence of an available alkaline cellulase, which may be an alkaline cellulase derived from a bacterium of the genus *Bacillus*, such as *Bacillus* sp. strain KSM-S237, or an alkaline cellulase having high identity of amino acid sequence with that of the foregoing alkaline cellulase, which acquires enhanced anti-redeposition ability by substituting an amino acid residue in the region that directly participates in cellulose binding or a region in the vicinity thereof in the cellulose binding module of the alkaline cellulase, with other amino acid residue.

Even more specifically, the mutant alkaline cellulase according to the present invention acquires enhanced anti-redeposition ability by substituting at least one amino acid residue selected from the amino acid residues at the positions corresponding to positions 418, 419, 420, 421, 422, 453, 454, 455, 457, 458, 459, 494, 495, 496, 500, 501, 502, 503, 504, 550, 551, 552, 604, 605, 606, 607, 608, 640, 641, 642, 644, 645, 646, 683, 684, 685, 690, 691, 692, 693, 694, 739, 740, and 741 of the amino acid sequence of an alkaline cellulase set forth in SEQ ID NO: 2 or of the amino acid sequence of an alkaline cellulase having at least 70% identity with the amino acid sequence of SEQ ID NO: 2, with other amino acid residue.

In the present specification, an original alkaline cellulase, that is, an available alkaline cellulase before amino acid substitution, is referred to as a "parent alkaline cellulase", the amino acid sequence thereof is referred to as a "parent amino acid sequence", and the gene encoding the alkaline cellulase is referred to as a "parent alkaline cellulase gene".

The term amino acid residue as used in the present invention means twenty kinds of amino acid residues constituting proteins, namely, Ala, Arg, Asn, Asp, Cys, Gln, Glu, Gly, His, Ile, Leu, Lys, Met, Phe, Pro, Ser, Thr, Trp, Tyr and Val.

The term non-charged amino acid as used in the present invention means amino acids that do not have a charge among the twenty kinds of amino acids constituting proteins, that is, non-polar amino acids (valine, alanine, leucine, isoleucine, methionine, phenylalanine, tryptophan, and proline) and polar amino acids (glycine, asparagine, cysteine, glutamine, serine, threonine, and tyrosine). The non-charged amino acid residue that may be subjected to an amino acid substitution in the present invention may be any non-polar amino acid or polar amino acid, and the non-charged amino acid residue is more preferably alanine, serine, glutamine or asparagine.

Furthermore, the term charged amino acid as used in the present invention means amino acids having a charge among the twenty amino acids constituting proteins, that is, acidic amino acids (aspartic acid and glutamic acid), and basic amino acids (arginine, histidine and lysine). The charged amino acid residue that is introduced into the mutant alkaline cellulase by substituting a non-charged amino acid residue in the present invention may be any acidic amino acid or basic amino acid, and the charged amino acid residue is preferably glutamic acid, aspartic acid or arginine.

According to the present invention, the identity between amino acid sequences refers to the proportion (%) of the number of positions at which amino acid residues are identical between two aligned amino acid sequences, relative to the number of full-length amino acid residues. Specifically, the identity is calculated by the Lipman-Pearson method; Science, 227, 1435 (1985)), and can be computed by performing an analysis using a homology analysis program (Search homology) of the genetic information processing software, Genetyx-Win (Ver. 5.1.1; Software Development, Inc.) by setting the unit size to compare (ktup) at 2.

The amino acid sequence of the mutant alkaline cellulase according to the present invention can be designed by using the amino acid sequence of any available alkaline cellulase as a parent. Examples of such a parent amino acid sequence include the amino acid sequences of the various alkaline cellulases belonging to family 5 of the glycoside hydrolase family. Furthermore, examples of the parent amino acid sequence include the amino acid sequences of alkaline cellulases derived from any available organisms producing alkaline cellulases, such as bacteria of the genus *Bacillus*, bacteria of the genus *Clostridium*, and bacteria of the genus *Acidothermus*. Among these, an amino acid sequence of an alkaline cellulase derived from a bacterium of the genus *Bacillus* can be favorably used.

A suitable example of the alkaline cellulase of a bacterium of the genus *Bacillus* includes *Bacillus* sp. strain KSM-S237-derived alkaline cellulase [S237 cellulase]. The *Bacillus* sp. strain KSM-S237-derived alkaline cellulase, as a precursor protein containing an N-terminal signal sequence (positions 1 to 30 of SEQ ID NO: 2; MMLRKKTKQLISSILILV-LLLSLFPAALAA [one-character notation of amino acids]), has the amino acid sequence set forth in SEQ ID NO: 2, and as a mature protein has an amino acid sequence obtained by removing the signal sequence from the amino acid sequence of SEQ ID NO: 2.

Accordingly, examples of the parent amino acid sequence of the mutant alkaline cellulase according to the present invention include the amino acid sequence set forth in SEQ ID NO: 2, as well as amino acid sequences having at least 70% identity, preferably at least 80% identity, more preferably at least 90% identity, even more preferably at least 95% identity, even more preferably at least 96% identity, and even more preferably at least 98% identity, with the amino acid sequence set forth in SEQ ID NO: 2. These amino acid sequences may be amino acid sequences encoded in the open reading frame (ORF), or may be amino acid sequences obtained by removing the signal sequence from the foregoing amino acid sequences.

Examples of the alkaline cellulase of a bacterium of the genus *Bacillus* other than S237 cellulase include alkaline cellulases derived from various *Bacillus* bacterial strains, such as *Bacillus* sp. strain DSM12648-derived alkaline cellulase (SEQ ID NO: 4) [the identity of amino acid sequence with that of S237 cellulase (including the signal sequence) is about 98.2%], *Bacillus* sp. strain 1139-derived alkaline cellulase (SEQ ID NO: 6) [the identity of amino acid sequence with that of S237 cellulase (including the signal sequence) is about 91.3%], *Bacillus* sp. strain KSM-64-derived alkaline cellulase (SEQ ID NO: 8) [the identity of amino acid sequence with that of S237 cellulase (including the signal sequence) is about 91.6%], *Bacillus* sp. strain KSM-635-derived alkaline cellulase (SEQ ID NO: 10) [the identity of amino acid sequence with that of S237 cellulase (including the signal sequence) is about 71.0%], and *Bacillus* sp. strain N-4-derived alkaline cellulase (SEQ ID NO: 12) [the identity of amino acid sequence with that of S237 cellulase (including the signal sequence) is about 64.0%], as well as two kinds of alkaline cellulases such as N131a and N131b derived from *Bacillus* sp. strain KSM-N131 (JP-A No. 2001-231569) [the identity of amino acid sequence with that of S237 cellulase (including the signal sequence) is 87.9% and 97.1%, respectively]. These alkaline cellulases have high mutual amino acid sequence identity and similarity.

Therefore, examples of the parent amino acid sequence of the mutant alkaline cellulase according to the present invention include the amino acid sequences of *Bacillus* sp. strain DSM12648-derived alkaline cellulase (SEQ ID NO: 4), *Bacillus* sp. strain 1139-derived alkaline cellulase (SEQ ID NO: 6), *Bacillus* sp. strain KSM-64-derived alkaline cellulase (SEQ ID NO: 8), *Bacillus* sp. strain KSM-635-derived alkaline cellulase (SEQ ID NO: 10), and *Bacillus* sp. strain N-4-derived alkaline cellulase (SEQ ID NO: 12), as well as amino acid sequences having at least 90% identity, preferably at least 95% identity, more preferably at least 96% identity, and even more preferably at least 98% identity, with the aforementioned amino acid sequences.

Alternatively, when the mutant alkaline cellulase according to the present invention is a variant in which the amino acid residue at the position corresponding to position 58 has been substituted ($58^{th}$ position variant), examples of the parent amino acid sequence of the variant include the amino acid sequence of *Bacillus* sp. strain KSM-S237-derived alkaline cellulase as set forth in SEQ ID NO: 2, as well as amino acid sequences having at least 90% identity, more preferably at least 95% identity, even more preferably at least 96% identity, and even more preferably at least 98% identity, with the amino acid sequence set forth in SEQ ID NO: 2.

Examples of a parent alkaline cellulase derived from a bacterium of the genus *Bacillus* other than S237 cellulase, which has an amino acid sequence having at least 90% identity with the amino acid sequence of SEQ ID NO: 2, include the alkaline cellulases having the amino acid sequences set forth in SEQ ID NO: 4, SEQ ID NO: 6 and SEQ ID NO: 8, and the alkaline cellulases derived from various *Bacillus* bacterial strains, such as *Bacillus* sp. strain KSM-N131-derived alkaline cellulase N131b.

The parent amino acid sequence of position 58 variant may be an amino acid sequence encoded in the open reading frame (ORF), or may also be an amino acid sequence having the signal sequence (positions 1 to 30 of SEQ ID NO: 2) removed from the foregoing amino acid sequence.

Furthermore, the parent amino acid sequence according to the present invention may also include amino acid sequences having a deletion, substitution or addition of one or several amino acids with respect to each of the amino acid sequences of SEQ ID NOs: 2, 4, 6, 8, 10 and 12. The "one or several" refers to, hereinafter for example, 1 to 50 amino acids, preferably 1 to 30 amino acids, more preferably 1 to 20 amino acids, even more preferably 1 to 10 amino acids, and even more preferably 1 to 5 amino acids. Examples of such a parent amino acid sequence include, but are not limited to, the amino acid sequences of a mutant alkaline cellulase in which the amino acid residue at the position corresponding to position 10 of the amino acid sequence set forth in SEQ ID NO: 2 has been substituted with glutamine, alanine, proline or methionine; a mutant alkaline cellulase in which the amino acid residue at the position corresponding to position 16 has been substituted with asparagine or arginine; a mutant alkaline cellulase in which the amino acid residue at the position corresponding to position 22 has been substituted with proline; a mutant alkaline cellulase in which the amino acid residue at the position corresponding to position 33 has been substituted with histidine; a mutant alkaline cellulase in which the amino acid residue at the position corresponding to position 39 has been substituted with alanine, threonine or tyrosine; a mutant alkaline cellulase in which the amino acid residue at the position corresponding to position 76 has been substituted with histidine, methionine, valine, threonine or alanine; a mutant alkaline cellulase in which the amino acid residue at the position corresponding to position 109 has been substituted with isoleucine, leucine, serine or valine; a mutant alkaline cellulase in which the amino acid residue at the position corresponding to position 242 has been substituted with alanine, phenylalanine, valine, serine, aspartic acid, glutamic acid, leucine, isoleucine, tyrosine, threonine, methionine or glycine; a mutant alkaline cellulase in which the amino acid residue at the position corresponding to position 263 has been substituted with isoleucine, leucine, proline or valine; a mutant alkaline cellulase in which the amino acid residue at the position corresponding to position 308 has been substituted with alanine, serine, glycine or valine; a mutant alkaline cellulase in which the amino acid residue at the position corresponding to position 462 has been substituted with threonine, leucine, phenylalanine or arginine; a mutant alkaline cellulase in which the amino acid residue at the position corresponding to position 466 has been substituted with leucine, alanine or serine; a mutant alkaline cellulase in which the amino acid residue at the position corresponding to position 468 has been substituted with alanine, aspartic acid, glycine or lysine; a mutant alkaline cellulase in which the amino acid residue at the position corresponding to position 552 has been substituted with methionine; a mutant alkaline cellulase in which the amino acid residue at the position corresponding to position 564 has been substituted with valine, threonine or leucine; a mutant alkaline cellulase in which the amino acid residue at the position corresponding to position 608 has been substituted with isoleucine or arginine; and the mutant alkaline cellulases disclosed in Patent Documents 2 and 3, such as mutant alkaline cellulases having combinations of one or more of the substitutions of amino acid residues described above. Among the amino acid sequences described above, preferred examples include the amino acid sequences of alkaline cellulases having a mutation in which the amino acid residue at position 242 of the amino acid sequence set forth in SEQ ID NO: 2 has been substituted with other amino acid residues. A more preferred example includes the amino acid sequence of an alkaline cellulase having a mutation in which the glutamine residue at position 242 of the amino acid sequence set forth in SEQ ID NO: 2 has been substituted with a serine residue.

According to the present invention, in the parent amino acid sequences such as described above, one or more amino acid residues selected from the amino acid residues at the positions corresponding to positions 58, 45, 52, 56, 60, 64, 66, 71, 103, 119, 122, 123, 124, 125, 127, 130, 140, 161, 164, 175, 176, 178, 179, 181, 193, 194, 195, 196, 197, 199, 202, 203, 217, 225, 227, 228, 251, 267, 272, 276, 277, 280, 282, 297, 310, 312, 318, 324, 345, 354, 356, 357, 360, 363, 368, 418, 419, 420, 421, 422, 453, 454, 455, 457, 458, 459, 494, 495, 496, 500, 501, 502, 503, 504, 550, 551, 552, 604, 605, 606, 607, 608, 640, 641, 642, 644, 645, 646, 683, 684, 685, 690, 691, 692, 693, 694, 739, 740, and 741 of the amino acid sequence of an alkaline cellulase set forth in SEQ ID NO: 2 or of the amino acid sequence of an alkaline cellulase having at least 70% identity with the amino acid sequence of SEQ ID NO: 2, can be substituted with other amino acid residues.

According to an exemplary embodiment of the present invention, in the parent amino acid sequences such as described above, the glutamine residue at the position corresponding to position 58 of the amino acid sequence SEQ ID NO: 2 is substituted with other amino acid.

Preferably, the glutamine residue at the position corresponding to position 58 of the amino acid sequence of an alkaline cellulase set forth in SEQ ID NO: 2 or of the amino acid sequence of an alkaline cellulase having an amino acid sequence having at least 90% identity with the amino acid sequence of SEQ ID NO: 2, may be substituted with glutamic acid or arginine residue.

Furthermore, preferably, the mutant alkaline cellulase of the present invention may have an amino acid sequence in which the glutamine residue at the position corresponding to position 58 of the amino acid sequence set forth in SEQ ID NO: 2 in the amino acid sequence of an alkaline cellulase having a substitution of one or several amino acid residues of the amino acid sequence set forth in SEQ ID NO: 2 by other amino acid residues, is substituted with other amino acid residue. For example, the mutant alkaline cellulase of the present invention may have an amino acid sequence in which the glutamine residue at the position corresponding to position 58 of the amino acid sequence set forth in SEQ ID NO: 2 in the amino acid sequence of a mutant alkaline cellulase having a mutation of substitution of 1 to 20 amino acid residues, preferably 1 to 10 amino acid residues, and more preferably 1 to 5 amino acid residues, by other amino acid residues with respect to the amino acid residues of an alkaline cellulase having the amino acid sequence set forth in SEQ ID NO: 2, is substituted with glutamic acid or arginine residue.

More preferably, the mutant alkaline cellulase of the present invention may have an amino acid sequence in which the glutamine residue at the position corresponding to position 58 of the amino acid sequence set forth in SEQ ID NO: 2 in the amino acid sequence of a mutant alkaline cellulase having a mutation of substitution of the amino acid residue at position 242 in an alkaline cellulase having the amino acid sequence set forth in SEQ ID NO: 2 by other amino acid residue, is substituted with other amino acid residue.

Even more preferably, the mutant alkaline cellulase of the present invention may have an amino acid sequence in which the glutamine residue at position 58 of the amino acid sequence set forth in SEQ ID NO: 2 in the amino acid sequence of a mutant alkaline cellulase having a mutation of substitution of the glutamine residue at position 242 of the amino acid sequence set forth in SEQ ID NO: 2 by a serine residue, is substituted with glutamic acid or arginine.

According to another exemplary embodiment of the present invention, in the parent amino acid sequences such as described above, one or more amino acid residues selected from the non-charged amino acid residues at the positions corresponding to positions 45, 52, 56, 60, 64, 66, 71, 103, 119, 122, 123, 124, 125, 127, 130, 140, 161, 164, 175, 176, 178, 179, 181, 193, 194, 195, 196, 197, 199, 202, 203, 217, 225, 227, 228, 251, 267, 272, 276, 277, 280, 282, 297, 310, 312, 318, 324, 345, 354, 356, 357, 360, 363, and 368 of the amino acid sequence set forth in SEQ ID NO: 2, may be subjected to a substitution by charged amino acid residues.

Preferably, one or more amino acid residues selected from the non-charged amino acid residues at the positions corresponding to positions 45, 52, 56, 60, 64, 66, 71, 103, 119, 122, 123, 124, 125, 127, 130, 140, 161, 164, 175, 176, 178, 179, 181, 193, 194, 195, 196, 197, 199, 202, 203, 217, 225, 227, 228, 251, 267, 272, 276, 277, 280, 282, 297, 310, 312, 318, 324, 345, 354, 356, 357, 360, 363, and 368 of the amino acid sequence of an alkaline cellulase set forth in SEQ ID NO: 2 or of the amino acid sequence of an alkaline cellulase having at least 70% identity with the amino acid sequence of SEQ ID NO: 2, may be subjected to a substitution by charged amino acid residues.

Furthermore, preferably, the mutant alkaline cellulase of the present invention may have an amino acid sequence in which one or more amino acid residues selected from the non-charged amino acid residues at the positions corresponding to positions 45, 52, 56, 60, 64, 66, 71, 103, 119, 122, 123, 124, 125, 127, 130, 140, 161, 164, 175, 176, 178, 179, 181, 193, 194, 195, 196, 197, 199, 202, 203, 217, 225, 227, 228, 251, 267, 272, 276, 277, 280, 282, 297, 310, 312, 318, 324, 345, 354, 356, 357, 360, 363, and 368 of the amino acid sequence set forth in SEQ ID NO: 2 in the amino acid sequence of a mutant alkaline cellulase having a substitution of one or several amino acid residues by other amino acid residues with respect to an alkaline cellulase having the amino acid sequence set forth in SEQ ID NO: 2, are substituted with charged amino acid residues. For example, the mutant alkaline cellulase of the present invention may have an amino acid sequence in which one or more amino acid residues selected from the non-charged amino acid residues at the positions corresponding to positions 45, 52, 56, 60, 64, 66, 71, 103, 119, 122, 123, 124, 125, 127, 130, 140, 161, 164, 175, 176, 178, 179, 181, 193, 194, 195, 196, 197, 199, 202, 203, 217, 225, 227, 228, 251, 267, 272, 276, 277, 280, 282, 297, 310, 312, 318, 324, 345, 354, 356, 357, 360, 363, and 368 of the amino acid sequence set forth in SEQ ID NO: 2 in the amino acid sequence of a mutant alkaline cellulase having a mutation of substitution of 1 to 20 amino acid residues, preferably 1 to 10 amino acid residues, and more preferably 1 to 5 amino acid residues, by other amino acids with respect to the amino acid residues of an alkaline cellulase having the amino acid sequence set forth in SEQ ID NO: 2, are substituted with charged amino acid residues.

More preferably, the mutant alkaline cellulase of the present invention may have an amino acid sequence in which one or more amino acid residues selected from the non-charged amino acid residues at the positions corresponding to positions 45, 52, 56, 60, 64, 66, 71, 103, 119, 122, 123, 124, 125, 127, 130, 140, 161, 164, 175, 176, 178, 179, 181, 193, 194, 195, 196, 197, 199, 202, 203, 217, 225, 227, 228, 251, 267, 272, 276, 277, 280, 282, 297, 310, 312, 318, 324, 345, 354, 356, 357, 360, 363, and 368 of the amino acid sequence set forth in SEQ ID NO: 2 in the amino acid sequence of a mutant alkaline cellulase having a mutation of substitution of the amino acid residue at position 242 in an alkaline cellulase having the amino acid sequence set forth in SEQ ID NO: 2 by other amino acid residue, are substituted with charged amino acid residues.

Even more preferably, the mutant alkaline cellulase of the present invention may have an amino acid sequence in which one or more amino acid residues selected from the non-charged amino acid residues at the positions 45, 52, 56, 60, 64, 66, 71, 103, 119, 122, 123, 124, 125, 127, 130, 140, 161, 164, 175, 176, 178, 179, 181, 193, 194, 195, 196, 197, 199, 202, 203, 217, 225, 227, 228, 251, 267, 272, 276, 277, 280, 282, 297, 310, 312, 318, 324, 345, 354, 356, 357, 360, 363, and 368 of the amino acid sequence set forth in SEQ ID NO: 2 in the amino acid sequence of a mutant alkaline cellulase having a mutation of substitution of the glutamine residue at position 242 of the amino acid sequence set forth in SEQ ID NO: 2 by a serine residue, are substituted with charged amino acid residues.

According to another exemplary embodiment of the present invention, the amino acid residues in the region that directly participates in cellulose binding or a region adjacent thereto in the cellulose binding module in a parent amino acid sequence such as described above, are subjected to substitution.

Preferably, one or more of the amino acid residues at the positions corresponding to positions 418, 419, 420, 421, 422, 453, 454, 455, 457, 458, 459, 494, 495, 496, 500, 501, 502, 503, 504, 550, 551, 552, 604, 605, 606, 607, 608, 640, 641, 642, 644, 645, 646, 683, 684, 685, 690, 691, 692, 693, 694, 739, 740, and 741 of the amino acid sequence of an alkaline cellulase set forth in SEQ ID NO: 2 or of the amino acid sequence of an alkaline cellulase having at least 70% identity with the amino acid sequence of SEQ ID NO: 2, may be subjected to amino acid substitution.

Furthermore, preferably, the mutant alkaline cellulase of the present invention may have an amino acid sequence in which one or more amino acid residues selected from the amino acid residues at the positions corresponding to positions 418, 419, 420, 421, 422, 453, 454, 455, 457, 458, 459, 494, 495, 496, 500, 501, 502, 503, 504, 550, 551, 552, 604, 605, 606, 607, 608, 640, 641, 642, 644, 645, 646, 683, 684, 685, 690, 691, 692, 693, 694, 739, 740, and 741 of the amino acid sequence set forth in SEQ ID NO: 2 in the amino acid sequence of a mutant alkaline cellulase having a substitution of one or several amino acid residues by other amino acid residues with respect to the amino acid residues of an alkaline cellulase having the amino acid sequence set forth in SEQ ID NO: 2, are substituted with other amino acid residues. For example, the mutant alkaline cellulase of the present invention may have an amino acid sequence in which one or more amino acid residues selected from the amino acid residues at the positions corresponding to positions 418, 419, 420, 421, 422, 453, 454, 455, 457, 458, 459, 494, 495, 496, 500, 501, 502, 503, 504, 550, 551, 552, 604, 605, 606, 607, 608, 640, 641, 642, 644, 645, 646, 683, 684, 685, 690, 691, 692, 693, 694, 739, 740, and 741 of the amino acid sequence set forth in SEQ ID NO: 2 in the amino acid sequence of a mutant alkaline cellulase having a mutation of substitution of 1 to 20 amino acid residues, preferably 1 to 10 amino acid residues, and more preferably 1 to 5 amino acid residues, by other amino acids with respect to the amino acid residues of an alkaline cellulase having the amino acid sequence set forth in SEQ ID NO: 2, are substituted with other amino acid residues.

More preferably, the mutant alkaline cellulase of the present invention may have an amino acid sequence in which one or more amino acid residues selected from the amino acid residues at the positions corresponding to positions 418, 419, 420, 421, 422, 453, 454, 455, 457, 458, 459, 494, 495, 496, 500, 501, 502, 503, 504, 550, 551, 552, 604, 605, 606, 607, 608, 640, 641, 642, 644, 645, 646, 683, 684, 685, 690, 691, 692, 693, 694, 739, 740, and 741 of the amino acid sequence set forth in SEQ ID NO: 2 in the amino acid sequence of a mutant alkaline cellulase having a mutation of substitution of the amino acid residue at position 242 of the amino acid sequence set forth in SEQ ID NO: 2 by other amino acid residue, are substituted with other amino acid residues.

Even more preferably, the mutant alkaline cellulase of the present invention may have an amino acid sequence in which one or more amino acid residues selected from the amino acid residues at positions 418, 419, 420, 421, 422, 453, 454, 455, 457, 458, 459, 494, 495, 496, 500, 501, 502, 503, 504, 550, 551, 552, 604, 605, 606, 607, 608, 640, 641, 642, 644, 645, 646, 683, 684, 685, 690, 691, 692, 693, 694, 739, 740, and 741 of the amino acid sequence set forth in SEQ ID NO: 2 in the amino acid sequence of a mutant alkaline cellulase having a mutation of substitution of the glutamine residue at position 242 of the amino acid sequence set forth in SEQ ID NO: 2 by a serine residue, are substituted with other amino acid residues.

The phrase "the position corresponding to position "Y" of the amino acid sequence set forth in SEQ ID NO: "X"" is used to assign a predetermined position of amino acid residue in the amino acid sequence of an available alkaline cellulase when the amino acid sequence of an alkaline cellulase set forth in SEQ ID NO: "X" (for example, the amino acid sequence of S237 cellulase set forth in SEQ ID NO: 2) is used as a reference sequence. For example, the "amino acid residue at the position corresponding to position "Y" of the amino acid sequence set forth in SEQ ID NO: "X"" means the amino acid residue appearing in the Y-th position counted from the first amino acid residue of the amino acid sequence set forth in SEQ ID NO: "X".

On the other hand, in the case of the amino acid sequence ("Z") of an alkaline cellulase other than SEQ ID NO: "X", the "amino acid residue at the position corresponding to position "Y" of the amino acid sequence set forth in SEQ ID NO: "X"" means the amino acid residue in the amino acid sequence "Z", which is aligned with the Y-th amino acid residue counted from the 1$^{st}$ amino acid residue of the amino acid sequence of SEQ ID NO: "X" when the amino acid sequence "Z" is aligned with the amino acid sequence of SEQ ID NO: "X" (that is, aligned in the same column with respect to the alignment). Furthermore, the alignment of the amino acid sequence of SEQ ID NO: "X" and other amino acid sequence may be carried out manually, or the alignment can also be obtained by, for example, using Clustal W multiple alignment program (Thompson, J. D. et al., (1994) Nucleic Acids Res. 22, p. 4673-4680) at a default setting. Clustal W can be used at, for example, the websites of European Bioinformatics Institute (EBI, http://www.ebi.ac.uk/index.html) or the DNA Data Bank of Japan operated by the National Institute of Genetics in Japan (DDBJ, http://www.ddbj.nig.ac.jp/Welcome-j.html).

A person ordinary skilled in the art can further adjust the alignment thus obtained, if necessary, so as to obtain the optimal alignment. It is preferable to determine such an optimal alignment by taking into consideration of the similarity of amino acid sequences or the frequency of the gap that is inserted. Hereinafter, the similarity of amino acid sequences refers to the proportion (%) of the number of positions at which identical or similar amino acid residues are present in both of two amino acid sequences when the amino acid sequences are aligned, relative to the number of full-length amino acid residues. The term similar amino acid residue means an amino acid residue having properties that are similar to each other in terms of polarity or charge and used for so-called conservative substitution, among the twenty kinds of amino acids constituting proteins. Groups composed of such similar amino acid residues are well known to those ordinary skilled in the art, and examples include, but not limited to, arginine and lysine; glutamic acid and aspartic acid; serine and threonine; glutamine and asparagine; and valine, leucine and isoleucine.

When alignment is carried out according to the method described above, the glutamine residue at position 29 in the sequence of SEQ ID NO: 4 (derived from strain DSM12648), the glutamine residue at position 58 in the sequence of SEQ ID NO: 6 (derived from strain 1139), and the glutamine residue at position 57 in the sequence of SEQ ID NO: 8 (derived from strain KSM-64) respectively correspond to the "amino acid residue at the position corresponding to position 58 of the amino acid sequence set forth in SEQ ID NO: 2".

Furthermore, as a reference, the amino acid residues respectively corresponding to the positions described above of the sequence of SEQ ID NO: 2 in the respective amino acid sequences of SEQ ID NO: 2 (derived from *Bacillus* sp. strain KSM-S237), SEQ ID NO: 4 (derived from strain DSM12648), SEQ ID NO: 6 (derived from strain 1139), SEQ ID NO: 8 (derived from strain KSM-64), SEQ ID NO: 10 (derived from strain KSM-635), and SEQ ID NO: 12 (derived from strain N-4), which can be used as the parent amino acid sequences, are shown in Table 5 and Table 6 illustrated below.

According to a preferred exemplary embodiment, the mutant alkaline cellulase according to the present invention includes, for example, a mutant alkaline cellulase having an amino acid sequence that is obtained by substituting the glutamine residue at the position corresponding to position 58 of the amino acid sequence of SEQ ID NO: 2 and of an amino acid sequence having at least 90% identity with the amino acid sequence of SEQ ID NO: 2, with glutamic acid or arginine residue; and having an amino acid sequence that is obtained by further removing a signal sequence (corresponding to a sequence including the positions 1 to 30 of SEQ ID NO: 2) from the foregoing sequence. The substitution described above provides remarkably high anti-redeposition ability, or provides both remarkably high anti-redeposition ability and high protease resistance, to the mutant alkaline cellulase.

A preferred example of the mutant alkaline cellulase of the present invention according to this exemplary embodiment includes a mutant alkaline cellulase having an amino acid sequence that is obtained by substituting the glutamine residue at position 58 of the amino acid sequence set forth in SEQ ID NO: 2 with glutamic acid and arginine; and having an amino acid sequence that is obtained by further removing the signal sequence from the foregoing sequence.

Another preferred example includes a mutant alkaline cellulase having an amino acid sequence that is obtained by substituting the glutamine residue at position 58 in the amino acid sequence of a mutant alkaline cellulase having a mutation of substitution of the glutamine residue at position 242 of the amino acid sequence set forth in SEQ ID NO: 2 by a serine residue, with glutamic acid or arginine residue; and having an amino acid sequence that is obtained by further removing the signal sequence from the foregoing sequence.

Another preferred example includes a mutant alkaline cellulase having an amino acid sequence that is obtained by substituting the glutamine residue at position 29 of the amino acid sequence of SEQ ID NO: 4 in the amino acid sequence set forth in SEQ ID NO: 4, with glutamic acid or arginine residue; and having an amino acid sequence that is obtained by further removing the signal sequence from the foregoing sequence.

Another preferred example includes a mutant alkaline cellulase having an amino acid sequence that is obtained by substituting the glutamine residue at position 58 of the amino acid sequence of SEQ ID NO: 4 in the amino acid sequence set forth in SEQ ID NO: 6, with glutamic acid or arginine residue; and an amino acid sequence that is obtainable by further removing the signal sequence from the foregoing sequence.

Another preferred example includes a mutant alkaline cellulase having an amino acid sequence that is obtained by substituting the glutamine residue at position 57 of the amino acid sequence of SEQ ID NO: 4 in the amino acid sequence set forth in SEQ ID NO: 8, with glutamic acid or arginine residue; and having an amino acid sequence that is obtained by further removing the signal sequence from the foregoing sequence.

According to another preferred exemplary embodiment, the mutant alkaline cellulase related to the present invention includes, for example, in a mutant alkaline cellulase having the amino acid sequence set forth in SEQ ID NO: 2 or an amino acid sequence having at least 70% identity with the amino acid sequence of SEQ ID NO: 2, the mutant alkaline cellulase having an amino acid sequence that is obtained by substituting a non-charged amino acid residue at a particular position in the catalytic domain with a charged amino acid residue, and having an amino acid sequence that is obtained by further removing a signal sequence (corresponding to a sequence including the positions 1 to 30 of SEQ ID NO: 2) from the foregoing sequence.

The mutant alkaline cellulase according to the above exemplary embodiment exhibits anti-redeposition ability based on the high hydrophilicity of the enzyme surface and the overall structure of the enzyme. Therefore, in the case of using the mutant alkaline cellulase simply for the purpose of obtaining an anti-redeposition effect, it makes no difference whether the mutant alkaline cellulase has cellulase activity or not. However, from the viewpoint that a glycolytic activity against saccharides including cellulose can also be simultaneously obtained, it is more preferable that the mutant alkaline cellulase related to the present invention has cellulase activity. The relevant mutant alkaline cellulase may have a signal sequence at the N-terminal, or may be in the form of a mature protein having the signal sequence removed therefrom.

In the mutant alkaline cellulase according to the exemplary embodiment described above, the substitution of a non-charged amino acid residue in the catalytic domain with a charged amino acid residue is not limited, and for example, the substitution may be a substitution of alanine, serine, glutamine or asparagine with glutamic acid, aspartic acid or arginine. Such a substitution provides remarkably high anti-redeposition ability to the mutant alkaline cellulase according to the present invention.

A preferred example of the mutant alkaline cellulase in this exemplary embodiment may be a mutant alkaline cellulase in which the non-charged amino acid residue at position 71 in the amino acid sequence set forth in SEQ ID NO: 2 (this is the position of an amino acid residue adjacent to an acidic amino acid) is substituted with an acidic amino acid residue. Such a substitution particularly efficiently increases the hydrophilicity in the vicinity of the substituted amino acid residue, and provides remarkably high anti-redeposition ability to the resulting mutant alkaline cellulase.

Another preferred example may be a mutant alkaline cellulase in which the non-charged amino acid residue of position 71 (this is the position of an amino acid residue adjacent to an acidic amino acid) in the amino acid sequence of a mutant alkaline cellulase having a mutation of substitution of the glutamine residue at position 242 of the amino acid sequence set forth in SEQ ID NO: 2 by a serine residue, with an acidic amino acid residue. Such a substitution particularly efficiently increases the hydrophilicity in the vicinity of the substituted amino acid residue, and provides remarkably high anti-redeposition ability to the resulting mutant alkaline cellulase.

Another preferred example may be a mutant alkaline cellulase in which the non-charged amino acid residue at position 193 in the amino acid sequence set forth in SEQ ID NO: 2 (this is the position where there is an amino acid residue which is not adjacent to an acidic amino acid) is substituted with a basic amino acid residue. Such substitution particularly efficiently increases the hydrophilicity in the vicinity of the substituted amino acid residue, and provides remarkably high anti-redeposition ability to the resulting mutant alkaline cellulase.

Another preferred example may be a mutant alkaline cellulase in which the non-charged amino acid residue at position 193 (this is the position where there is an amino acid residue which is not adjacent to an acidic amino acid) in the amino acid sequence of a mutant alkaline cellulase having a mutation of substitution of the glutamine residue at position 242 of the amino acid sequence set forth in SEQ ID NO: 2 with a serine residue, is substituted with a basic amino acid residue. Such a substitution particularly efficiently increases the hydrophilicity in the vicinity of the substituted amino acid residue, and provides remarkably high anti-redeposition ability to the resulting mutant alkaline cellulase.

As another preferred example, the mutant alkaline cellulase according to the present invention includes, for example, a mutant alkaline cellulase having an amino acid sequence that is obtained by substituting one or more amino acid residues selected from the non-charged amino acid residues at the positions corresponding to positions 45, 52, 56, 60, 64, 66, 71, 103, 119, 122, 123, 124, 125, 127, 130, 140, 161, 164, 175, 176, 178, 179, 181, 193, 194, 195, 196, 197, 199, 202, 203, 217, 225, 227, 228, 251, 267, 272, 276, 277, 280, 282, 297, 310, 312, 318, 324, 345, 354, 356, 357, 360, 363, and 368 of the amino acid sequence of SEQ ID NO: 2 and of an amino acid sequence having at least 90% identity with the amino acid sequence of SEQ ID NO: 2, with charged amino acid residues, and having an amino acid sequence that is obtained by further removing a signal sequence (corresponding to a sequence including the positions 1 to 30 of the sequence of SEQ ID NO: 2) from the foregoing sequence.

Another preferred example includes a mutant alkaline cellulase having an amino acid sequence that is obtained by substituting one or more amino acid residues selected from the non-charged amino acid residues at the positions corresponding to positions 16, 23, 27, 31, 35, 37, 42, 74, 90, 93, 94, 95, 96, 98, 101, 111, 132, 135, 146, 147, 149, 150, 152, 164, 165, 166, 167, 168, 170, 173, 174, 188, 196, 198, 199, 222, 238, 243, 247, 248, 251, 253, 268, 281, 283, 289, 295, 316, 325, 327, 328, 331, 334, and 339 of the amino acid sequence of SEQ ID NO: 4 and of the amino acid sequence having at least 90% identity with the amino acid sequence of SEQ ID NO: 4, with charged amino acid residues, and having an amino acid sequence that is obtained by further removing the signal sequence from the foregoing sequence.

Another preferred example includes a mutant alkaline cellulase having an amino acid sequence that is obtained by substituting one or more amino acid residues selected from the non-charged amino acid residues at the positions corresponding to positions 45, 52, 56, 60, 64, 66, 71, 103, 119, 122, 123, 124, 125, 127, 130, 140, 161, 164, 175, 176, 178, 179, 181, 193, 194, 195, 196, 197, 199, 202, 203, 217, 225, 227, 228, 251, 267, 272, 276, 277, 280, 282, 297, 310, 312, 318, 324, 345, 354, 356, 357, 360, 363, and 368 of the amino acid sequence of SEQ ID NO: 6 and of an amino acid sequence having at least 90% identity with the amino acid sequence of SEQ ID NO: 6, with charged amino acid residues, and having an amino acid sequence that is obtained by further removing the signal sequence from the foregoing sequence.

Another preferred example includes a mutant alkaline cellulase having an amino acid sequence that is obtained by substituting one or more amino acid residues selected from the non-charged amino acid residues at the positions corresponding to positions 44, 51, 55, 59, 63, 65, 70, 102, 118, 121, 122, 123, 124, 126, 129, 139, 160, 163, 174, 175, 177, 178, 180, 192, 193, 194, 195, 196, 198, 201, 202, 216, 224, 226, 227, 250, 266, 271, 275, 276, 279, 281, 296, 309, 311, 317, 323, 344, 353, 355, 356, 359, 362, and 367 of the amino acid sequence of SEQ ID NO: 8 and of an amino acid sequence having at least 90% identity with the amino acid sequence of SEQ ID NO: 8, with charged amino acid residues, and having an amino acid sequence that is obtained by further removing the signal sequence from the foregoing sequence.

Another preferred example includes a mutant alkaline cellulase having an amino acid sequence that is obtained by substituting one or more amino acid residues selected from the non-charged amino acid residues at the positions corresponding to positions 226, 233, 237, 241, 245, 247, 284, 300, 303, 304, 305, 306, 320, 344, 361, 376, 377, 378, 379, 380, 382, 385, 386, 400, 431, 447, 456, 460, 462, 477, 490, 492, 498, 504, 525, 534, 536, 537, and 548 of the amino acid sequence of SEQ ID NO: 10 and of an amino acid sequence having at least 90% identity with the amino acid sequence of SEQ ID NO: 10, with charged amino acid residues, and having an amino acid sequence that is obtained by further removing the signal sequence from the foregoing sequence.

Another preferred example includes a mutant alkaline cellulase having an amino acid sequence that is obtained by substituting one or more amino acid residues selected from the non-charged amino acid residues at the positions corresponding to positions 63, 71, 75, 79, 83, 85, 90, 122, 138, 142, 143, 144, 146, 193, 207, 208, 210, 222, 223, 224, 225, 226, 228, 231, 232, 246, 254, 256, 257, 281, 297, 302, 306, 310, 348, 354, 375, 384, 386, and 387 of the amino acid sequence of SEQ ID NO: 12 and of an amino acid sequence having at least 90% identity with the amino acid sequence of SEQ ID NO: 12, with charged amino acid residues, and having an amino acid sequence that is obtained by further removing the signal sequence from the foregoing sequence.

According to an even more preferred exemplary embodiment, the mutant alkaline cellulase according to the present invention includes, for example, a mutant alkaline cellulase having an amino acid sequence that is obtained by substituting the amino acid residues in the region that directly participates in cellulose binding, and a region adjacent thereto, in the cellulose binding module in an alkaline cellulase having the amino acid sequence set forth in SEQ ID NO: 2 and an amino acid sequence having at least 70% identity with the amino acid sequence of SEQ ID NO: 2, with other amino acid residues, and having an amino acid sequence that is obtained by further removing a signal sequence (corresponding to a sequence including the positions 1 to 30 of SEQ ID NO: 2) from the foregoing sequence.

The mutant alkaline cellulase according to this exemplary embodiment exhibits anti-redeposition ability based on a decrease in the cellulose binding properties at the cellulose binding module of the cellulase. Therefore, in the case of using the mutant alkaline cellulase simply for the purpose of obtaining an anti-redeposition effect, it makes no difference whether the mutant alkaline cellulase may have cellulase activity or not. However, from the viewpoint that a glycolytic activity against saccharides including cellulose can also be simultaneously obtained, it is more preferable that the mutant alkaline cellulase related to the present invention have cellulase activity. The mutant alkaline cellulase according to the present invention may have a signal sequence at the N-terminal, or may be in the form of a mature protein having the signal sequence removed therefrom.

In the mutant alkaline cellulase according to the exemplary embodiment described above, the substitution of an amino acid residue as an object by other amino acid residue may be, for example, a substitution of tryptophan (non-polar amino acid) with tyrosine (polar amino acid), or may be a substitution of an amino acid residue other than tryptophan [that is, as non-polar amino acids, valine, leucine, isoleucine, methionine, phenylalanine and proline; as polar amino acids, glycine, asparagine, cysteine, glutamine, serine, threonine and tyrosine; as acidic amino acids, aspartic acid and glutamic acid; and as basic amino acids, arginine, histidine and lysine] with alanine (non-polar amino acid). Such a substitution provides remarkably high anti-redeposition ability to the mutant alkaline cellulase according to the present invention.

A preferred example of the mutant alkaline cellulase of the present invention in the exemplary embodiment described above is a mutant alkaline cellulase in which one or more amino acid residues selected from the amino acid residues at the positions 419, 421, 454, and 501 of the amino acid sequence set forth in SEQ ID NO: 2 (these are the positions of amino acid residues that directly participate in cellulose binding and their suitable adjacent site (position 640)) are substituted with other amino acid residues. Such a substitution decreases the cellulose binding property in the vicinity of the substituted amino acid residues, and as a result, the substitution brings about a partial decrease in the binding property to cellulose of the resulting mutant alkaline cellulase, while provides remarkably high anti-redeposition ability.

Another preferred example includes a mutant alkaline cellulase in which one or more amino acid residues selected from the amino acid residues at the positions 419, 421, 454 and 501 (these are the positions of amino acid residues that directly participate in cellulose binding and their suitable adjacent site (position 640)) in the amino acid sequence of a mutant alkaline cellulase having a mutation of substitution of the glutamine residue at position 242 of the amino acid sequence set forth in SEQ ID NO: 2 by a serine residue, are substituted with other amino acid residues.

As another preferred example, the mutant alkaline cellulase according to the present invention includes, for example, a mutant alkaline cellulase having an amino acid sequence that is obtained by substituting one or more amino acid residues selected from the amino acid residues at the positions corresponding to positions 418, 419, 420, 421, 422, 453, 454, 455, 457, 458, 459, 494, 495, 496, 500, 501, 502, 503, 504, 550, 551, 552, 604, 605, 606, 607, 608, 640, 641, 642, 644, 645, 646, 683, 684, 685, 690, 691, 692, 693, 694, 739, 740, and 741 of the amino acid sequence of SEQ ID NO: 2 and of an amino acid sequence having at least 90% identity with the amino acid sequence of SEQ ID NO: 2, with other amino acid residues, and having an amino acid sequence that is obtained by further removing a signal sequence (corresponding to a sequence including the positions 1 to 30 of SEQ ID NO: 2) from the foregoing sequence.

Another preferred example includes a mutant alkaline cellulase having an amino acid sequence that is obtained by substituting one or more amino acid residues selected from the amino acid residues at the positions corresponding to positions 389, 390, 391, 392, 393, 424, 425, 426, 428, 429, 430, 465, 466, 467, 471, 472, 473, 474, 475, 521, 522, 523, 523, 575, 576, 577, 578, 579, 611, 612, 613, 615, 616, 617, 654, 655, 656, 661, 662, 664, 665, 710, 711, and 712 of the amino acid sequence of SEQ ID NO: 4 and of an amino acid sequence having at least 90% identity with the amino acid sequence of SEQ ID NO: 4, with other amino acid residues, and having an amino acid sequence that is obtained by further removing the signal sequence from the foregoing sequence.

Another preferred example includes a mutant alkaline cellulase having an amino acid sequence that is obtained by substituting one or more amino acid residues selected from the amino acid residues at the positions corresponding to positions 418, 419, 420, 421, 422, 452, 453, 454, 456, 457, 458, 493, 494, 495, 499, 500, 501, 502, 503, 548, 549, 550, 602, 603, 604, 605, 606, 638, 639, 640, 642, 643, 644, 681, 682, 683, 688, 689, 690, 691, 692, 737, 738, and 739 of the amino acid sequence of SEQ ID NO: 6 and of an amino acid sequence having at least 90% identity with the amino acid sequence of SEQ ID NO: 6, with other amino acid residues, and having an amino acid sequence that is obtained by further removing the signal sequence from the foregoing sequence (the strain 1139-derived cellulase contains a signal sequence consisting of 30 amino acids).

Another preferred example includes a mutant alkaline cellulase having an amino acid sequence that is obtained by substituting one or more amino acid residues selected from the amino acid residues at the positions corresponding to positions 417, 418, 419, 420, 421, 451, 452, 453, 455, 456, 457, 492, 493, 494, 498, 499, 500, 501, 502, 547, 548, 549, 601, 602, 603, 604, 605, 637, 638, 639, 641, 642, 643, 680, 681, 682, 687, 688, 689, 690, 691, 736, 737, and 738 of the amino acid sequence of SEQ ID NO: 8 and of an amino acid sequence having at least 90% identity with the amino acid sequence of SEQ ID NO: 8, with other amino acid residues, and having an amino acid sequence that is obtained by further removing the signal sequence from the foregoing sequence (the strain KSM-64-derived cellulase contains a signal sequence consisting of 29 amino acids).

Another preferred example includes a mutant alkaline cellulase having an amino acid sequence that is obtained by substituting one or more amino acid residues selected from the amino acid residues at the positions corresponding to positions 598, 599, 600, 601, 602, 633, 634, 635, 637, 638, 639, 674, 675, 676, 680, 681, 682, 683, 684, 729, 730, 731, 783, 784, 785, 786, 787, 819, 820, 821, 823, 824, 825, 862, 863, 864, 869, 870, 871, 872, 873, 919, 920, and 921 of the amino acid sequence of SEQ ID NO: 10 and of an amino acid sequence having at least 90% identity with the amino acid sequence of SEQ ID NO: 10, with other amino acid residues, and having an amino acid sequence that is obtained by further removing the signal sequence from the foregoing sequence (the strain KSM-635-derived cellulase contains a signal sequence consisting of 29 amino acids).

Another preferred example includes a mutant alkaline cellulase having an amino acid sequence that is obtained by substituting one or more amino acid residues selected from the amino acid residues at the positions corresponding to positions 451, 452, 453, 454, 455, 486, 487, 488, 490, 491, 492, 527, 528, 529, 533, 534, 535, 536, 537, 583, 584, 585, 639, 640, 641, 642, 643, 675, 676, 677, 679, 680, 681, 720, 721, 722, 727, 728, 729, 730, 731, 775, 776, and 777 of the amino acid sequence of SEQ ID NO: 12 and of an amino acid sequence having at least 90% identity with the amino acid sequence of SEQ ID NO: 12, with other amino acid residues, and having an amino acid sequence that is obtained by further removing the signal sequence from the foregoing sequence (the strain N-4-derived cellulase contains a signal sequence consisting of 28 amino acids).

The mutant alkaline cellulase according to the present invention can be produced by using various technologies for introducing mutation that are known in the pertinent art. For example, the mutant alkaline cellulase according to the present invention can be produced by mutating the nucleotide sequence that encodes an amino acid residue to be substituted in the alkaline cellulase gene that encodes a parent amino acid sequence of the mutant alkaline cellulase (parent alkaline cellulase gene), to a nucleotide sequence that encodes an amino acid residue after substitution, and then expressing the mutant alkaline cellulase from the mutant gene.

The intended introduction of mutation into the parent alkaline cellulase gene can be carried out essentially based on PCR amplification in which the parent alkaline cellulase gene is used as a template DNA, or replication reactions using various DNA polymerases, by using various site-directed mutagenesis methods that are well known to those ordinary skilled in the art. The site-directed mutagenesis method can be carried out by, for example, any technique such as an inverse PCR method or an annealing method (Muramatsu, et al., ed., "New Genetic Engineering Handbook, Revised 4$^{th}$ Edition", Yodosha Co., Ltd., p. 82-88). If necessary, various commercially available kits for site-directed mutagenesis, such as QuickChange II Site-Directed Mutagenesis Kit and QuickChange Multi Site-Directed Mutagenesis Kit by Stratagene, Inc. may be used. In the present invention, a method of preparing DNA fragments by respectively amplifying the upstream side and the downstream side of the mutated site by separately using two complementary mutation primers containing the nucleotide mutations to be introduced, and linking the DNA fragments into one by SOE (splicing by overlap extension)-PCR (Horton R. M. at al., Gene (1989) 77(1), p. 61-68) may be used. The procedure for the introduction of mutation using this SOE-PCR method will be described in detail in the Examples described below.

The template DNA containing the parent alkaline cellulase gene can be prepared by extracting the genomic DNA from a organism that produces an alkaline cellulase by a routine method, or by extracting the RNA and synthesizing a cDNA by reverse transcription. As the organism that produces an alkaline cellulase, bacteria including bacteria of the genus *Bacillus*, such as *Bacillus subtilis*, bacteria of the genus *Clostridium* and bacteria of the genus *Acidothermus*, as well as plants and animals have been reported. However, most advanced studies have been conducted on bacteria of the genus *Bacillus*, such as *Bacillus subtilis*, and those organisms are easily available to those ordinary skilled in the art. For example, *Bacillus* sp. strain KSM-S237 (Accession No. FERM BP-7875), strain KSM-64 (Accession No. FERM BP-2886), and strain KSM-635 (Accession No. FERM BP-1485) have been deposited in the International Patent Organism Depositary, National Institute of Advanced Industrial Science and Technology (Central 6, 1-1-1, Higashi, Tsukuba-shi, Ibaraki-ken, Japan), under the respective indicated accession numbers.

Preparation of the genomic DNA from these bacterial strains of the genus *Bacillus* can be carried out by using, for example, the method described in Pitcher et al., Lett. Appl. Microbiol., 1989, 8:p. 151-156, or the like. The template DNA containing the parent alkaline cellulase gene may be prepared in the form in which a DNA fragment containing the parent alkaline cellulase gene that has been excised from a prepared cDNA or the genomic DNA, is inserted into an available vector. Meanwhile, previously reported DNA sequences (sequences registered in GenBank) including the base sequences encoding *Bacillus* sp. strain KSM-S237-derived alkaline cellulase (SEQ ID NO: 2), strain DMS12648-derived alkaline cellulase (SEQ ID NO: 4), strain 1139-derived alkaline cellulase (SEQ ID NO: 6), strain KSM-64-derived alkaline cellulase (SEQ ID NO: 8), strain KSM-635-derived alkaline cellulase (SEQ ID NO: 10) and strain N-4-derived alkaline cellulase (SEQ ID NO: 12) are set forth in SEQ ID NO: 1 (GenBank Accession No. AB018420), SEQ ID NO: 3, SEQ ID NO: 5 (GenBank Accession No. D00066), SEQ ID NO: 7 (GenBank Accession No. M84963), SEQ ID NO: 9 (GenBank Accession No. M27420), and SEQ ID NO: 11 (GenBank Accession No. M25500), respectively.

The site-directed mutagenesis into the parent alkaline cellulase gene can be carried out, most generally by using a mutation primer containing the nucleotide mutation to be introduced. Such a mutation primer may be annealed into a region containing the nucleotide sequence encoding the amino acid residues to be subjected in the parent alkaline cellulase gene, and may be designed to include a base sequence having the nucleotide sequence (codon) that encodes the amino acid residue after substitution, instead of the nucleotide sequence (codon) that encodes the amino acid residue to be substituted. The nucleotide sequences (codons) that encode the amino acid residues to be substituted and the amino acid residues after substitution can be appropriately recognized and selected by a person ordinary skilled in the art, based on conventional textbooks and the like.

For example, in the case of substituting the glutamine residue at position 58 of S237 cellulase (SEQ ID NO: 2) with an arginine residue, a primer containing a sequence in which the codon CAA (positions 744 to 746 of SEQ ID NO: 1) corresponding to the glutamine has been changed into the arginine codon GAA (Q58R-FW; SEQ ID NO: 30) and a primer having a complementary sequence thereof (Q58R-RV; SEQ ID NO: 29) can be used as the mutation primers.

Furthermore, for example, in the case of substituting alanine at position 56 of S237 cellulase (SEQ ID NO: 2) with aspartic acid, a primer containing a sequence in which the codon GCA (positions 738 to 740 of SEQ ID NO: 1) corresponding to the alanine has been changed to the aspartic acid codon GAT, 5'-TCTGAGGCTGGCGATTTACAATTA-CAAG-3' (A56D-FW; SEQ ID NO: 33) and a primer having a complementary sequence thereof, 5'-CTTGTAATTG-TAAATCGCCAGCCTCAGA-3' (A56D-RV; SEQ ID NO: 34) can be used as the mutation primers.

Furthermore, for example, in the case of substituting asparagine at position 419 of S237 cellulase (SEQ ID NO: 2) with alanine, a primer containing a sequence in which the codon AAT (positions 1827 to 1829 of SEQ ID NO: 1) corresponding to the asparagine has been changed to the alanine codon GCT, 5'-AGGATTTGGAGTGGCTTCGGATTCTCCAAA-3' (N419A-FW; SEQ ID NO: 22) and a primer having a complementary sequence thereof (N419A-RV; SEQ ID NO: 21) can be used as the mutation primers.

The primers used in the present invention can be produced by a well known oligonucleotide synthesis method such as a phosphoroamidite method (Nucleic Acids Research, 17, 7059-7071, 1989). Such synthesis of primers can be carried out by using, for example, a commercially available oligonucleotide synthesizer (manufactured by Applied Biosystems, Inc. or the like). When site-directed mutagenesis such as described above is carried out by using a primer set including mutation primers and using the parent alkaline cellulase gene as a template DNA, a mutant alkaline cellulase gene having the intended mutation introduced therein can be obtained. The present invention relates also to a mutant alkaline cellulase gene that may be obtained as such. Furthermore, the term "mutant alkaline cellulase gene" as used in the present invention means any nucleic acid fragment (including DNA, mRNA, artificial nucleic acid, and the like) encoding the amino acid sequence of a mutant alkaline cellulase. The "gene" according to the present invention may include other base sequences such as an untranslated region (UTR), in addition to an open reading frame.

A recombinant vector can be produced by inserting the mutant alkaline cellulase gene thus obtained into an available vector by a conventional method, and linking the gene to the vector. There are no particular limitations on the vector used in the present invention, and any vector such as a plasmid, a phage, a phagemid, a cosmid, a virus, a YAC vector, or a shuttle vector may be used. Such a vector is more preferably, but not limited to, a vector which can be amplified in bacterial cells, particularly bacterial cells of the genus *Bacillus*, and is even more preferably an expression vector capable of inducing the expression of a transgene in the bacterial cells of the genus *Bacillus*. Among others, a shuttle vector, which is a vector capable of replication even in any of organisms other than bacteria of the genus *Bacillus*, can be particularly suitably used in the recombinant production of a mutant alkaline cellulase. Preferred examples of the vector include, but are not limited to, shuttle vectors such as pHY300PLK (an expression vector capable of transforming both *Escherichia coli* and *Bacillus subtilis*; Ishikawa, H. and Shibahara, H., Jpn. J. Genet., (1985) 60, p. 235-243), and $pAC_3$ (Moriyama, H. et al., Nucleic Acids Res. (1988) 16, p. 8732); plasmids that can be utilized in the transformation of bacteria of the genus *Bacillus*, such as pUB110 (Gryczan, T. J. et al., J. Bacteriol. (1978) 134, p. 318-329), and pTA10607 (Bron, S. et al., Plasmid, 18 (1987), p. 8-15); and secretion vectors capable of adding secretion signals to recombinant proteins (Yamane, et al., "Fusion Protein Produced by *Bacillus subtilis* Secretion Vector", Denpun Kagaku (Starch Science), 34 (1987), p. 163-170). Furthermore, *Escherichia coli*-derived plasmids (for example, pET22b(+), pBR322, pBR325, pUC118, pUC119, pUC18, pUC19, and pBluescript) can also be used.

For the purpose of producing a recombinant mutant alkaline cellulase, the vector is preferably an expression vector. The expression vector may include various elements that are essential to the expression in a host organism (a transcription promoter, a terminator, a ribosome binding site and the like), as well as cis-elements such as a selection marker gene, a polylinker and an enhancer, and useful sequences such as a poly(A) addition signal and a ribosome binding sequence (SD sequence), as necessary.

A transformant can be produced by using a recombinant vector containing the mutant alkaline cellulase gene. In the present invention, when a transformant (transformed cell) is produced by introducing a recombinant vector (specifically, a recombinant expression vector) containing the mutant alkaline cellulase gene according to the present invention into a host cell, and the transformant is cultured under the conditions under which the expression of a recombinant protein is induced, the mutant alkaline cellulase can be produced. The present invention also relates to a transformant produced as such, and a method for producing a mutant alkaline cellulase using the transformant. As the host cell into which a recombinant vector is introduced, microorganisms including bacteria such as *Escherichia coli* and *Bacillus subtilis*, and yeast cells, as well as any cells such as insect cells, animal cells (for example, mammalian cells) and plant cells can be used. According to the present invention, it is particularly preferable to use bacteria of the genus *Bacillus*, such as *Bacillus subtilis*.

Transformation can be carried out by applying well known transformation technologies such as a calcium phosphate method, an electroporation method, a lipofection method, a particle gun method, and a PEG method. Examples of the transformation method applicable to bacteria of the genus *Bacillus* include a competent cell transformation method (Bott, K. F. and Wilson, G. A., J. Bacteriol. (1967) 93, 1925), an electroporation method (Brigidi, P. et al., FEMS Microbiol. Lett. (1990) 55, 135), a protoplast transformation method (Chang, S. and Cohen, S. N., Mol. Gen. Genet., (1979) 168, p. 111-115), and a Tris-PEG method (Takahashi W., et al., J. Bacteriol. (1983) 156, p. 1130-1134).

The transformant for recombinant protein production can be cultured according to methods that are commonly used by those ordinarily skilled in the art. For example, as a medium for culturing a transformant based on a microbial host such as *Escherichia coli* or a yeast cell, any of a natural medium and a synthetic medium may be used as long as it is a medium which contains carbon sources, nitrogen sources, inorganic salts and the like that can be assimilated by the host organism, and can efficiently carry out the culture of the transformant. Ampicillin, tetracyclin and the like may also be added to the medium, in accordance with the type of the drug selection marker. When a microorganism that has been transformed with an expression vector having an inducible promoter is cultured, an inducer may also be added to the medium as necessary. For example, in the case of culturing a bacterium or the like that has been transformed with an expression vector having a Lac promoter, isopropyl-1-thio-β-D-galactoside (IPTG) and the like can be added to the medium, and in the case of culturing a bacterium that has been transformed with an expression vector having a trp promoter, indole acetic acid (IAA) and the like can be added to the medium. There are no particular limitations on the culture conditions, and preferably, the culture is carried out under the conditions suitable for the transformed host organism. For example, in the culture of a *Bacillus subtilis* transformant for producing a recombinant protein, for example, LB medium, 2×YT medium, 2×L-maltose medium, and CSL fermentation medium can be used.

The mutant alkaline cellulase according to the present invention may be expressed from a mutant alkaline cellulase gene or a transcription product thereof, using a cell-free translation system. The "cell-free translation system" is an in vitro transcription/translation system or an in vitro translation system constructed by adding reagents such as amino acids needed for the translation of proteins, to a suspension obtained by mechanically homogenizing the host cells. The mutant alkaline cellulase thus expressed can be acquired from a culture fluid, a cell lysate or a cell-free translation system, by using a general method used for protein purification, for example, centrifugation, ammonium sulfate precipitation, gel chromatography, ion exchange chromatography or affinity chromatography, alone or in appropriate combination. However, a solution such as a culture supernatant or a lysate supernatant separated or concentrated by using centrifugation, an ultrafiltration type filter or the like, can be directly used as a crude enzyme fluid. When the mutant alkaline cellulase thus expressed is not secreted from the cells, the cells may be homogenized, and then separation and purification of the protein may be carried out.

For the mutant alkaline cellulase produced as described above, an enhancement of the anti-redeposition ability can be confirmed by an anti-redeposition ability evaluation method that will be described below.

Furthermore, experiments such as the preparation of the mRNA used in the present invention, production of a cDNA, PCR, RT-PCR, production of a library, ligation into a vector, transformation of cells, determination of the base sequence of DNA, chemical synthesis of nucleic acid, determination of the N-terminal side amino acid sequence of the protein, mutagenesis, and extraction of the protein, can be carried out according to the methods described in conventional manuals for experiment. Examples of such manuals include Molecular Cloning, A laboratory manual (2001) $3^{rd}$ Ed., Sambrook, J. & Russell, D W. Cold Spring Harbor Laboratory Press. Particularly, for the experiment of genetic recombination of *Bacillus subtilis*, for example, reference can be made to general experiment manuals on the genetic manipulation of *Bacillus subtilis*, such as Yoshikawa, Hirofumi, "7.2 *Bacillus subtilis* family" "Genetic Research Method II in Lectures on Biochemical Experiment, $2^{nd}$ series", (1986), Vol. 1, Tokyo Kagakudojin (Tokyo), p. 150-169).

2. Evaluation of Properties of Mutant Alkaline Cellulase (2-1) Anti-Redeposition Ability The mutant alkaline cellulase of the present invention shows enhanced anti-redeposition ability as compared with its parent alkaline cellulase.

The "anti-redeposition ability" of the alkaline cellulase (the mutant alkaline cellulase or the parent alkaline cellulase) according to the present invention means the ability of an alkaline cellulase that is incorporated into an aqueous solution, to prevent hydrophobic (oleophilic) dirty materials that are dispersed in the aqueous solution from re-adhering to substrates such as the clothes present in the aqueous solution. Meanwhile, the "anti-redeposition effect" means an effect in which the re-adhering of hydrophobic (oleophilic) dirty materials dispersed in an aqueous solution to substrates such as clothes in the aqueous solution in the presence of an alkaline cellulase (the mutant alkaline cellulase or the parent alkaline cellulase), and the degree of such an effect.

Preferably, the evaluation of the anti-redeposition ability can be carried out by dispersing carbon black as a model for hydrophobic soot stain in water containing a dissolved cleaning agent composition, adding the mutant alkaline cellulase produced as described above to the dispersion liquid to prepare a washing water, washing a white cotton cloth using the washing water, measuring the reflection ratio at 550 nm of the white cloth after washing, and comparing the reflection ratio with the same reflection ratio of an unwashed white cotton cloth. The details of the procedure of the anti-redeposition ability evaluation method are disclosed in the Examples that are described below. Meanwhile, the water used in the anti-redeposition ability evaluation of the present invention can be prepared by appropriately dissolving $CaCl_2$ and $MgCl_2.6H_2O$ in deionized water.

In the anti-redeposition ability evaluation, the anti-redeposition ratio obtained in various test systems can be calculated by the following formula based on the reflection ratio of a white cotton cloth before washing and after washing.

Anti-redeposition ratio (%)={(Reflection ratio of white cotton cloth after test)/(reflection ratio of white cotton cloth before test)}×100 [Mathematical formula 1]

A value of this redeposition reflection ratio closer to 100% indicates that the amount of redeposition by carbon black is smaller.

Furthermore, the degree of promotion of anti-redeposition (%) as a result of the addition of a mutant alkaline cellulase can be calculated based on the following formula, and on the anti-redeposition ratio calculated for a test system using a washing water to which a mutant alkaline cellulase is added (enzyme-added group) and a test system using a washing water to which a mutant alkaline cellulase is not added (non-enzyme-added group).

Degree of promotion of anti-redeposition by enzyme addition (%)={(Anti-redeposition ratio of enzyme-added group)−(anti-redeposition ratio of non-enzyme-added group)}/{100−(anti-redeposition ratio of non-enzyme-added group)}×100 [Mathematical formula 2]

An increase in this degree of promotion of anti-redeposition (%) indicates that the effect of preventing redeposition by the addition of a mutant alkaline cellulase has greatly improved.

Furthermore, the degree of anti-redeposition ability enhancement (%) for individual mutant alkaline cellulases is calculated by the following formula. Further, the "mutant enzyme" in the following formula refers to the mutant alkaline cellulase, and the control enzyme refers to the parent alkaline cellulase, that is, a wild-type alkaline cellulase or an alkaline cellulase before the introduction of mutation.

Degree of anti-redeposition ability enhancement (%) for mutant alkaline cellulase={(Anti-redeposition ratio of mutant enzyme-added group)−(anti-redeposition ratio of control enzyme-added group)}/{100−(anti-redeposition ratio of control enzyme-added group)}×100 [Mathematical formula 3]

An increase of this degree of anti-redeposition ability enhancement (%) indicates that the anti-redeposition ability of the mutant alkaline cellulase is greatly improved as compared with before the introduction of mutation.

Although there are no limitations, the mutant alkaline cellulase according to the present invention can exhibit a degree of anti-redeposition ability enhancement (%) of, for example, 1% to 25%, usually 2% to 15%, and more generally 3% to 12.5%.

(2-2) Cellulose Binding Property

Furthermore, the mutant alkaline cellulase of the present invention can show decreased cellulose binding property as compared with the parent alkaline cellulase.

The decrease of the cellulose binding property in the mutant alkaline cellulase according to the present invention can be confirmed according to a method similar to the anti-redeposition ability evaluation method that will be described below. Specifically, an evaluation cloth (white cotton cloth) is washed in washing water prepared by adding a predetermined amount of an alkaline cellulase, and sodium chloride in an amount of 5% relative to the total amount of the washing water, to water in which a cleaning agent composition is dissolved, using an agitation-type detergency tester at 20° C. After the washing, the white cloth is taken out and lightly wrung out, and is rapidly introduced into 2000 mL of tap water. Subsequently, the white cloth is taken out and dehydrated without rinsing, and is stained with Coomassie Brilliant Blue. The cloth is lightly wrung out and then immersed in a decolorization solution. The cloth is washed with water and is subjected to finish ironing. Subsequently, the brightness (L value) is measured using a spectrophotometer. A control experiment is carried out by the same procedure, except that a wild-type alkaline cellulase is added to the washing water. A comparison is made for the brightness (L value) of the evaluation clothes after washing thus obtained. This L value decreases along with an increase in the amount of proteins adsorbed to the evaluation cloth. Accordingly, as the L value is higher compared to the L value obtained by adding a wild-type alkaline cellulase, it is shown that the amount of the mutant alkaline cellulase adsorbed to the evaluation cloth is reduced, that is, the cellulose binding property is decreased.

(2-3) Protease Resistance

Furthermore, the mutant alkaline cellulase of the present invention can show enhanced protease resistance as compared with the parent alkaline cellulase.

According to the present invention, the "protease resistance" refers to the stability of the cellulase to protease, which is evaluated by the residual activity of the cellulase in a cleaning agent composition in which various proteases, particularly alkaline proteases, have been incorporated.

Specifically, for example, the protease resistance may be the residual activity (see the following formula) of a cellulase to be evaluated, which is calculated when the cellulase is stored in a cleaning agent composition containing an alkaline protease at 40° C. for 24 hours.

Cellulase residual activity (%)=(Cellulase activity after 24 hours of storage/cellulase activity immediately after preparation)×100  [Mathematical formula 4]

The mutant alkaline cellulase of the present invention exhibits a cellulase residual activity (%) of, for example, 20% to 75%, and usually 50% to 70%, so that the mutant alkaline cellulase exhibits a residual activity enhanced by 15% to 35% as compared with the parent alkaline cellulase.

Therefore, the mutant alkaline cellulase of the present invention having enhanced protease resistance is suitable for use in the co-presence of various proteases. Here, examples of the proteases include commercially available Alcalase, Esperase, Savinase, Everlase, Kannase (registered trademark; Novozymes, Inc.), Properase, Purafect (registered trademark; Genencor, Inc.), and KAP (Kao Corp.).

3. Use of Mutant Alkaline Cellulase

The mutant alkaline cellulase according to the present invention shows high anti-redeposition ability towards hydrophobic dirt materials in an aqueous solution. Therefore, the mutant alkaline cellulase according to the present invention can be advantageously used as an anti-redeposition agent. The anti-redeposition agent may contain any additives such as an inert carrier, a pH adjusting agent, a dispersant, a buffering agent and an antiseptic agent, in addition to the mutant alkaline cellulase. When such an anti-redeposition agent is added to an aqueous solution containing an object to be washed, the redeposition of the object to be washed can be favorably prevented. For example, the anti-redeposition agent according to the present invention can be incorporated in detergents such as detergents for clothing and detergents for domestic use, fabric softeners and the like, and used.

The present invention also provides an enzyme composition containing the mutant alkaline cellulase according to the present invention. The enzyme composition according to the present invention means an enzyme preparation containing the mutant alkaline cellulase as an active ingredient. The enzyme composition according to the present invention may further include, in addition to the mutant alkaline cellulase, hydrolases including proteases, cellulases, β-glucanases, hemicellulases, lipases, peroxidases, laccases, α-amylases, glucoamylases, cutinases, pectinases, reductases, oxidases, phenoloxidases, ligninases, pullulanases, pectate lyases, xyloglucanases, xylanases, pectinacetylesterases, polygalacturonases, rhamnogalacturonases, pectin lyases, other mannanases, pectin methylesterases, cellobiohydrolases, and transglutaminases, as well as mixtures of two or more kinds thereof.

The enzyme composition according to the present invention may also contain other components such as a pH adjusting agent, a buffering agent, an antiseptic, salt, alcohol, sugars, and medium components, in addition to the mutant alkaline cellulase and the other enzymes. The enzyme composition according to the present invention may be in any form such as a powder, granules, or a lyophilized product.

The present invention also provides a cleaning agent composition containing one or more of the mutant alkaline cellulase, anti-redeposition agent, and enzyme composition according to the present invention. The cleaning agent composition according to the present invention may contain known cleaning agent components, for example, a surfactant, a divalent metal ion scavenger, an alkali agent, an anti-redeposition agent, a bleaching agent, a fluorescent agent and the like, in addition to the mutant alkaline cellulase described above, or an anti-redeposition agent and/or enzyme composition containing the mutant alkaline cellulase.

As the surfactant, any surfactants such as anionic surfactants, nonionic surfactants, amphoteric surfactants and cationic surfactants, can be used singly or in combination of two or more kinds. A more preferred surfactant may be an anionic surfactant or a nonionic surfactant.

Preferred examples of the anionic surfactant include sulfuric acid ester salts of alcohols having 10 to 18 carbon atoms, sulfuric acid ester salts of alkoxylation products of alcohols having 8 to 20 carbon atoms, alkylbenzenesulfonates, alkyl sulfuric acid ester salts, paraffin sulfonates, α-olefin sulfonates, α-sulfo fatty acid salts, α-sulfo fatty acid alkyl ester salts, and fatty acid salts. For example, linear alkylbenzenesulfonates and alkyl sulfates having alkyl chains having 10 to 14 carbon atoms, and more preferably 12 to 14 carbon atoms, can be suitably used as the anionic surfactant in the present invention. As the counter ions of these salts, alkali metal salts or amines are preferred, and particularly, sodium, potassium, monoethanolamine and diethanolamine are preferred.

Preferred examples of the nonionic surfactant include polyoxyalkylene alkyl ($C_8$-$C_{20}$) ethers, alkyl polyglycosides, polyoxyalkylene alkyl ($C_8$-$C_{20}$) phenyl ethers, polyoxyalkylene sorbitan fatty acid ($C_8$-$C_{22}$) esters, polyoxyalkylene glycol fatty acid ($C_8$-$C_{22}$) esters, and polyoxyethylene polyoxypropylene block polymers. For example, polyoxyethylene (average number of added moles of EO: 6) alkyl ($C_{12}$-$C_{14}$) ethers can be suitably used as the nonionic surfactant in the present invention.

The total amount of the surfactant in the cleaning agent composition according to the present invention can be appropriately selected by a person having ordinary skill in the art. However, from the viewpoints of detergency and solubility, the total amount of the surfactant is preferably 10 to 60% by mass, more preferably 15 to 50% by mass, and even more preferably 20 to 45% by mass, relative to the mass of the cleaning agent composition. Among others, the content of the anionic surfactant is preferably 1 to 60% by mass, more preferably 1 to 50% by mass, and even more preferably 3 to 40% by mass, relative to the mass of the cleaning agent composition. Furthermore, the content of the nonionic surfactant is preferably 1 to 45% by mass, more preferably 1 to 35% by mass, and even more preferably 4 to 25% by mass, relative to the mass of the cleaning agent composition. The anionic surfactants and the nonionic surfactants can be used singly, and preferably the surfactants are used as mixtures. Further, amphoteric surfactants and cationic surfactants can also be used in combination in accordance with the purpose.

The cleaning agent composition according to the present invention may further include a builder. The builder is a compound which itself has no or only slight detergency, however, when incorporated together with a surfactant, can markedly enhance the detergent ability of the surfactant. Examples of the action of the builder include polyvalent metal cation scavenging action, dirt dispersing action, alkali buffering action, and combinations of two or more kinds thereof. Examples of such a builder include water-soluble inorganic compounds, water-insoluble inorganic compounds, and organic compounds.

Examples of builders as water-soluble inorganic compounds include phosphates (tripolyphosphates, pyrophosphates, metaphosphates, trisodium phosphate, and the like), silicates, carbonates, sulfates, and sulfites. Among them, phosphates are preferred in view of having all of the three types of actions. Examples of builders as water-insoluble inorganic compounds include aluminosilicates (A-type zeolite, P-type zeolite, X-type zeolite, amorphous aluminosilicates, and the like), and crystalline silicates. Examples of builders as organic compounds include carboxylates (aminocarboxylates, hydroxyaminocarboxylates, hydroxycarboxylates, cyclocarboxylates, maleic acid derivatives, oxalates, and the like), organic carboxylic acid (salt) polymers (acrylic acid polymers and copolymers, polyvalent carboxylic acid (for example, maleic acid and the like) polymers and copolymers, glyoxylic acid polymers, polysaccharides and salts thereof). Among them, organic carboxylic acid (salt) polymers are preferred. With regard to the salt of the builder, alkali metal salts and amines are preferred as the counter ions, and sodium, potassium, monoethanolamine and diethanolamine are more preferred. The builder contained in the cleaning agent composition according to the present invention preferably includes the water-soluble inorganic compounds described above, and is more preferably a combination of the water-soluble inorganic compounds and organic compounds described above. The builder is even more preferably a combination of the water-soluble inorganic compounds, organic compounds and water-insoluble inorganic compounds.

The total amount of the builder in the cleaning agent composition according to the present invention can be appropriately selected by a person ordinary skilled in the art, and the total amount is preferably 20 to 80% by mass, more preferably 30 to 70% by mass, and even more preferably 35 to 60% by mass, relative to the mass of the cleaning agent composition. Among them, the content of the water-soluble inorganic compound builder is preferably 10 to 50% by mass, more preferably 15 to 45% by mass, and even more preferably 20 to 40% by mass, relative to the mass of the cleaning agent composition. Among them, the content of the water-insoluble inorganic compound builder is preferably 5 to 50% by mass, more preferably 10 to 45% by mass, and even more preferably 15 to 40% by mass, relative to the mass of the cleaning agent composition. Among them, the content of the organic compound builder is preferably 0.1 to 20% by mass, more preferably 0.3 to 15% by mass, and even more preferably 0.5 to 10% by mass, relative to the mass of the cleaning agent composition.

Specific preferred compositions of the cleaning agent composition according to the present invention include the following compositions A to E.

Composition A: 20% by weight of sodium linear alkyl ($C_{12}$-$C_{14}$) benzenesulfonate, 4% by weight of a nonionic surfactant (polyoxyethylene alkyl ether having 12 to 16 carbon atoms and an average number of added moles of ethylene oxide of 6.0), 30% by weight of sodium carbonate, 10% by weight of sodium sulfate, 30% by weight of zeolite (4A-type zeolite (manufactured by Tosoh Corp.)), 2% by weight of an acrylate-maleate copolymer, and 4% by weight of crystalline silicate (powder SKS-6 (manufactured by Hoechst Tokuyama, Ltd.)).

Composition B: 24% by weight of sodium linear alkyl ($C_{12}$-$C_{14}$) benzenesulfonate, 5% of linear alkyl ($C_{10}$-$C_{13}$) sulfuric acid ester sodium, 6% of a fatty acid ($C_{14}$-$C_{18}$) sodium salt, 7% by weight of a nonionic surfactant (polyoxyethylene alkyl ether having 12 to 16 carbon atoms and an average number of added moles of ethylene oxide of 6.0), 12% of sodium tripolyphosphate, 12% by weight of sodium carbonate, 6% by weight of sodium sulfate, 14% by weight of zeolite (4A-type zeolite (manufactured by Tosoh Corp.)), 6% by weight of sodium polyacrylate (average molecular weight 10,000), and 8% by weight of crystalline silicate (powder SKS-6 (manufactured by Hoechst Tokuyama, Ltd.)).

Composition C: 12% by weight of sodium linear alkyl ($C_{12}$-$C_{14}$) benzenesulfonate, 11% by weight of a nonionic surfactant (polyoxyethylene alkyl ether having 12 to 16 carbon atoms and an average number of added moles of ethylene oxide of 6.0), 28% by weight of sodium carbonate, 11% by weight of sodium sulfate, 28% by weight of zeolite (4A-type zeolite (manufactured by Tosoh Corp.)), 8% by weight of sodium polyacrylate (average molecular weight 10,000), and 2% by weight of crystalline silicate (powder SKS-6 (manufactured by Hoechst Tokuyama, Ltd.)).

Composition D: 14% by weight of sodium linear alkyl ($C_{12}$-$C_{14}$) benzenesulfonate, 2% of a fatty acid ($C_{14}$-$C_{18}$) sodium salt, 10% by weight of a nonionic surfactant (polyoxyethylene alkyl ether having 12 to 16 carbon atoms and an average number of added moles of ethylene oxide of 6.0), 23% of sodium tripolyphosphate, 29% by weight of sodium carbonate, 6% by weight of sodium sulfate, 11% by weight of zeolite (4A-type zeolite (manufactured by Tosoh Corp.)), 3% by weight of sodium polyacrylate (average molecular weight 10,000), and 2% by weight of crystalline silicate (powder SKS-6 (manufactured by Hoechst Tokuyama, Ltd.)).

Composition E: 20% by weight of a nonionic surfactant (polyoxyethylene alkyl ether having 12 to 16 carbon atoms and an average number of added moles of ethylene oxide of 12.0), 1% by weight of alkylbenzyldimethylammonium chloride (alkyl group having 8 to 18 carbon atoms), 20% by weight of Softanol 7014 (manufactured by Nippon Shokubai Co., Ltd.), 1.5% by weight of an acrylate-maleate copolymer, 1.5% by weight of monoethanolamine, 1.15% by weight of citric acid, 5% by weight of butyl diglycol, 2% by weight of ethanol, 0.2% by weight of sodium sulfite, and 47.65% by weight of water.

The cleaning agent composition according to the present invention may further include other components such as water, a pH adjusting agent, a buffering agent, a dispersant, an antiseptic, an oxidation inhibitor, an excipient, a dye such as a fluorescent dye, a deodorizer, a deodorant, a fragrance, a softening agent, and a plant extract. The cleaning agent composition according to the present invention may be in any form such as a powder, granules, a compression molded tablet, or a liquid. The cleaning agent composition according to the present invention is such that an amount for one-time use may be packaged in sachets, from the viewpoints of portability or convenience, and in that case, the packaging material is preferably water-soluble.

Although there are no limitations, the cleaning agent composition according to the present invention is preferably intended to be used for garments or for clothing products (sheets, curtains, carpets, wall clothes, and the like). Since the cleaning agent composition according to the present invention contains a mutant alkaline cellulase showing high anti-redeposition ability, the cleaning agent composition can exhibit a satisfactory anti-redeposition effect.

The amount of incorporation of the mutant alkaline cellulase of the present invention into a cleaning agent composition is not particularly limited as long as it is an amount by which the alkaline cellulase exhibits activity. However, the amount of incorporation is preferably 0.1 to 5000 U, more preferably 1 to 3000 U, and even more preferably 10 to 2000 U, per kilogram of the cleaning agent composition.

EXAMPLES

Hereinafter, the present invention is more specifically described by way of Examples. However, the scope of the present invention is not intended to be limited to these Examples.

Meanwhile, the experimental procedure, reagents and the like that were commonly employed are described first in the following descriptions.

1) Amplification of DNA Fragment

The amplification of a DNA fragment was carried out by a polymerase chain reaction (PCR) using a GeneAmp PCR system (Applied Biosystems, Inc.) and using a Pyrobest DNA polymerase (Takara Bio, Inc.) and accessory reagents. The reaction liquid composition for PCR was obtained by mixing 1 µL of an appropriately diluted template DNA, 20 pmol each of a sense primer and an antisense primer, and 2.5 U of a Pyrobest DNA polymerase, and adding water to the mixture to adjust the total amount of the reaction liquid to 50 µL. The PCR reaction was carried out under the conditions of repeating 30 cycles of a three-stage temperature change cycle of 10 seconds at 98° C., 30 seconds at 55° C., and 1 to 5 minutes at 72° C. (the time was adjusted in accordance with the target amplification product, but was adjusted on the basis of 1 minute per kb), and then performing the reaction for 5 minutes at 72° C.

The primers used in the DNA fragment amplifications that will be described below are presented in Table 1-1 to Table 1-3.

TABLE 1-1

| Primer name | Primer sequence (5'→3') | SEQ ID NO: |
|---|---|---|
| 237UB1 | TTGCGGATCCAACAGGCTTATATTTAGAGGAAATTTC | 13 |
| S237RV | TCGCTACCCTTTTATTATCG | 14 |
| Q71E-RV | ATTTTTTCTCCATGTTCATCTACTAATGTC | 15 |
| Q71E-FW | GACATTAGTAGATGAACATGGAGAAAAAAT | 16 |
| S193R-RV | TCCACCATTATTATTACGACTCGGCTCA | 17 |
| S193R-FW | TGAGCCGAGTCGTAATAATAATGGTGGA | 18 |
| Q242S-RV | AGTCCGGACGCGAACTCCAGTTTG | 19 |
| Q242S-FW | CAAACTGGAGTTCGCGTCCGGACT | 20 |

TABLE 1-2

| Primer name | Primer sequence (5'→3') | SEQ ID NO: |
|---|---|---|
| N419A-RV | TTTGGAGAATCCGAAGCCACTCCAAATCCT | 21 |
| N419A-FW | AGGATTTGGAGTGGCTTCGGATTCTCCAAA | 22 |
| D421A-RV | CTTTATTTGGAGAAGCCGAATTCACTCCA | 23 |
| D421A-FW | TGGAGTGAATTCGGCTTCTCCAAATAAAG | 24 |
| W454Y-RV | AGACGAGCATTAGCATAGAAGTTGCCATCT | 25 |
| W454Y-FW | AGATGGCAACTTCTATGCTAATGCTCGTCT | 26 |
| W501Y-RV | CTCTGGATTTGCATATCCACTTTTAC | 27 |
| W501Y-FW | GTAAAAGTGGATATGCAAATCCAGAG | 28 |

TABLE 1-3

| Primer name | Primer sequence (5'→3') | SEQ ID NO: |
|---|---|---|
| Q58R-RV | ATCGACTTCTTGTAATTCTAATGCGCCA | 29 |
| Q58R-FW | TGGCGCATTAGAATTACAAGAAGTCGAT | 30 |
| Q58E-RV | ATCGACTTCTTGTAAACGTAATGCGCCA | 31 |
| Q58E-FW | TGGCGCATTACGTTTACAAGAAGTCGAT | 32 |

Furthermore, the primer sets for upstream region amplification and for downstream region amplification, which were used to introduce intended amino acid mutations to S237 cellulase or a mutant S237 cellulase in Examples 3 to 5, are presented in Table 2-1 to Table 2-3 (see the Examples described below for the details).

TABLE 2-1

| Amino acid mutation to be introduced | Glutamine at position 71 → glutamic acid | Serine at position 193 → arginine |
|---|---|---|
| Primer set for upstream region amplification | 237UB1 Q71E-RV | 237UB1 S193R-RV |
| Primer set for downstream region amplification | Q71E-FW S237RV | S193R-FW S237RV |

TABLE 2-2

| Amino acid mutation to be introduced | Asparagine at position 419 → alanine | Aspartic acid at position 421 → alanine | Tryptophan at position 454 → tyrosine | Tryptophan at position 501 → tyrosine |
|---|---|---|---|---|
| Primer set for upstream region amplification | 237UB1 N419A-RV | 237UB1 D421A-RV | 237UB1 W454Y-RV | 237UB1 W501Y-RV |
| Primer set for downstream region amplification | N419A-FW S237RV | D421A-FW S237RV | W454Y-FW S237RV | W501Y-FW S237RV |

TABLE 2-3

| Amino acid mutation to be introduced | Glutamine at position 58 → arginine | Glutamine at position 58 → glutamic acid | Glutamine at position 242 → serine |
|---|---|---|---|
| Primer set for upstream region amplification | 237UB1 Q58R-RV | 237UB1 Q58E-RV | 237UB1 Q242S-RV |
| Primer set for downstream region amplification | Q58R-FW S237RV | Q58E-FW S237RV | Q242S-FW S237RV |

2) Gene Introduction into *Bacillus subtilis*

The introduction of a gene encoding S237 cellulase or a mutant S237 cellulase into *Bacillus subtilis* was carried out according to any one of a competent cell transformation method (J. Bacteriol. 93, 1925 (1967)), an electroporation method (FEMS Microbiol. Lett. 55, 135 (1990)), and a protoplast transformation method (Mol. Gen. Genet. 168, 111 (1979)).

In the competent cell transformation method, first, *Bacillus subtilis* (*Bacillus subtilis* Marburg No. 168 (Nature, 390, (1997), p. 249)) was cultured by shaking in SPI medium (0.20% ammonium sulfate, 1.40% dipotassium hydrogen phosphate, 0.60% potassium dihydrogen phosphate, 0.10% trisodium citrate dihydrate, 0.50% glucose, 0.02% casamino acid (Difco Laboratories, Inc.), 5 mM magnesium sulfate, 0.25 manganese chloride, and 50 µg/ml tryptophan) at 37° C., until the degree of growth (OD600) reached about 1. After the shaking, a portion of the culture fluid was inoculated into a 9-fold amount of SPII medium (0.20% ammonium sulfate, 1.40% dipotassium hydrogen phosphate, 0.60% potassium dihydrogen phosphate, 0.10% trisodium citrate dihydrate, 0.50% glucose, 0.01% casamino acid (Difco Laboratories, Inc.), 5 mM magnesium sulfate, 0.40 µM manganese chloride, and 5 µg/ml tryptophan), and the cells were further cultured by shaking until the degree of growth (OD600) reached about 0.4. Thus, *Bacillus subtilis* cells were prepared as competent cells. Subsequently, in 100 μL of the competent cell suspension thus prepared (competent cell culture in SPII medium), 2 μL of a solution containing a plasmid vector having a gene encoding S237 cellulase or a gene encoding a mutant S237 cellulase was added, and the mixture was shaked for additional one hour at 37° C. Subsequently, the entire amount was spreaded on LB agar medium (1% tryptone, 0.5% yeast extract, 1% NaCl, and 1.5% agar) containing suitable antibiotics for selection. The cells were statically cultured at 37° C., and then grown colonies were isolated as a transformant.

In the protoplast transformation method, first, a *Bacillus subtilis* strain (*Bacillus subtilis* Marburg No. 168 (Nature, 390, (1997), p. 249)) was cultured by shaking in 50 mL of LB medium (1% tryptone, 0.5% yeast extract, and 1% NaCl) at 37° C. for about 2 hours, and at the time point at which the absorbance at 600 nm reached 0.4, the bacterial cells were collected by centrifugation (7000 rpm, for 15 minutes) at room temperature. The collected bacterial cells were suspended in 5 mL of SMMP [0.5 M sucrose, 20 mM disodium maleate, 20 mM magnesium chloride hexahydrate, and 35% (w/v) Antibiotic Medium 3 (Difco Laboratories, Inc.)], and then 500 μL of a lysozyme solution (30 mg/mL) dissolved in SMMP solution was added to the suspension. The mixture was incubated at 37° C. for one hour to convert the bacterial cells to protoplasts. After completion of the incubation, the protoplasts were collected by centrifugation (2800 rpm, for 15 minutes) at room temperature and were suspended in 5 mL of SMMP to prepare a protoplast solution. To 0.5 mL of the protoplast solution, 10 μL of a plasmid solution (containing a plasmid vector which included a gene encoding S237 cellulase or a gene encoding a S237 cellulase variant) and 1.5 mL of 40% (w/v) polyethylene glycol (PEG8000, Sigma-Aldrich Co.) were added, and the mixture was gently stirred and left to stand for 2 minutes at room temperature. Immediately, 5 mL of a SMMP solution was mixed into the mixture, and the protoplasts were collected by centrifugation (2800 rpm, for 15 minutes) at room temperature and were resuspended in 1 mL of a SMMP solution. The protoplast suspension was shaken (120 rpm) for 90 minutes at 37° C., and then the suspension was applied on DM3 regeneration agar medium [0.8% (w/v) agar (Wako Pure Chemical Industries, Ltd.), 0.5% disodium succinate hexahydrate, 0.5% casamino acid technical (Difco Laboratories, Inc.), 0.5% yeast extract, 0.35% monopotassium phosphate, 0.15% dipotassium phosphate, 0.5% glucose, 0.4% magnesium chloride hexahydrate, 0.01% bovine serum albumin (Sigma-Aldrich Co.), 0.5% carboxymethyl cellulose, 0.005% trypan blue (Merck GmbH), and an amino acid mixture liquid (10 μg/mL each of tryptophan, leucine and methionine)] containing tetracycline (15 μg/mL, Sigma). The protoplasts were cultured for 72 hours at 30° C., and grown colonies were isolated as a transformant.

In the culture of the transformants for production of recombinant protein in the Examples described below, LB medium (1% tryptone, 0.5% yeast extract, and 1% NaCl) was used as a medium for seed culture, and 2×YT medium (1.6% tryptone, 1% yeast extract, and 0.5% NaCl) or 2×L-maltose medium (2% tryptone, 1% yeast extract, 1% NaCl, 7.5% maltose, and 7.5 ppm manganese sulfate tetra- or pentahydrate) was used as a medium for main culture.

3) Preparation of Cleaning Agent Composition

In the evaluation of the anti-redeposition ability, a cleaning agent of the preferred composition C or E described above, or IEC-A detergent (composition F) supplied from Wfk Testgewebe GmbH (D-41379, Germany) was used as the cleaning agent composition. In the evaluation of an enzyme stability test, a cleaning agent of the composition E was used.

4) Evaluation of Anti-Redeposition Ability

The evaluation of the anti-redeposition ability was carried out according to the detergency evaluation method described in JIS K3362: 1998, as follows. 0.33 g of a cleaning agent composition was dissolved in 50 mL of water (in the case of 4° DH, $CaCl_2$: 55.42 mg/L, $MgCl_2.6H_2O$: 43.51 mg/L; in the case of 12° DH, $CaCl_2$: 166.26 mg/L, $MgCl_2.6H_2O$: 130.53 mg/L), and 0.125 g of carbon black (Asahi Carbon Black for cleaning, manufactured by Asahi Carbon Co., Ltd., or Carbon Black #4000B, MA100 or #40, manufactured by Mitsubishi Chemical Corp.) as a model for hydrophobic soot stain was added to the solution. 50 mL of water ($CaCl_2$: 55.42 mg/L, $MgCl_2.6H_2O$: 43.51 mg/L) was added to the mixture, and then the mixture was exposed with ultrasonic waves at 26±1.5 kHz for 5 minutes to uniformly disperse the components. 400 mL of water ($CaCl_2$: 55.42 mg/L, $MgCl_2.6H_2O$: 43.51 mg/L) at 20° C. was further added to the dispersion liquid, and a predetermined amount of alkaline cellulase (S237 cellulase or mutant S237 cellulase) was added to the mixture. This was used as washing water. The washing water thus prepared was transferred into the sample cup of an agitation-type detergency tester, Terg-O-To meter; Ueshima Seisakusho Co., Ltd.) at 20° C. As a cloth for evaluation, 5 sheets of a white cotton cloth (#2003 white woven fabric, 100% cotton, supplied by Tanigashira Shoten (4-11-15, Komatsu, Higashiyodogawa-ku, Osaka-shi, Osaka-fu, Japan)) having a size of 6 cm×6 cm were placed in the sample cup. In order to further adjust the amount of cloth (bath ratio) relative to the solution, an appropriate amount of a white knitted cotton cloth [seared bleached cloth (supplied by Tanigashira Shoten) that had been washed and then sufficiently rinsed] was introduced to the sample cup, and the contents were stirred for 10 minutes at a rotation speed of 80±4 rpm. Subsequently, the white cotton cloth was removed together with the white knitted cotton cloth, and the clothes were lightly wrung out and then rapidly introduced into 2000 mL of tap water. Only the white cotton cloth was taken out therefrom, and then the cloth was rinsed for 3 minutes under flowing tap water and was subjected to dehydration and finish ironing. The reflection ratio at 550 nm of the white cotton cloth was measured using a spectrophotometer, CM-3500d (Konica Minolta Holdings, Inc.) (the samples are referred to as enzyme-added group). For the white cotton cloth, the reflection ratio at 550 nm was measured in advance before the washing test, using a spectrophotometer, CM-3500d (Konica Minolta Holdings, Inc.). A control experiment was carried out by the same procedure, except that no alkaline cellulase was added to the dispersion liquid (non-enzyme-added group).

The anti-redeposition ratio for each of the washing test was calculated by the following formula, based on the reflection ratio thus obtained.

Anti-redeposition ratio (%)={(Reflection ratio of white cotton cloth after test)/(reflection ratio of white cotton cloth before test)}×100   [Mathematical formula 5]

Subsequently, the effect of enzyme addition on the preventing of redeposition, that is, the degree of promotion of anti-redeposition as a result of the addition of an alkaline cellulase enzyme, was calculated by the following formula, based on the anti-redeposition ratio thus calculated. In the Examples described below, the anti-redeposition ability of the added alkaline cellulase was evaluated by using this degree of promotion of anti-redeposition (%) as an index.

Degree of promotion of anti-redeposition by enzyme addition (%)={(Anti-redeposition ratio of enzyme-added group)−(anti-redeposition ratio of non-enzyme-added group)}/{100−(anti-redeposition ratio of non-enzyme-added group)}×100     [Mathematical formula 6]

Furthermore, the effect of mutagenesis in the alkaline cellulase on the anti-redeposition ability of the enzyme, that is, the degree of anti-redeposition ability enhancement in the mutant alkaline cellulase, was calculated by the following formula. Meanwhile, the mutant enzyme was a mutant alkaline cellulase into which an intended amino acid substitution had been introduced, and the control enzyme was a parent alkaline cellulase, that is, a wild-type alkaline cellulase or an alkaline cellulase before substitution of the amino acid residue.

Degree of anti-redeposition ability enhancement (%) for mutant alkaline cellulase={(Anti-redeposition ratio of mutant enzyme-added group)−(anti-redeposition ratio of control enzyme-added group)}/ {100−(anti-redeposition ratio of control enzyme-added group)}×100     [Mathematical formula 7]

5) Evaluation of Anti-Redeposition Ability of *Bacillus* sp. Strain KSM-S237-Derived Alkaline Cellulase (S237 Cellulase)

(1. Recombinant Production of S237 Cellulase)

A nucleic acid fragment (3.1 kb) including an alkaline cellulase gene that encodes S237 cellulase (SEQ ID NO: 2) derived from *Bacillus* sp. strain KSM-S237 (FERM BP-7875) [hereinafter, also referred to as S237 cellulase gene; the base sequence is available based on GenBank Accession No. AB18420 (SEQ ID NO: 1); Hakamada et al., Biosci. Biotechnol. Biochem., 64(11), (2000) p. 2281-2289; JP-A No. 2000-210081] was amplified according to the procedure of the section "1) Amplification of DNA fragment" as described above, using a primer set consisting of primers 237UB1 and S237RV indicated in the above Table 1-1. As a template DNA, the genomic DNA extracted from the strain KSM-S237 by a routine method was used.

The amplified fragment was inserted into the SmaI restriction enzyme cleavage site of a shuttle vector, pHY300PLK (Yakult Honsha Co., Ltd.; Ishiwa, H. & Shibahara, H., Jpn. J. Genet. (1985) 60, p. 235-243), and thus a recombinant plasmid, pHY-S237, was constructed. The sequence of the S237 cellulase gene fragment inserted into the plasmid was determined by using a 3100 DNA Sequencer (Applied Biosystems, Inc.), and thereby, confirmed that the fragment had the base sequence set forth in SEQ ID NO: 1. Subsequently, *Bacillus subtilis* (*Bacillus subtilis* Marburg No. 168 (Nature, 390, (1997) p. 249)) was transformed using the recombinant plasmid, pHY-S237, according to the section "2) Gene introduction into *Bacillus subtilis*" by protoplast transformation method. The transformant thus obtained was cultured overnight by shaking at 30° C. in 10 mL of LB medium (1% tryptone, 0.5% yeast extract, and 1% NaCl), and 0.05 mL of this culture fluid was inoculated into 50 mL of 2×L-maltose medium (2% tryptone, 1% yeast extract, 1% NaCl, 7.5% maltose, 7.5 ppm manganese sulfate tetra- or pentahydrate, and 15 ppm tetracycline) and was cultured by shaking for 3 days at 30° C. A supernatant of the culture fluid, from which bacterial cells had been removed by centrifugation, was diluted 10 times with deionized water, and then the diluted solution was loaded in a DEAE-Toyopearl 650C (Tosoh Corp.) column (1 cm×3 cm) which had been equilibrated with a 20 mM sodium phosphate buffer solution (pH 6.0). The column was washed with 10 mL of a 20 mM sodium phosphate buffer solution (pH 6.0) containing 0.075 M NaCl, and then proteins were eluted from the column using 10 mL of a 20 mM sodium phosphate buffer solution (pH 6.0) containing 0.4 M NaCl. The target recombinant S237 cellulase was eluted as an electrophoretically almost single component. The eluted sample was dialyzed against a 10 mM Tris hydrochloride buffer solution (pH 7.5) containing 1 mM $CaCl_2$, and was subjected to desalting treatment. Subsequently, the content of the alkaline cellulase was measured by the following method. That is, 50 μL of 0.4 mM p-nitrophenyl-β-D-cellotrioside (Seikagaku Corp.) was added and mixed into 50 μL of the sample solution which had been appropriately diluted with a 1/7.5 M phosphate buffer solution (pH 7.4, Wako Pure Chemical Industries, Ltd.), and the amount of p-nitrophenol released when the reaction had been carried out at 30° C. was quantified based on the change of absorbance at 420 nm (OD420). The amount of the enzyme that releases 1 μmol of p-nitrophenol for one minute was defined as 1 U. Further, the amount of proteins was measured by using a Protein Assay Rapid Kit (manufactured by Wako Pure Chemical Industries, Ltd.) and the bovine serum albumin included in the kit as a standard, using.

A sample containing the recombinant S237 cellulase thus obtained (wild-type S237 cellulase) was subjected to evaluation of the anti-redeposition ability as described below. The evaluation was carried out by adding an enzyme protein in an amount equivalent to 26.4 mU, 52.8 mU, 106 mU, 211 mU or 264 mU, to 500 mL of the washing system.

(2. Anti-Redeposition Ability Evaluation Using Various Carbon Blacks)

The anti-redeposition ability of S237 cellulase was evaluated by using various carbon blacks. As the carbon blacks, 4 kinds of carbon blacks such as Asahi carbon black for cleaning manufactured by Asahi Carbon Co., Ltd., and Carbon Black #4000B, MA100 and #40 manufactured by Mitsubishi Chemical Corp. were used.

Prior to the anti-redeposition ability evaluation, the characteristics of each of the carbon blacks (hydrophobicity, and the acidic functional group content) were investigated as follows. 100 mL of an aqueous solution of 0.1% (w/v) polyoxyethylene (average number of added moles of EO 6) alkyl ($C_{12}$-$C_{14}$) ether was charged into a 100-mL beaker (Iwaki Co., Ltd.), 0.1 g of each carbon black powder was dropped from 10 cm above the surface of the aqueous solution to the surface, and the time necessary for settling the entire amount of the powder was measured. Measurement was repeated three times, and as a result, the time for settling was 4.9±0.6 seconds for #4000B, 14.1±1.0 seconds for MA100, and 60.5±4.6 seconds for #40. For A portion of the Asahi carbon black for cleaning was staying on the surface of the aqueous solution even after a lapse of 10 minutes or longer, and the time necessary for the entire amount to be wetted was 78.8±9.1 seconds. According to the these results, it was found that among the various carbon blacks, hydrophobicity of #4000B was the lowest, followed by MA100 and #40 in this order, and hydrophobicity of the Asahi carbon black for cleaning was the highest. Subsequently, each of carbon black suspensions was exposed to ultrasonication at 26±1.5 kHz for 5 minutes, and while the suspension was thoroughly stirred, pH was measured. The pH of an aqueous solution of 0.1% (w/v) polyoxyethylene (average number of added moles of EO 6) alkyl ($C_{12}$-$C_{14}$) ether containing no carbon black was 4.75, and was 4.97 for #4000B, 4.69 for MA100, 4.81 for #40, and 4.86 for Asahi carbon black for cleaning after each of the carbon black was dispersed therein. pH of the dispersion liquid was decreased as a result of addition of MA100, the result suggests that MA100 contains the largest number of acidic functional groups (it may be considered that a majority of the functional groups are carboxyl groups), of the other hand, #4000B contains the smallest acidic functional group content among the carbon blacks investigated.

Considering the characteristics of various carbon blacks as described above, an evaluation of the anti-redeposition ability was carried out according to the section "4) Evaluation of anti-redeposition ability" described above. The results obtained by using a cleaning agent having the composition C and adding S237 cellulase in an enzyme amount equivalent to 0 mU, 106 mU or 264 mU, are shown in Table 3 (anti-redeposition ratio) and Table 4 (degree of promotion of anti-redeposition).

TABLE 3

| Enzyme added (mU/500 mL) | Anti-redeposition ratio (%) | | | | | | | |
|---|---|---|---|---|---|---|---|---|
| | Asahi cleaning | | #40 | | MA100 | | #4000B | |
| | Mean value | Standard deviation | Mean value | Standard deviation | Mean value | Standard deviation | Mean value | Standard deviation |
| 0 | 62.6 | 2.8 | 77.6 | 1.0 | 74.0 | 1.0 | 83.4 | 0.5 |
| 106 | 76.1 | 1.1 | 81.3 | 0.9 | 78.8 | 1.0 | 85.4 | 0.7 |
| 264 | 78.2 | 0.5 | 81.9 | 1.3 | 80.4 | 0.9 | 85.6 | 0.6 |

TABLE 4

| Enzyme added (mU/500 mL) | Degree of promotion of anti-redeposition due to enzyme addition (%) | | | |
|---|---|---|---|---|
| | Asahi cleaning | #40 | MA100 | #4000B |
| 106 | 36.2 | 16.8 | 18.6 | 11.7 |
| 264 | 41.6 | 19.1 | 24.8 | 13.3 |

As shown in Table 4, an effect of promoting prevention of the redeposition caused by any of the carbon blacks, as a result of the addition of S237 cellulase, was observed. The most significant anti-redeposition promoting effect was exhibited by Asahi carbon black for cleaning, and followed by MA100, #40 and #4000B in this order, with slight differences. These results of order suggest that the effect of promoting the preventing of redeposition due to the addition of S237 cellulase is greatly affected by degree of hydrophobicity of the carbon black.

Figure 2:
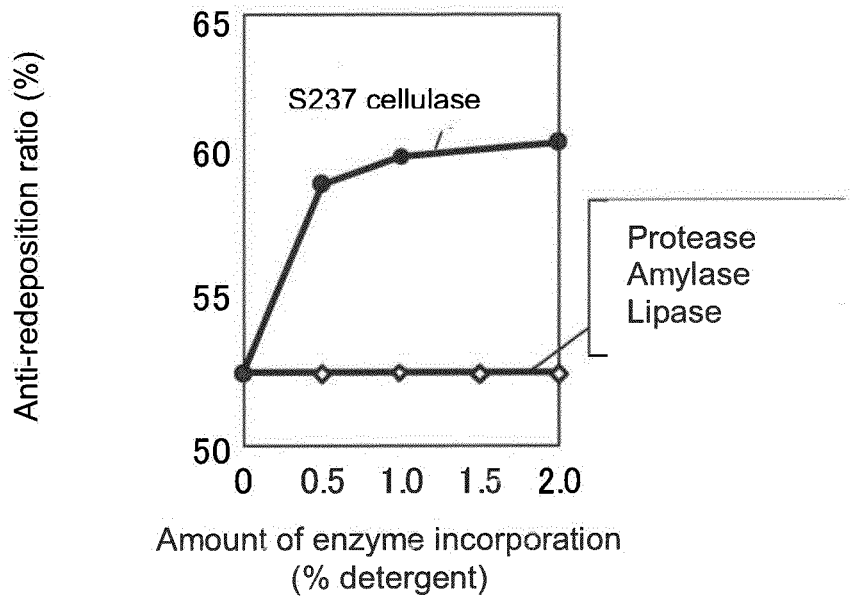
FIG. 2 is a diagram illustrating the effect for promoting preventing of redeposition provided by the addition of S237 cellulase in comparison with other enzymes.
Figure 2:
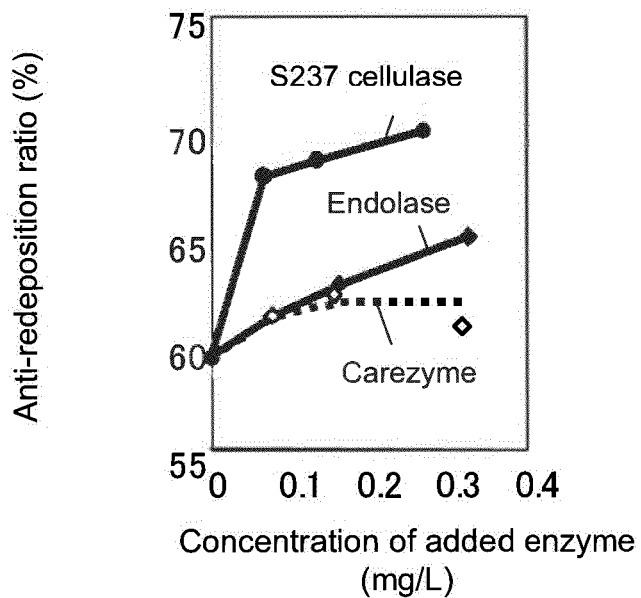

Furthermore, for a comparison, an evaluation of the anti-redeposition ability was carried out by the same method as described above, except that a protease, an amylase or a lipase as another type of hydrolase, and Endolase (Novozymes, Inc.) and Carezyme (Novozymes, Inc.) as another type of cellulase were used instead of S237 cellulase. Protein amounts of these enzymes were equivalent to concentrations of 26.4 mU, 52.8 mU and 211 mU. As the carbon black, Asahi carbon black for cleaning manufactured by Asahi Carbon Co., Ltd. was used. For a control experiment, an evaluation of the anti-redeposition ability was carried out under the same conditions using S237 cellulase. The results are shown in FIG. 2.

As a result, when a protease, an amylase or a lipase was used, the anti-redeposition ratios of the enzyme-added group and the non-enzyme-added group were all approximately 52%, without a significant difference, and the anti-redeposition promoting effect caused by the addition of these enzymes was not observed. On the other hand, when S237 cellulase was used, an increase in the anti-redeposition ratio was observed along with increase of amount of the enzyme addition, and therefore, the anti-redeposition promoting effect was confirmed.

When each of Endolase (Novozymes, Inc.) and Carezyme (Novozymes, Inc.) was used, the anti-redeposition ratio gradually increased along with increase of amount of the enzyme addition. However, when compared with S237 cellulase, the degree of the increase was small, and the anti-redeposition promoting effect was small. On the other hand, when S237 cellulase was used, anti-redeposition promoting effect, that was twice or more than that of Endolase, which exhibited a higher anti-redeposition promoting effect than Carezyme, was observed. These results suggest that S237 cellulase provides high anti-redeposition promoting effect which is not observed when other enzymes are used.

(3. Investigation of pH Dependency of Anti-Redeposition Promoting Effect)

The effect of pH of washing water on the anti-redeposition promoting effect caused by enzyme addition was investigated as follows. An evaluation was carried out according to the anti-redeposition ability evaluation method described above, by using a cleaning agent of the composition E, and S237 cellulase in an enzyme amount equivalent to 0 mU or 52.8 mU, with the proviso that the pH of the cleaning liquid was adjusted to 8.0, 4.3, 4.1 or 3.6 by adding sulfuric acid.

Figure 3:
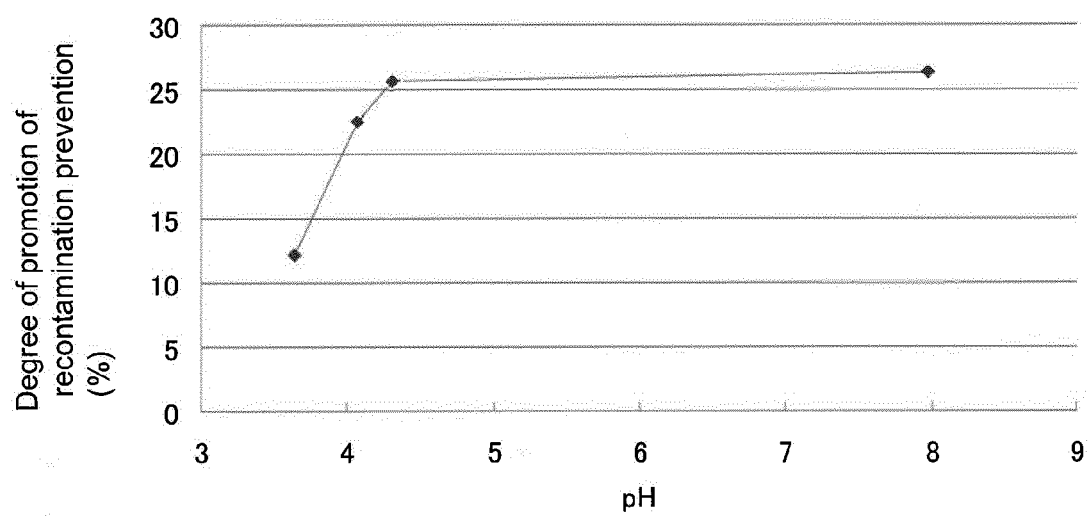
FIG. 3 is a diagram illustrating the pH dependency of the anti-redeposition effect provided by the addition of S237 cellulase.

As a result, as shown in FIG. 3, the anti-redeposition promoting effect was slightly decreased at pH 4.1, and was largely decreased at pH 3.6. Even in consideration of the fact disclosed in Patent Document 1 (which describes an invention related to S237 cellulase) that the pH stability of S237 cellulase greatly decreases near pH 4 (FIG. 3 in Patent Document 1), the above-described results suggest that the anti-redeposition ability possessed by S237 cellulase is largely impaired under the conditions where an irreversible structural change will occur, such as pH decrease. Furthermore, S237 cellulase would hardly exhibit any activity under the conditions of pH 5 or lower (FIG. 5 in Patent Document 1), however the anti-redeposition promoting effect at pH 4.3 was recognized to be almost equivalent to the effect at pH 8. These findings suggest that the anti-redeposition promoting effect of S237 cellulase originates from the structure of the enzyme.

According to the evaluation of anti-redeposition ability described above, the promoting effect of less hydrophobic MA100 was found to be equal to or higher than the effect of #40, suggesting that the anti-redeposition ability of S237 cellulase is affected by the content of the acidic functional groups of carbon black, that is, the abundance of negative charge factors. Therefore, it could be considered that the anti-redeposition ability of S237 cellulase is dependent on the physical repulsion between S237 cellulase and hydrophobic substances (repulsion between hydrophilic groups and hydrophobic groups+electrostatic repulsion).

Furthermore, it was speculated, based on the results obtained from the investigation of pH dependency as described above, that when the properties derived from the structure of S237 cellulase are modified, the anti-redeposition ability may be enhanced.

Specifically, it was conceived that when the hydrophilicity of the enzyme surface is further increased while the basic structure of S237 cellulase is maintained, high repulsion is caused between the enzyme surface and hydrophobic carbon black, and consequently, the anti-redeposition ability of S237 cellulase can be enhanced (see FIG. 1B).

6) Steric Structure Modeling of S237 Cellulase

In order to increase the hydrophilicity of the enzyme surface of S237 cellulase, a method may be employed wherein a position which has less influence on the overall structure of S237 cellulase, even if the position is substituted, is selected among the positions on the amino acid sequence where non-charged amino acid residues that are exposed to the enzyme surface in S237 cellulase are present, and the non-charged amino acid residue at the position is substituted with a charged amino acid residue. Thus, in order to select suitable positions for substitution, at first, a steric structure model of S237 cellulase was constructed as described below.

Steric structure modeling of the catalytic domain of S237 cellulase was carried out by the following procedure, using steric structures of the catalytic domain of *Bacillus* sp. strain KSM-635-derived alkaline cellulase (635 cellulase) (registered in Protein Data Bank (PDB); 1G01 and 1G0C) as models. IRIS Indigo2 Extreme was used as the computer, and insightII (Ver. 95.5) was used as a graphical user interface program. The structure of S237 cellulase was constructed based on the structure of 635 cellulase, using a module of insightII, modeler 4. That is, the topology of the S237 cellulase sequence was produced by referring to the coordinates of 635 cellulase, and for the atoms for which the coordinates could not be defined, allocation of the coordinates was carried out by referring to a residue topology file (RTF) of a polymer system modeling program, CHARMm (accessible from Chemistry at HARvard Macromolecular Mechanics, http://www.charmm.org/). Subsequently, the restraint on the structure of S237 cellulase was calculated as a probability density function (PDF), based on the alignment between the amino acid sequence of 635 cellulase and the amino acid sequence of S237 cellulase. The number of models thus produced was previously fixed at 1, for producing models that satisfy as many restraints as possible. Optimization of the models by a variable target function method (VTF) was carried out as follows. First, only those restraints that can be easily optimized (in which corresponding atoms are closely positioned each other) were selected, and energy minimization was carried out by a conjugate gradient method. Subsequently, these steps were repeated for other restraint conditions also, and finally, energy minimization according to a conjugate gradient method was performed for all restraints. Next, model optimization by simulated annealing was carried out. Energy minimization according to a conjugate gradient method, simulated annealing (heating conditions (Heating)→cooling conditions (Cooling)), and energy minimization according to a conjugate gradient method were carried out by using an optimization protocol "Low" (based on maximum speed molecular dynamic simulated annealing), under the conditions in which only those restraints that did not satisfy the conditions and the atoms corresponding thereto were selected, while other atoms were fixed. Subsequently, all the restraints and atoms were selected and energy minimization according to the conjugate gradient method was carried out. The degree of restraint violation was calculated, and after confirming that the level was not particulary irregular, the final model was constructed.

The model thus constructed was subjected to a visualization analysis using the program Discovery Studio Visualizer Ver. 1.5 (Accelrys Software, Inc.). The residue solvent accessibility of each amino acid residue was calculated by performing an analysis using the Solvent Accessibility program of Discovery Studio Visualizer Ver. 1.5, by setting the grid point for each atom at 240, and the probe radius at 1.40.

An amino acid residue having a value of this residue solvent accessibility of 50 or greater was considered as an amino acid residue having a high degree of surface exposure, and the relevant amino acid was appointed as a primary candidate of amino acid residues that can be selected as the objects of substitution in the present invention. From the primary candidates, first, charged amino acid residues were excluded. Next, the 3 amino acid residues in the N-terminal region and the 36 amino acid residues in the C-terminal region, which had low reliability of modeling, were also excluded. Furthermore, in consideration of that the constructed model was a model lacking the cellulose binding module (CBM domain), in the actual steric structure of S237 cellulase, the amino acid residues following the aspartic acid at position 369 (Asp369), which have a possibility of being covered by the CBM domain and not exposed to the surface, were excluded from the candidates for substitution. Furthermore, in the actual steric structure of S237 cellulase, leucine at position 42 (Leu42) to glycine at position 44 (Gly44), which have a possibility of being covered by the amino-terminal region that had been excluded from the constructed model, were excluded from the candidates for substitution. Further, the two tryptophan residues at position 88 and position 240 (Trp88 and Trp240) in the vicinity of the substrate binding pocket of S237 cellulase also have a possibility of participating in the binding with a substrate, and therefore, the tryptophan residues were excluded from the candidates. The asparagine residues at position 250 and position 330 (Asn250 and Asn330), around which both acidic amino acid residues and basic amino acid residues are present, were also excluded from the candidates for substitution. As a result, 55 non-charged amino acid residues were selected as the amino acid residues to be substituted of the present invention. The result suggests that when these non-charged amino acid residues thus selected are substituted with charged amino acid residues, the surface charge of S237 cellulase would be increased, and the anti-redeposition ability of S237 cellulase would be enhanced.

Furthermore, with regard to other cellulases sharing high identity with S237 cellulase, the result suggests that non-charged amino acid residues that are exposed to the enzyme surface may be present at the positions corresponding to these 55 amino acid residues with high possibility, and therefore the anti-redeposition ability of the cellulases would be enhanced by similarly substituting the amino acid residues at those positions with charged amino acid residues.

In the columns for "S237" in the following Table 5, 54 amino acid residues that can be considered as the target for substitution that have been selected as described above in connection with the catalytic domain of S237 cellulase are shown. Furthermore, Table 5 shows amino acid residues of other alkaline cellulases sharing high amino acid sequence identity with S237 cellulase, *Bacillus* sp. strain DSM12648-derived alkaline cellulase (DSM12648 cellulase; SEQ ID NO: 4), *Bacillus* sp. strain 1139-derived alkaline cellulase (1139 cellulase; SEQ ID NO: 6), *Bacillus* sp. strain KSM-64-derived alkaline cellulase (endo-1,4-β-glucanase) (64 cellulase; SEQ ID NO: 8), *Bacillus* sp. strain KSM-635-derived alkaline cellulase (KSM-635 cellulase; SEQ ID NO: 10), and *Bacillus* sp. strain N-4-derived alkaline cellulase (endoglucanase) (N4 cellulase; SEQ ID NO: 12), which are aligned to the 55 amino acid residues of S237 cellulase (that is, present at the positions corresponding to those residues) when an alignment of the amino acid sequence of each of the cellulases and the amino acid sequence of S237 cellulase is produced (Table 5). Each of the positions of the amino acid residues is indicated by the number of the amino acid residue in the amino acid sequence of the alkaline cellulase set forth in respective sequence ID number.

TABLE 5

| S237 | | DSM12648 | | | 1139 | | | 64 | | | KSM635 | | | N4 | |
|---|---|---|---|---|---|---|---|---|---|---|---|---|---|---|---|
| Amino acid position | Amino acid (3-letter code) | Amino acid position | Amino acid (3-letter code) | Amino acid (1-letter code) | Amino acid position | Amino acid (3-letter code) | Amino acid (1-letter code) | Amino acid position | Amino acid (3-letter code) | Amino acid (1-letter code) | Amino acid position | Amino acid (3-letter code) | Amino acid (1-letter code) | Amino acid position | Amino acid (3-letter code) | Amino acid (1-letter code) |
| 45 | Asn | 16 | Asn | N | 45 | Asn | N | 44 | Asn | N | 226 | Thr | T | 63 | Gly | G |
| 52 | Ser | 23 | Ser | S | 52 | Ser | S | 51 | Ser | S | 233 | Ser | S | 71 | Ser | S |
| 56 | Ala | 27 | Ala | A | 56 | Ala | A | 55 | Ala | A | 237 | Ala | A | 75 | Ala | A |
| 58 | Gln | 29 | Gln | Q | 58 | Gln | Q | 57 | Gln | Q | 239 | Gln | Q | 77 | Gln | Q |
| 60 | Gln | 31 | Gln | Q | 60 | Gln | Q | 59 | Gln | Q | 241 | Val | V | 79 | Val | V |
| 64 | Gly | 35 | Gly | G | 64 | Gly | G | 63 | Gly | G | 245 | Gly | G | 83 | Gly | G |
| 66 | Met | 37 | Met | M | 66 | Met | M | 65 | Met | M | 247 | Leu | L | 85 | Val | V |
| 71 | Gln | 42 | Gln | Q | 71 | Gln | Q | 70 | Gln | Q | 252 | Glu | E | 90 | Gln | Q |
| 103 | Asn | 74 | Asn | N | 103 | Asn | N | 102 | Asn | N | 284 | Asn | N | 122 | Asn | N |
| 119 | Asn | 90 | Asn | N | 119 | Asn | N | 118 | Asn | N | 300 | Asn | N | 138 | Asn | N |
| 122 | Ala | 93 | Ala | A | 122 | Ala | A | 121 | Ala | A | 303 | Ala | A | 141 | Arg | R |
| 123 | Thr | 94 | Ser | S | 123 | Ser | S | 122 | Ser | S | 304 | Thr | T | 142 | Tyr | Y |
| 124 | Asn | 95 | Asn | N | 124 | Asn | N | 123 | Asn | N | 305 | Asn | N | 143 | Asn | N |
| 125 | Pro | 96 | Pro | P | 125 | Pro | P | 124 | Pro | P | 306 | Pro | P | 144 | Pro | P |
| 127 | Leu | 98 | Leu | L | 127 | Leu | L | 126 | Leu | L | — | — | — | 146 | Leu | L |
| 130 | Gln | 101 | Ser | S | 130 | Ser | S | 129 | Ser | S | 310 | Asp | D | 148 | Glu | E |
| 140 | Ile | 111 | Ile | I | 140 | Ile | I | 139 | Ile | I | 320 | Phe | F | 158 | Lys | K |
| 161 | Pro | 132 | Pro | P | 161 | Pro | P | 160 | Pro | P | 341 | Asp | D | 179 | Asp | D |
| 164 | Ala | 135 | Ala | A | 164 | Ala | A | 163 | Ala | A | 344 | Ser | S | 193 | Leu | L |
| 175 | Ala | 146 | Ala | A | 175 | Ala | A | 174 | Ala | A | 355 | Asp | D | 204 | Glu | E |
| 176 | Leu | 147 | Leu | L | 176 | Leu | L | 175 | Leu | L | 356 | His | H | 205 | Lys | K |
| 178 | Pro | 149 | Pro | P | 178 | Pro | P | 177 | Pro | P | 361 | Pro | P | 207 | Pro | P |
| 179 | Asn | 150 | Asn | N | 179 | Asn | N | 178 | Asn | N | 362 | Lys | K | 208 | Asn | N |
| 181 | Pro | 152 | Pro | P | 181 | Pro | P | 180 | Pro | P | 364 | His | H | 210 | Pro | P |
| 193 | Ser | 164 | Ser | S | 193 | Ser | S | 192 | Ser | S | 376 | Pro | P | 222 | Pro | P |
| 194 | Asn | 165 | Asn | N | 194 | Asn | N | 193 | Asn | N | 377 | Asn | N | 223 | Asn | N |
| 195 | Asn | 166 | Asn | N | 195 | Asn | N | 194 | Asn | N | 378 | Asn | N | 224 | Ser | S |
| 196 | Asn | 167 | Asn | N | 196 | Asn | N | 195 | Asn | N | 379 | Asn | N | 225 | Ser | S |
| 197 | Gly | 168 | Gly | G | 197 | Gly | G | 196 | Gly | G | 380 | Gly | G | 226 | Gly | G |
| 199 | Ala | 170 | Ala | A | 199 | Ala | A | 198 | Ala | A | 382 | Pro | P | 228 | Pro | P |
| 202 | Pro | 173 | Pro | P | 202 | Pro | P | 201 | Pro | P | 385 | Thr | T | 231 | Thr | T |
| 203 | Asn | 174 | Asn | N | 203 | Asn | N | 202 | Asn | N | 386 | Asn | N | 232 | Asn | N |
| 217 | Pro | 188 | Pro | P | 217 | Pro | P | 216 | Pro | P | 400 | Pro | P | 246 | Pro | P |
| 225 | Ser | 196 | Ser | S | 225 | Ser | S | 224 | Ser | S | 408 | Lys | K | 254 | Ser | S |
| 227 | Asn | 198 | Asn | N | 227 | Asn | N | 226 | Asn | N | — | — | — | 256 | Asn | N |
| 228 | Ala | 199 | Ala | A | 228 | Ala | A | 227 | Ala | A | — | — | — | 257 | Ala | A |
| 251 | Pro | 222 | Pro | P | 251 | Pro | P | 250 | Pro | P | 431 | Pro | P | 281 | Pro | P |
| 267 | Ser | 238 | Ser | S | 267 | Ser | S | 266 | Ser | S | 447 | Ser | S | 297 | Thr | T |
| 272 | Thr | 243 | Thr | T | 272 | Thr | T | 271 | Thr | T | 452 | His | H | 302 | Asn | N |
| 276 | Pro | 247 | Pro | P | 276 | Pro | P | 275 | Pro | P | 456 | Pro | P | 306 | Pro | P |
| 277 | Pro | 248 | Pro | P | 277 | Pro | P | 276 | Pro | P | 457 | Glu | E | 307 | Glu | E |
| 280 | Pro | 251 | Pro | P | 280 | Pro | P | 279 | Pro | P | 460 | Pro | P | 310 | Ser | S |
| 282 | Ser | 253 | Ser | S | 282 | Ser | S | 281 | Ser | S | 462 | Ser | S | 312 | Glu | E |
| 297 | Asn | 268 | Asn | N | 297 | Asn | N | 296 | Asn | N | 477 | Asn | N | 327 | Lys | K |

TABLE 5-continued

| | S237 | | | DSM12648 | | | 1139 | | | 64 | | | KSM635 | | | N4 | | |
|---|---|---|---|---|---|---|---|---|---|---|---|---|---|---|---|---|---|---|
| Amino acid position | Amino acid (3-letter code) | Amino acid (1-letter code) | Amino acid position | Amino acid (3-letter code) | Amino acid (1-letter code) | Amino acid position | Amino acid (3-letter code) | Amino acid (1-letter code) | Amino acid position | Amino acid (3-letter code) | Amino acid (1-letter code) | Amino acid position | Amino acid (3-letter code) | Amino acid (1-letter code) | Amino acid position | Amino acid (3-letter code) | Amino acid (1-letter code) |
| 310 | Gln | Q | 281 | Gln | Q | 310 | Gln | Q | 309 | Gln | Q | 490 | Gln | Q | 340 | Glu | E |
| 312 | Ser | S | 283 | Asn | N | 312 | Asn | N | 311 | Asn | N | 492 | Asn | N | 342 | Asp | D |
| 318 | Tyr | Y | 289 | Tyr | Y | 318 | Tyr | Y | 317 | Tyr | Y | 498 | Tyr | Y | 348 | Tyr | Y |
| 324 | Val | V | 295 | Val | V | 324 | Val | V | 323 | Val | V | 504 | Val | V | 354 | Val | V |
| 345 | Asn | N | 316 | Asn | N | 345 | Asn | N | 344 | Asn | N | 525 | Asn | N | 375 | Asn | N |
| 354 | Phe | F | 325 | Phe | F | 354 | Phe | F | 353 | Phe | F | 534 | Phe | F | 384 | Phe | F |
| 356 | Leu | L | 327 | Leu | L | 356 | Leu | L | 355 | Leu | L | 536 | Leu | L | 386 | Leu | L |
| 357 | Gly | G | 328 | Gly | G | 357 | Gly | G | 356 | Gly | G | 537 | Gly | G | 387 | Asn | N |
| 360 | Asn | N | 331 | Asn | N | 360 | Asn | N | 359 | Asn | N | 540 | Asp | D | 390 | Asp | D |
| 363 | Asn | N | 334 | Asn | N | 363 | Ser | S | 362 | Ser | S | 543 | Asp | D | 393 | Asp | D |
| 368 | Pro | P | 339 | Pro | P | 368 | Pro | P | 367 | Pro | P | 548 | Ala | A | 398 | Glu | E |

In Examples 3 and 4 described below, the mutant S237 cellulases in which the amino acid residues at position 71 and position 193 among the non-charged amino acid residues at the positions selected as described above were substituted with charged amino acid residues, were constructed.

7) Investigation of Relationship Between Adsorption Power of Alkaline Cellulase to Cellulose and Anti-Redeposition Ability, and Determination of Amino Acid Residues to be Substituted that Enhance Anti-Redeposition Ability Promotion of adsorption of the alkaline cellulases to cellulose by addition of sodium chloride was shown according to a method similar to the method of "4) Evaluation of anti-redeposition ability", as follows.

Bacillus sp. strain KSM-635-derived alkaline cellulase (635 cellulase) was produced according to methods reported (in Agric. Bio. Chem., 55, 2387, 1991). Subsequently, 0.33 g of a cleaning agent composition was dissolved in 500 mL of water ($CaCl_2$: 55.42 mg/L, $MgCl_2.6H_2O$: 43.51 mg/L), and 2110 mU of 635 cellulase, and sodium chloride in an amount of 5% relative to the total amount of the washing water were added to the solution, to obtain a washing water. The washing water thus prepared was transferred into the sample cup of an agitation type detergency tester, Terg-O-To meter; Ueshima Seisakusho Co., Ltd.) at 20° C. As a cloth for evaluation, 5 sheets of a white cotton cloth (#2003 white woven fabric, 100% cotton, supplied by Tanigashira Shoten) having a size of 6 cm×6 cm were placed in the sample cup, and 40 g of a white knitted cotton cloth (seared bleached cloth (supplied by Tanigashira Shoten) that had been washed and then sufficiently rinsed) was introduced to the sample cup. The contents were stirred for 10 minutes at rotation speed of 80±4 rpm. Subsequently, the white cotton cloth was removed together with the white knitted cotton cloth, and the clothes were lightly wrung out and then rapidly introduced into 2000 mL of tap water. Only the white cotton cloth was taken out therefrom, and the cloth was dehydrated without rinsing and then was introduced into a Coomassie Brilliant Blue G staining solution (prepared by dissolving 2.5 g of Coomassie Brilliant Blue G250 (Merck GmbH), 4 g of methanol, and 90 mL of acetic acid in 910 mL of deionized water). After immersion for 30 minutes, the cloth was lightly wrung out and then was transferred into a decolorization solution (prepared by mixing 50 mL of deionized water, 50 mL of methanol and 10 mL of acetic acid). Immersion of the cloth in the decolorization solution for 30 minutes was repeated two times. Subsequently, the cloth was washed with water and was subjected to finish ironing. Then, the brightness (L value) was measured using a spectrophotometer, CM-3500d (Konica Minolta Holdings, Inc.). A control experiment was carried out by the same procedure, except that sodium chloride was not added to the washing water.

As a result, while the L value in the case of non-addition of sodium chloride was 92, the L value in the case of adding sodium chloride in an amount of 5% was 71. Since the L value decreases with the adsorption of proteins to the cloth, this decrease in the L value means an increase in the amount of adsorption of 635 cellulase to the white cotton cloth. That is, it was shown that the adsorption of the alkaline cellulase to cellulose was promoted by the addition of sodium chloride.

Subsequently, the anti-redeposition ability of 635 cellulase in the presence of sodium chloride was evaluated according to the section "4) Evaluation of anti-redeposition ability", using washing water to which sodium chloride had been added in an amount of 5%. A cleaning agent of the composition B, and 1000 mU of 635 cellulase were used. As the carbon black, Asahi carbon black for cleaning was used. As control experiments, the same evaluation with the proviso that sodium chloride was not added to the washing water, and that no cellulase was added, was carried out.

As a result, the anti-redeposition ratio in the case of adding sodium chloride was 47% in the washing water without any added cellulase, and was 30% in the washing water with an added cellulase, in which a decrease of the anti-redeposition ratio in the presence of a cellulase was observed. On the other hand, in the case where sodium chloride was not added, the anti-redeposition ratio was 72% in the washing water without addition of cellulase, and was 82% in the washing water with addition of cellulase, thus, an increase of the anti-redeposition ratio, in the presence of a cellulase, was observed. Taking into consideration of the above experimental results altogether, the result suggests that since the adsorption of the alkaline cellulase to cellulose was promoted in the presence of sodium chloride, a redeposition promoting effect was rather exhibited.

An alkaline cellulase adsorbs to cellulose via the cellulose binding module (CBM) in the interior of the enzyme. Thus, the result suggests that when the cellulose binding property of the alkaline cellulase via the cellulose binding module is decreased, it would be more difficult for the alkaline cellulase to adsorb to cellulose, therefore, higher anti-redeposition effect would be provided even under the condition where, for example, the cellulose adsorption is promoted (see FIG. 1B).

The cellulose binding module (CBM) of 635 cellulase or S237 cellulase consists of two kinds of CBMs that belong to CBM17 family and CBM28 family. Amino acid residues that directly participate in the binding to cellulose, which are included in the members of those CBM17 and CBM28 families, have already been reported (published as Biochem. J., 361, 35, 2002). For example, for the CBM17 of S237 cellulase, asparagine at position 419, aspartic acid at position 421, tryptophan at position 454, arginine at position 458, glutamine at position 495, tryptophan at position 501, asparagine at position 503, and asparagine at position 551 in the amino acid sequence set forth in SEQ ID NO: 2; and for the CBM28, alanine at position 605, glutamic acid at position 607, alanine at position 641, arginine at position 645, glutamine at position 684, tryptophan at position 691, glutamine at position 693, and isoleucine at position 740 participate in cellulose binding. Therefore, it suggests that when these amino acid residues are substituted with other amino acid residues, the binding property of the alkaline cellulase to cellulose may be weakened. Furthermore, it may be considered that amino acid residues adjacent to these amino acid residues (particularly, two amino acid residues adjacent to the relevant amino acid residues) also participate in cellulose binding either directly or indirectly. Therefore, the result suggests that the cellulose binding property may be weakened by substituting or deleting the amino acid residues that are adjacent to the amino acid residues that directly participate in cellulose binding, or by inserting amino acid residues at the positions more adjacent to the relevant residues. Based on such investigation results, 44 amino acid residues that can be considered as target of substitution so as to weaken the cellulose binding property of the alkaline cellulase are summarized in Table 6.

TABLE 6

| S237 | | | DSM12648 | | | 1139 | | | 64 | | | KSM635 | | | N4 | | |
|---|---|---|---|---|---|---|---|---|---|---|---|---|---|---|---|---|---|
| Amino acid position | Amino acid (3-letter code) | Amino acid (1-letter code) | Amino acid position | Amino acid (3-letter code) | Amino acid (1-letter code) | Amino acid position | Amino acid (3-letter code) | Amino acid (1-letter code) | Amino acid position | Amino acid (3-letter code) | Amino acid (1-letter code) | Amino acid position | Amino acid (3-letter code) | Amino acid (1-letter code) | Amino acid position | Amino acid (3-letter code) | Amino acid (1-letter code) |
| 418 | Val | V | 389 | Val | V | 418 | Val | V | 417 | Val | V | 598 | Val | V | 451 | Gln | Q |
| 419 | Asn | N | 390 | Asn | N | 419 | Asn | N | 418 | Asn | N | 599 | Asn | N | 452 | Asn | N |
| 420 | Ser | S | 391 | Ser | S | 420 | Gly | G | 419 | Gly | G | 600 | Gly | G | 453 | Ser | S |
| 421 | Asp | D | 392 | Asp | D | 421 | Asp | D | 420 | Asp | D | 601 | Asp | D | 454 | Asp | D |
| 422 | Ser | S | 393 | Ser | S | 422 | Ser | S | 421 | Ser | S | 602 | Ser | S | 455 | Ser | S |
| 453 | Phe | F | 424 | Phe | F | 452 | Tyr | Y | 451 | Tyr | Y | 633 | Tyr | Y | 486 | Tyr | Y |
| 454 | Trp | W | 425 | Trp | W | 453 | Trp | W | 452 | Trp | W | 634 | Trp | W | 487 | Trp | W |
| 455 | Ala | A | 426 | Ala | A | 454 | Ala | A | 453 | Ala | A | 635 | Asp | D | 488 | Ser | S |
| 457 | Ala | A | 428 | Ala | A | 456 | Ala | A | 455 | Ala | A | 637 | Val | V | 490 | Val | V |
| 458 | Arg | R | 429 | Arg | R | 457 | Arg | R | 456 | Arg | R | 638 | Arg | R | 491 | Arg | R |
| 459 | Leu | L | 430 | Leu | L | 458 | Leu | L | 457 | Leu | L | 639 | Leu | L | 492 | Ile | I |
| 494 | Pro | P | 465 | Pro | P | 493 | Pro | P | 492 | Pro | P | 674 | Pro | P | 527 | Pro | P |
| 495 | Gln | Q | 466 | Gln | Q | 494 | Gln | Q | 493 | Gln | Q | 675 | Gln | Q | 528 | Gln | Q |
| 496 | Ser | S | 467 | Ser | S | 495 | Gly | G | 494 | Gly | G | 676 | Gly | G | 529 | Ser | S |
| 500 | Gly | G | 471 | Gly | G | 499 | Asn | N | 498 | Asn | N | 680 | Gly | G | 533 | Glu | E |
| 501 | Trp | W | 472 | Trp | W | 500 | Trp | W | 499 | Trp | W | 681 | Trp | W | 534 | Trp | W |
| 502 | Ala | A | 473 | Ala | A | 501 | Val | V | 500 | Val | V | 682 | Ala | A | 535 | Ala | A |
| 503 | Asn | N | 474 | Asn | N | 502 | Asn | N | 501 | Asn | N | 683 | Asn | N | 536 | Asn | N |
| 504 | Pro | P | 475 | Pro | P | 503 | Pro | P | 502 | Pro | P | 684 | Pro | P | 537 | Ala | A |
| 550 | Asn | N | 521 | Asn | N | 548 | Asn | N | 547 | Asn | N | 729 | Ser | S | 583 | Asn | N |
| 551 | Asn | N | 522 | Asn | N | 549 | Asn | N | 548 | Asn | N | 730 | Asn | N | 584 | Asn | N |
| 552 | Ile | I | 523 | Ile | I | 550 | Ile | I | 549 | Ile | I | 731 | Ile | I | 585 | Ile | I |
| 604 | Trp | W | 575 | Trp | W | 602 | Trp | W | 601 | Trp | W | 783 | Trp | W | 639 | Trp | W |
| 605 | Ala | A | 576 | Ala | A | 603 | Ala | A | 602 | Ala | A | 784 | His | H | 640 | Asp | D |
| 606 | Gly | G | 577 | Gly | G | 604 | Gly | G | 603 | Gly | G | 785 | Thr | T | 641 | Ser | S |
| 607 | Glu | E | 578 | Glu | E | 605 | Glu | E | 604 | Glu | E | 786 | Glu | E | 642 | Glu | E |
| 608 | Ser | S | 579 | Ser | S | 606 | Ser | S | 605 | Ser | S | 787 | Ser | S | 643 | Ser | S |
| 640 | Trp | W | 611 | Trp | W | 638 | Trp | W | 637 | Trp | W | 819 | Trp | W | 675 | Trp | W |
| 641 | Ala | A | 612 | Ala | A | 639 | Ala | A | 638 | Ala | A | 820 | Ala | A | 676 | Ala | A |
| 642 | Thr | T | 613 | Thr | T | 640 | Thr | T | 639 | Thr | T | 821 | Thr | T | 677 | Thr | T |
| 644 | Pro | P | 615 | Pro | P | 642 | Pro | P | 641 | Pro | P | 823 | Pro | P | 679 | Pro | P |
| 645 | Arg | R | 616 | Arg | R | 643 | Arg | R | 642 | Arg | R | 824 | Arg | R | 680 | Arg | R |
| 646 | Leu | L | 617 | Leu | L | 644 | Leu | L | 643 | Leu | L | 825 | Leu | L | 681 | Leu | L |
| 683 | Phe | F | 654 | Phe | F | 681 | Phe | F | 680 | Phe | F | 862 | Phe | F | 720 | Phe | F |
| 684 | Gln | Q | 655 | Gln | Q | 682 | Gln | Q | 681 | Gln | Q | 863 | Gln | Q | 721 | Gln | Q |
| 685 | Pro | P | 656 | Pro | P | 683 | Pro | P | 682 | Pro | P | 864 | Pro | P | 722 | Pro | P |
| 690 | Tyr | Y | 661 | Tyr | Y | 688 | Tyr | Y | 687 | Tyr | Y | 869 | Tyr | Y | 727 | Tyr | Y |

TABLE 6-continued

| S237 | | DSM12648 | | | 1139 | | | 64 | | | KSM635 | | | N4 | | |
|---|---|---|---|---|---|---|---|---|---|---|---|---|---|---|---|---|
| Amino acid position | Amino acid (3-letter code) | Amino acid (1-letter code) | Amino acid position | Amino acid (3-letter code) | Amino acid (1-letter code) | Amino acid position | Amino acid (3-letter code) | Amino acid (1-letter code) | Amino acid position | Amino acid (3-letter code) | Amino acid (1-letter code) | Amino acid position | Amino acid (3-letter code) | Amino acid (1-letter code) | Amino acid position | Amino acid (3-letter code) | Amino acid (1-letter code) |
| 691 | Trp | W | 662 | Trp | W | 689 | Trp | W | 688 | Trp | W | 870 | Trp | W | 728 | Trp | W |
| 692 | Val | V | 663 | Val | V | 690 | Val | V | 689 | Val | V | 871 | Gln | Q | 729 | Ala | A |
| 693 | Gln | Q | 664 | Gln | Q | 691 | Gln | Q | 690 | Gln | Q | 872 | Glu | E | 730 | Gln | Q |
| 694 | Ala | A | 665 | Ala | A | 692 | Ala | A | 691 | Ala | A | 873 | Val | V | 731 | Ala | A |
| 739 | Met | M | 710 | Met | M | 737 | Met | M | 736 | Met | M | 919 | Leu | L | 775 | Leu | L |
| 740 | Ile | I | 711 | Ile | I | 738 | Ile | I | 737 | Ile | I | 920 | Leu | L | 776 | Ile | I |
| 741 | Ile | I | 712 | Ile | I | 739 | Ile | I | 738 | Ile | I | 921 | Ile | I | 777 | Phe | F |

In the column for "S237" in Table 6, 44 amino acid residues that may be considered as targets of substitution in the cellulose binding module of S237 cellulase, are shown. Furthermore, Table 6 shows amino acid residues, of other alkaline cellulases sharing high amino acid sequence identity with S237 cellulase, Bacillus sp. strain DSM12648-derived alkaline cellulase (DSM12648 cellulase; SEQ ID NO: 4), Bacillus sp. strain 1139-derived alkaline cellulase (1139 cellulase; SEQ ID NO: 6), Bacillus sp. strain KSM-64-derived alkaline cellulase (endo-1,4-β-glucanase) (64 cellulase; SEQ ID NO: 8), Bacillus sp. strain KSM-635-derived alkaline cellulase (KSM-635 cellulase; SEQ ID NO: 10), and Bacillus sp. strain N-4-derived alkaline cellulase (endoglucanase) (N4 cellulase; SEQ ID NO: 12), which are aligned to the 44 amino acid residues of S237 cellulase (that is, present at the positions corresponding to those residues) when an alignment of the amino acid sequence of each of the cellulases and the amino acid sequence of S237 cellulase is produced. Each of the positions of the amino acid residues is indicated with the number of the amino acid residue in the amino acid sequence of the alkaline cellulase set forth in the corresponding sequence ID number.

In Examples 5 and 6 described below, mutant S237 cellulases in which some amino acid residues among such amino acid residues that participate in cellulose binding (in Table 6, underlined residues, namely, the amino acid residues at the positions 419, 421, 454 and 501) were substituted with other amino acid residues, were constructed.

Example 1

Production of Mutant S237 Cellulase-1

A mutant S237 cellulase in which glutamine at position 58 of S237 cellulase (SEQ ID NO: 2) was substituted with arginine (S237-Q58R) was produced by introducing a nucleotide mutation to the S237 cellulase gene and recombinantly expressing the mutant, as follows.

PCR amplification was carried out according to the section "1) Amplification of DNA fragment", using, as a template, the genomic DNA extracted from Bacillus sp. strain KSM-S237 (FERM BP-7875) by a routine method, and using a primer set consisting of primers 237UB1 and Q58R-RV and a primer set consisting of primers Q58R-FW and S237RV indicated in the above Table 2-3. As a result, a 0.7-kb amplified DNA fragment which includes a nucleotide mutation introduced at the position corresponding to the amino acid residue at position 58 on the S237 cellulase gene (SEQ ID NO: 1) in the vicinity of the 3'-terminus and a region that is mainly in the upstream of the mutation position, and a 2.5-kb amplified DNA fragment which includes the nucleotide mutation in the vicinity of the 5'-terminus and a region that is mainly in the downstream of the mutation position, were obtained. The base sequence of the primer Q58R-RV thus used was designed based on the base sequence of the S237 cellulase gene, wherein the nucleotide mutation for substituting glutamine at position 58 of S237 cellulase with arginine is included. The base sequence of the primer Q58R-FW is a complementary sequence of the primer Q58R-RV.

Subsequently, the two fragments thus obtained were mixed to be used as templates, and SOE (splicing by Overlap Extension)-PCR (Horton R. M. et al., Gene (1989) 77(1), p. 61-68) was carried out according to the section "1) Amplification of DNA fragment", using a primer set consisting of 237UB1 and S237RV indicated in Table 1. Thus, a 3.2-kb DNA fragment in which those two fragments are linked through a complementary sequence was obtained.

The 3.2-kb DNA fragment thus obtained (mutant S237 cellulase gene) was inserted at the SmaI restriction enzyme cleavage point of a shuttle vector pHY300PLK, and thus a recombinant plasmid pHY-S237_Q58R was constructed. The base sequence of the mutant S237 cellulase gene inserted in the plasmid was confirmed by determining the sequence using a 3100 DNA Sequencer (Applied Biosystems, Inc.). Subsequently, a transformant obtained by introducing the recombinant plasmid pHY-S237_Q58R into Bacillus subtilis by the method according to the section "2) Gene introduction into Bacillus subtilis", was cultured. From the culture thus obtained, a recombinantly produced protein was isolated and purified by the same method as in the section "5) 1. Recombinant production of S237 cellulase", and quantification was carried out. This recombinant protein is a mutant S237 cellulase in which glutamine at position 58 of the amino acid sequence of S237 cellulase (SEQ ID NO: 2) has been substituted with arginine (hereinafter, also referred to as S237_Q58R). An enzyme sample containing the mutant S237 cellulase thus obtained was used in the evaluation of anti-redeposition ability in Test Example 1 described below.

Example 2

Production of Mutant S237 Cellulase-2

A mutant S237 cellulase, S237_Q242S, in which glutamine at position 242 of S237 cellulase (SEQ ID NO: 2) was substituted with serine, was produced by the same method as described in Example 1. That is, the upstream region of the S237 cellulase gene (SEQ ID NO: 1) containing the intended nucleotide mutation (region in the upstream of the vicinity of the mutation position), and the downstream region of the S237 cellulase gene (SEQ ID NO: 1) containing the intended nucleotide mutation (region in the downstream of the vicinity of the mutation position) were amplified by PCR, using a primer set consisting of 237UB1 and Q242S-RV and a primer set consisting of Q242S-FW and S237RV indicated in Table 2-3. Two DNA fragments thus obtained were used as templates, and thus a 3.2-kb DNA fragment containing the intended mutant S237 cellulase gene was amplified. The DNA fragment was inserted into a shuttle vector pHY300PLK, and thus a recombinant plasmid pHY-S237_Q242S was constructed. The base sequence of the mutant S237 cellulase gene inserted into the plasmid was confirmed, and a transformant obtained by introducing the recombinant plasmid into Bacillus subtilis by the method according to the section "2) Gene introduction into Bacillus subtilis" was cultured. A recombinant protein (that is, mutant S237 cellulase S237_Q242S) was isolated and purified from the culture thus obtained, and quantification of the recombinant protein was carried out.

Based on this mutant S237 cellulase S237_Q242S, two kinds of S237 cellulase double mutant, in which glutamine at position 58 was substituted with arginine or glutamic acid (QS_Q58R and QS_Q58E, respectively), were produced basically in the same manner as described in Example 1. First, two DNA fragments were obtained by performing PCR amplification of the upstream region (region in the upstream of the vicinity of the mutation position) of the mutant S237 cellulase S237_Q242S gene containing the intended nucleotide mutation in the vicinity of the 3'-terminal, and the downstream region (region in the downstream of the vicinity of the mutation position) of the mutant S237 cellulase S237_Q242S gene containing the intended nucleotide mutation, using the pHY-S237_Q2428 produced as described above as a template DNA, and respectively using two pairs of primer sets for introducing the intended mutations indicated in the above Table 2-3. Using the two DNA fragments thus obtained as templates, a DNA fragment including the intended mutant S237 cellulase gene was amplified. The DNA fragment was inserted into a shuttle vector pHY300PLK to construct a recombinant plasmid, and the base sequence of the mutant S237 cellulase gene inserted in the plasmid was confirmed. A transformant obtained by introducing the recombinant plasmid into *Bacillus subtilis* by the method according to the section "2) Gene introduction into *Bacillus subtilis*", was cultured. From the culture thus obtained, a recombinant protein (mutant S237 cellulase) was isolated and purified by the same method as in the section "5) 1. Recombinant production of S237 cellulase", and quantification of the recombinant protein was carried out. Enzyme samples containing the respective mutant S237 cellulases thus obtained were used in an evaluation of the anti-redeposition ability and an evaluation of stability in Test Examples 2 and 3 described below.

Example 3

Production of Mutant S237 Cellulase-3

A mutant S237 cellulase in which serine at position 193 of S237 cellulase (SEQ ID NO: 2) was substituted with arginine, was produced by introducing a nucleotide mutation into the S237 cellulase gene, and recombinantly expressing the mutant, as follows.

PCR amplification was carried out according to the section "1) Amplification of DNA fragment", using the genomic DNA extracted from *Bacillus* sp. strain KSM-S237 (FERM BP-7875) by a routine method as a template, and using a primer set consisting of primers 237UB1 and S193R-RV and a primer set consisting of primers S193R-FW and S237RV indicated in the above Table 2-1. As a result, a 0.7-kb amplified DNA fragment which includes a nucleotide mutation introduced at the position corresponding to the amino acid residue at position 193 on the S237 cellulase gene (SEQ ID NO: 1) in the vicinity of the 3'-terminus and a region that is mainly in the upstream of the mutation position, and a 2.5-kb amplified DNA fragment which includes the nucleotide mutation in the vicinity of the 5'-terminus and a region that is mainly in the downstream of the mutation position, were obtained. The base sequence of the primer S193R-RV thus used was designed based on the base sequence of S237 cellulase gene, wherein a nucleotide mutation for substituting serine at position 193 of S237 cellulase with arginine is included. The base sequence of the primer S193R-FW is a complementary sequence of the primer S193R-RV.

Subsequently, the two fragments thus obtained were mixed to be used as templates, and SOE (splicing by Overlap Extension)-PCR (Horton R. M. et al., Gene (1989) 77(1), p. 61-68) was carried out according to the section "1) Amplification of DNA fragment", using a primer set consisting of 237UB1 and S237RV indicated in Table 1. Thus, a 3.2-kb DNA fragment in which those two fragments are linked through a complementary sequence was obtained.

The 3.2-kb DNA fragment thus obtained (mutant S237 cellulase gene) was inserted at the SmaI restriction enzyme cleavage point of a shuttle vector pHY300PLK, and thus a recombinant plasmid pHY-S237(S193R) was constructed. The base sequence of the mutant S237 cellulase gene inserted in the plasmid was confirmed by determining the sequence using a 3100 DNA Sequencer (Applied Biosystems, Inc.). Subsequently, a transformant obtained by introducing the recombinant plasmid pHY-S237(S193R) into *Bacillus subtilis* by the method according to the section "2) Gene introduction into *Bacillus subtilis*", was cultured. From the culture thus obtained, a recombinantly produced protein was isolated and purified by the same method as in the section "5) 1. Recombinant production of S237 cellulase", and quantification was carried out. This recombinant protein is a mutant S237 cellulase in which serine at position 193 of the amino acid sequence of S237 cellulase (SEQ ID NO: 2) had been substituted with arginine (hereinafter, also referred to as S237_S193R). An enzyme sample containing the mutant S237 cellulase thus obtained, S237 S193R, was used in the evaluation of anti-redeposition ability in Test Example 4 described below.

Example 4

Production of Mutant S237 Cellulase-4

A mutant S237 cellulase in which the non-charged amino acid residues selected as described above were substituted with charged amino acid residues in the mutant S237 cellulase described in Example 2, S237_Q242S, was produced. Specifically, a S237 cellulase double mutant (QS_Q71E) in which glutamine at position 71 of the amino acid sequence of the mutant S237 cellulase S237_Q242S had been substituted with glutamic acid, was produced basically in the same manner as described in Example 3. First, two DNA fragments were obtained by performing PCR amplification of the upstream region (region in the upstream of the vicinity of the mutation position) of the mutant S237 cellulase S237_Q242S gene containing the intended nucleotide mutation in the vicinity of the 3'-terminal, and the downstream region (region in the downstream of the vicinity of the mutation position) of the mutant S237 cellulase S237_Q242S gene containing the intended nucleotide mutation, using the pHY-S237 (Q242S) produced as described above as a template DNA, and respectively using two pairs of primer sets for introducing the intended mutations indicated in the above Table 2-1. Using the two DNA fragments thus obtained as templates, a DNA fragment including the intended mutant S237 cellulase gene was amplified. That DNA fragment was inserted into a shuttle vector pHY300PLK to construct a recombinant plasmid, and the base sequence of the mutant S237 cellulase gene inserted in the plasmid was confirmed. A transformant obtained by introducing the recombinant plasmid into *Bacillus subtilis* by the method according to the section "2) Gene introduction into *Bacillus subtilis*", was cultured. From the culture thus obtained, a recombinant protein (mutant S237 cellulase) was isolated and purified by the same method as in the section "5) 1. Recombinant production of S237 cellulase", and quantification of the recombinant protein was carried out. Enzyme samples containing the respective mutant S237 cellulases thus obtained were used in an evaluation of the anti-redeposition ability and an evaluation of stability in Test Example 5 described below.

Example 5

Production of Mutant S237 Cellulase-5

Three kinds of mutant S237 cellulases, in which the amino acid residues participating in cellulose binding were substituted with introducing nucleotide mutations that cause intended amino acid substitutions into the S237 cellulase gene, and recombinantly expressing the mutants, were produced. Specifically, mutant S237 cellulases in which aspartic acid at position 421 of S237 cellulase (SEQ ID NO: 2) was substituted with alanine, tryptophan at position 454 substituted with tyrosine, and tryptophan at position 501 substituted with tyrosine (S237_D421A, S237_W454Y, and S237_W501Y, respectively) were produced.

For each of the mutant cellulases, two DNA fragments were obtained by performing PCR amplification of the upstream region (region in the upstream of the vicinity of the mutation position) of the mutant S237 cellulase gene containing the intended nucleotide mutations, and the downstream region (region in the downstream of the vicinity of the mutation position) of the mutant S237 cellulase gene containing the intended nucleotide mutations, respectively using two pairs of primer sets for introducing the intended mutations (see Table 2-2). Using the two DNA fragments thus obtained as templates, a DNA fragment including the intended mutant S237 cellulase gene was amplified. That DNA fragment was inserted into a shuttle vector pHY300PLK to construct a recombinant plasmid, and the base sequence of the mutant S237 cellulase gene inserted in the plasmid was confirmed. A transformant obtained by introducing the recombinant plasmid into *Bacillus subtilis* by the method according to the section "2) Gene introduction into *Bacillus subtilis*", was cultured. From the culture thus obtained, a recombinant protein (that is, each mutant S237 cellulase) was extracted and purified by the same method as in the section "5) 1. Recombinant production of S237 cellulase", and quantification of the recombinant protein was carried out. Enzyme samples containing the respective mutant S237 cellulases thus obtained were used in an evaluation of the anti-redeposition ability in Test Example 6 described below.

Example 6

Production of Mutant S237 Cellulase-6

A mutant S237 cellulase, in which the amino acid residues participating in cellulose binding were further substituted in the mutant S237 cellulase S237_Q242S described in Example 2, was produced. Specifically, a S237 cellulase double variant (QS_N419A) in which asparagine at position 419 of the amino acid sequence of the mutant S237 cellulase S237_Q242S was substituted with alanine, was produced basically in the same manner as described in Example 5. That is, two DNA fragments were obtained by performing PCR amplification of the upstream region (region in the upstream of the vicinity of the mutation position) of the mutant S237 cellulase S237_Q242S gene containing the intended nucleotide mutation, and the downstream region (region in the downstream of the vicinity of the mutation position) of the mutant S237 cellulase S237_Q242S gene containing the intended nucleotide mutation, using the pHY-S237(Q242S) produced as described above as a template DNA and respectively using two pairs of primer sets for introducing the intended mutations (see Table 2-2). Using the two DNA fragments thus obtained as templates, a DNA fragment including the intended mutant S237 cellulase gene was amplified. That DNA fragment was inserted into a shuttle vector pHY300PLK to construct a recombinant plasmid, and the base sequence of the mutant S237 cellulase gene inserted in the plasmid was confirmed. A transformant obtained by introducing the recombinant plasmid into *Bacillus subtilis* by the method according to the section "2) Gene introduction into *Bacillus subtilis*", was cultured. From the culture thus obtained, a recombinant protein (that is, each mutant S237 cellulase) was isolated and purified by the same method as in the section "5) 1. Recombinant production of S237 cellulase", and quantification of the recombinant protein was carried out. Enzyme samples containing the respective mutant S237 cellulases thus obtained were used in an evaluation of the anti-redeposition ability in Test Example 7 described below.

Test Example 1

Evaluation of Anti-Redeposition Ability of Mutant S237 Cellulase-1

The anti-redeposition ability of mutant S237 cellulase S237_Q58R produced in Example 1 was evaluated according to the section "4) Evaluation of anti-redeposition ability" described above. Furthermore, for the evaluation, 50 g of a white knitted cotton cloth [seared bleached cloth (supplied by Tanigashira Shoten) that had been washed and then sufficiently rinsed] was introduced, such that the amount of cloth with respect to the solution (bath ratio) would be 10 L/kg. The detergent composition B described above was used, and an amount of enzyme equivalent to the amount of protein exhibiting 52.8 mU of the wild-type S237 cellulase activity with respect to the S237_Q58R, was used. The results obtained are shown in Table 7. Enhanced anti-redeposition ability of the mutant S237 cellulase S237_Q58R as compared with S237 cellulase was observed.

TABLE 7

| Enzyme | Effect of mutation on anti-redeposition (%) |
| --- | --- |
| Control | 0 |
| S237_Q58R | 2.77 |

Test Example 2

Evaluation of Anti-Redeposition Ability of Mutant S237 Cellulase-2

The anti-redeposition ability of the mutant S237 cellulases QS_Q58R and QS_Q58E that had been produced in Example 2 using S237_Q242S as the parent cellulase, was evaluated according to the section "4) Evaluation of anti-redeposition ability" described above. Furthermore, upon the evaluation, assuming the co-presence of sebum dirt components, three sheets of a stained cloth wfk10D (Wfk Testgewebe GmbH (D41379, Germany)) each having a size of 6 cm×6 cm were added. A cleaning agent of the composition C was used, and an amount of enzyme equivalent to the amount of protein exhibiting 52.8 mU of the S237_Q242S cellulase activity was used. In the present evaluation, S237_Q242S was used as a control enzyme. The results thus obtained are presented in Table 8. For any of the mutant S237 cellulases evaluated and used, a high anti-redeposition effect was obtained as compared with the control enzyme (S237_Q242S), and the enhanced anti-redeposition ability by mutagenesis was observed.

TABLE 8

| Enzyme | Effect of mutation on anti-redeposition (%) |
| --- | --- |
| Control | 0 |
| QS_Q58E | 3.03 |
| Control | 0 |
| QS_Q58R | 8.92 |

Test Example 3

Stability Test of Mutant S237 Cellulase in Liquid Cleaning Agent

Stability was evaluated for the case where the mutant S237 cellulase QS_Q58R produced by using S237_Q242S as a parent cellulase in Example 3 was stored in a cleaning agent of the composition E to which various alkaline proteases were added.

As the alkaline proteases, alkaline proteases KP43 (Japanese Patent No. 3479509), Kannase™ (Novozymes, Inc.) and Properase™ (Danisco AS) were used. These three kinds of alkaline proteases are all subtilisin-like alkaline proteases suitable to be incorporated into cleaning agents.

To 450 µL of the cleaning agent of the composition E, 460 U/L of a cellulase (S237QS or S237QS_Q58R) and 0.012 g each, as an amount of protein, of the three kinds of alkaline proteases described above (an amount of protein equivalent to the addition of 29 U/L for KP43) were added, and liquid amount of the samples were adjusted to 500 µL, and were stored at 40° C. The residual cellulase activity in the cleaning agent after 24 hours was measured.

The cellulase activity was measured by the method of using p-nitrophenyl-β-D-cellotrioside described in Example 1, and the residual cellulase activity was calculated by the following formula.

Residual cellulase activity (%)=(Cellulase activity after 24 hours of storage/cellulase activity immediately after preparation)×100     [Mathematical formula 8]

Figure 4:
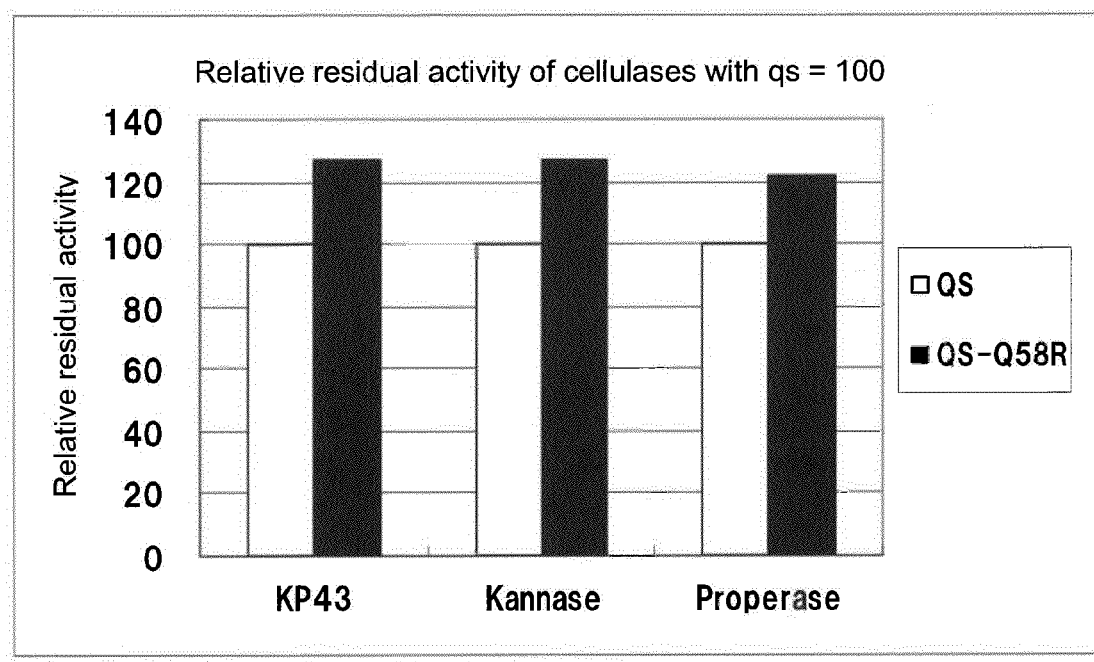
FIG. 4 is a diagram illustrating the results of a comparison of the residual activity (when the activity of S237_Q242S (QS) is 100) of a cellulase in the presence of various proteases.

The experimental results are presented in FIG. 4. The relative residual activity of QS_Q58R is shown by defining the residual activity value of S237_QS after storage for 24 hours at 40° C. as 100. For all of the systems to which the three kinds of proteases were added, QS_Q58R exhibited higher residual activity as compared with S237QS. From these results, enhancements of the anti-redeposition ability and the protease resistance by substituting glutamine at position 58 of S237 cellulase with arginine were observed.

Test Example 4

Evaluation of Anti-Redeposition Ability of Mutant S237 Cellulase-3

The anti-redeposition ability of the mutant S237 cellulase S237_S193R produced in Example 3 was evaluated according to the section "4) Evaluation of anti-redeposition ability" described above. Furthermore, for the evaluation, 50 g of a white knitted cotton cloth [seared bleached cloth (supplied by Tanigashira Shoten) that had been washed and then sufficiently rinsed] was introduced, such that the amount of cloth with respect to the solution (bath ratio) would be 10 L/kg. A cleaning agent of the composition F described above was used, and an amount of enzyme equivalent to the amount of protein exhibiting 52.8 mU of the wild-type S237 cellulase activity with respect to the S237_S193R, was used. Asahi carbon black for cleaning was used as the carbon black, and the hardness of the used water was adjusted to 12° DH. The results thus obtained are shown in Table 9. Furthermore, the value of solvent accessibility determined in Example 2 is also presented. With S237_S193R, a higher anti-redeposition effect as compared with the control enzyme (S237_Q242S) was provided, and enhancement of the anti-redeposition ability by the mutagenesis was observed.

TABLE 9

| Mutant S237 cellulase | Degree of anti-redeposition ability enhancement in mutant cellulase (%) | Solvent accessibility of residue at mutation position |
|---|---|---|
| S237_S193R | 3.26 | 76.08 |

Test Example 5

Evaluation of Anti-Redeposition Ability of Mutant S237 Cellulase-4

The anti-redeposition ability of the mutant S237 cellulase QS_Q71E produced in Example 4 using S237_Q242S as a base, was evaluated according to the section "4) Evaluation of anti-redeposition ability" described above.

A cleaning agent of the composition C described above was used, and an amount of enzyme equivalent to the amount of protein exhibiting 52.8 mU of the wild-type S237 cellulase activity with respect to QS_Q71E, was used. For the present evaluation, S237_Q242S was used as a control enzyme. Asahi carbon black for cleaning was used as the carbon black, and the hardness of the used water was adjusted to 4° DH. Furthermore, upon the evaluation, assuming the co-presence of sebum dirt components, three sheets of a stained cloth wfk10D (Wfk Testgewebe GmbH (D41379, Germany)) each having a size of 6 cm×6 cm were added. The results thus obtained are shown in Table 10. Further, the value of the solvent accessibility of residues determined in the section "6) Steric structure modeling of S237 cellulase" described above is also shown. Higher anti-redeposition effect as compared with the control enzyme (S237_Q242S) was provided in QS_Q71E, and enhancement of the anti-redeposition ability by the mutagenesis was observed. From the results of the present Test Example and the Test Example 4, it was demonstrated that the anti-redeposition ability of the mutant S237 cellulases can be enhanced by substituting the non-charged amino acid residues selected as described above, with charged amino acid residues. The result suggests that such amino acid substitution caused high repulsion between the enzyme surface and hydrophobic carbon black by further increasing the hydrophilicity of the enzyme surface, as speculated in the above, and thereby a higher anti-redeposition effect was provided.

TABLE 10

| Mutant S237 cellulase | Degree of anti-redeposition ability enhancement in mutant cellulase (%) | Solvent accessibility of residue at mutation position |
|---|---|---|
| QS_Q71E | 6.06 | 116.3 |

Test Example 6

Evaluation of Anti-Redeposition Ability of Mutant S237 Cellulase-5

The anti-redeposition ability of the mutant S237 cellulases produced in Example 5, S237_D421A, S237_W454Y and S237_W501Y, was evaluated according to the section "4) Evaluation of anti-redeposition ability" described above. For the evaluation, 50 g of a white knitted cotton cloth [seared bleached cloth (supplied by Tanigashira Shoten) that had been washed and then sufficiently rinsed] was introduced, such that the amount of cloth with respect to the solution (bath ratio) would be 10 L/kg. A cleaning agent of the composition B described above was used, and an amount of enzyme equivalent to the amount of protein exhibiting 52.8 mU of the wild-type S237 cellulase activity with respect to each of the mutant S237 cellulases, was used. In the present evaluation, the wild-type S237 cellulase was used as a control enzyme. Asahi carbon black for cleaning was used as the carbon black, and the hardness of the used water was adjusted to 12° DH. The results thus obtained are shown in Table 11. For all of the mutant S237 cellulases, an enhancement of the anti-redeposition ability as compared with S237 cellulase was observed. Therefore, it was demonstrated that when the amino acid residues that participate in cellulose binding in the cellulose binding module of an alkaline cellulase are substituted with other amino acid residues, the anti-redeposition ability of a mutant S237 cellulase can be enhanced. The result suggests that such amino acid substitution decreased the cellulose binding property of the alkaline cellulase as speculated in the above, and thereby a higher anti-redeposition effect was provided.

TABLE 11

| Mutant S237 cellulase | Degree of anti-redeposition ability enhancement in mutant cellulase (%) |
|---|---|
| S237_D421A | 3.29 |
| S237_W454Y | 4.21 |
| S237_W501Y | 10.5 |

Test Example 7

Evaluation of Anti-Redeposition Ability of Mutant S237 Cellulase-6

The anti-redeposition ability of the mutant S237 cellulase QS_N419A produced in Example 6 using S237_Q242S as a base, was evaluated according to the section "4) Evaluation of anti-redeposition ability" described above. For the evaluation, 45 g of a white knitted cotton cloth [seared bleached cloth (supplied by Tanigashira Shoten) that had been washed and then sufficiently rinsed] was introduced, such that the amount of cloth with respect to the solution (bath ratio) would be 11 L/kg. A cleaning agent of the composition C described above was used, and an amount of enzyme equivalent to the amount of protein exhibiting 52.8 mU of the wild-type S237 cellulase activity with respect to QS_N419A, was used. In the present evaluation, S237_Q242S was used as a control enzyme. Asahi carbon black for cleaning was used as the carbon black, and the hardness of the used water was adjusted to 4° DH. Furthermore, upon the evaluation, assuming the co-presence of sebum dirt components, three sheets of a stained cloth wfk10D (Wfk Testgewebe GmbH (D41379, Germany)) each having a size of 6 cm×6 cm were added. The results thus obtained are shown in Table 12. Higher anti-redeposition effect as compared with the control enzyme (S237_Q242S) was provided in QS_N419A, and enhancement of the anti-redeposition ability by the mutagenesis was observed. That is, it was demonstrated that when the amino acid residues that participate in cellulose binding in the cellulose binding module of an alkaline cellulase are substituted with other amino acid residues, the anti-redeposition ability of a mutant S237 cellulase can be enhanced. The result suggests that such amino acid substitution decreased the cellulose binding property of the alkaline cellulase as speculated in the above, and thereby a higher anti-redeposition effect was provided.

TABLE 12

| Mutant S237 cellulase | Degree of anti-redeposition ability enhancement in mutant cellulase (%) |
|---|---|
| QS_N419A | 4.62 |

What is claimed is:

1. A method for enhancing anti-redeposition ability of an alkaline cellulase, or method for both enhancing anti-redeposition ability and protease resistance of an alkaline cellulase, the method comprising substituting a glutamine residue at the position corresponding to position 58 of the amino acid sequence of an alkaline cellulase as set forth in SEQ ID NO: 2 or of an amino acid sequence having at least 90% identity with the amino acid sequence of SEQ ID NO: 2, with a glutamic acid or arginine residue.

2. The method of claim 1, wherein the glutamine residue is substituted with a glutamic acid residue.

3. The method of claim 1, wherein the glutamine residue is substituted with an arginine residue.

4. The method of claim 1, wherein the alkaline cellulase that has at least 90% identity with the amino acid sequence set forth in SEQ ID NO: 2 lacks the signal sequence that corresponds to amino acids 1 to 30 of SEQ ID NO: 2.

5. The method of claim 1, wherein the method further comprises substituting a glutamine residue at the position corresponding to position 71 of the amino acid sequence of an alkaline cellulase set forth in SEQ ID NO: 2 or of an amino acid sequence having at least 90% identity with the amino acid sequence of SEQ ID NO: 2, with a glutamic acid residue.

6. The method of claim 1, wherein the method further comprises substituting a serine residue at the position corresponding to position 193 of the amino acid sequence of an alkaline cellulase set forth in SEQ ID NO: 2 or of an amino acid sequence having at least 90% identity with the amino acid sequence of SEQ ID NO: 2, with an arginine residue.

7. The method of claim 1, wherein the method further comprises substituting a glutamine residue at the position corresponding to position 242 of the amino acid sequence of an alkaline cellulase set forth in SEQ ID NO: 2 or of an amino acid sequence having at least 90% identity with the amino acid sequence of SEQ ID NO: 2, with a serine residue.

8. The method of claim 1, wherein the method further comprises substituting an asparagine residue at the position corresponding to position 419 of the amino acid sequence of an alkaline cellulase set forth in SEQ ID NO: 2 or of an amino acid sequence having at least 90% identity with the amino acid sequence of SEQ ID NO: 2, with an alanine residue.

9. The method of claim 1, wherein the method further comprises substituting an aspartic acid residue at the position corresponding to position 421 of the amino acid sequence of an alkaline cellulase set forth in SEQ ID NO: 2 or of an amino acid sequence having at least 90% identity with the amino acid sequence of SEQ ID NO: 2, with an alanine residue.

10. The method of claim 1, wherein the method further comprises substituting a tryptophan residue at the position corresponding to position 454 of the amino acid sequence of an alkaline cellulase set forth in SEQ ID NO: 2 or of an amino acid sequence having at least 90% identity with the amino acid sequence of SEQ ID NO: 2, with a tyrosine residue.

11. The method of claim 1, wherein the method further comprises substituting a tryptophan residue at the position corresponding to position 501 of the amino acid sequence of an alkaline cellulase set forth in SEQ ID NO: 2 or of an amino acid sequence having at least 90% identity with the amino acid sequence of SEQ ID NO: 2, with a tyrosine residue.

* * * * *